United States Patent
Larson et al.

(10) Patent No.: US 11,051,751 B2
(45) Date of Patent: Jul. 6, 2021

(54) CALIBRATED SYSTEMS, DEVICES AND METHODS FOR PREVENTING, DETECTING, AND TREATING PRESSURE-INDUCED ISCHEMIA, PRESSURE ULCERS, AND OTHER CONDITIONS

(71) Applicant: Leaf Healthcare, Inc., Pleasanton, CA (US)

(72) Inventors: Barrett J Larson, Palo Alto, CA (US); Daniel Z. Shen, Palo Alto, CA (US); Mark V. Weckwerth, Pleasanton, CA (US); Charles Matthew Peterson Hammond, Pleasant Hill, CA (US)

(73) Assignee: LEAF HEALTHCARE, INC., Pleasanton, CA (US)

( * ) Notice: Subject to any disclaimer, the term of this patent is extended or adjusted under 35 U.S.C. 154(b) by 362 days.

(21) Appl. No.: 15/186,542

(22) Filed: Jun. 20, 2016

(65) Prior Publication Data

US 2016/0296160 A1  Oct. 13, 2016

Related U.S. Application Data

(63) Continuation-in-part of application No. 13/070,189, filed on Mar. 23, 2011, now Pat. No. 10,729,357, and (Continued)

(51) Int. Cl.
*A61B 5/00* (2006.01)
*G16H 40/63* (2018.01)
(Continued)

(52) U.S. Cl.
CPC ............. *A61B 5/447* (2013.01); *A41B 9/00* (2013.01); *A61B 5/002* (2013.01); *A61B 5/01* (2013.01);
(Continued)

(58) Field of Classification Search
None
See application file for complete search history.

(56) References Cited

U.S. PATENT DOCUMENTS 3,602,215 A   8/1971   Parnell ........................ 600/508
4,055,168 A   10/1977  Miller et al. ................ 600/594
(Continued)

FOREIGN PATENT DOCUMENTS

JP   08238275 A   9/1996   ............... A61B 5/00
JP   11136191 A   5/1999   ............... A61B 5/00
(Continued)

OTHER PUBLICATIONS

Progressively, Merriam-Webster.com, https://www.merriam-webster.com/dictionary/progressively, 8 pages, printed out on Nov. 9, 2020. (Year: 2020).*

(Continued)

*Primary Examiner* — Matthew Kremer
(74) *Attorney, Agent, or Firm* — Slayden Grubert Beard PLLC

(57) ABSTRACT

A system for monitoring medical conditions including pressure ulcers, pressure-induced ischemia and related medical conditions comprises at least one sensor adapted to detect one or more patient characteristic including at least position, orientation, temperature, acceleration, moisture, resistance, stress, heart rate, respiration rate, and blood oxygenation, a host for processing the data received from the sensors together with historical patient data to develop an assessment of patient condition and suggested course of treatment, including either suspending or adjusting turn schedule based on various types of patient movement. The sensor can include bi-axial or tri-axial accelerometers, as well as resistive, inductive, capacitive, magnetic and other sensing (Continued)

devices, depending on whether the sensor is located on the patient or the support surface, and for what purpose.

21 Claims, 20 Drawing Sheets

Related U.S. Application Data a continuation-in-part of application No. 15/036,782, filed as application No. PCT/US2014/066016 on Nov. 17, 2014, now Pat. No. 10,140,837, application No. 15/186,542, which is a continuation-in-part of application No. 14/244,720, filed as application No. PCT/US2012/000488 on Oct. 3, 2012, application No. 15/186,542, which is a continuation-in-part of application No. 14/543,887, filed on Nov. 17, 2014, now Pat. No. 9,728,061, and a continuation-in-part of application No. 15/028,018, filed as application No. PCT/US2014/059756 on Oct. 8, 2013, now Pat. No. 9,655,546, application No. 15/186,542, which is a continuation-in-part of application No. 15/183,739, filed on Jun. 15, 2016, now Pat. No. 10,588,565.

(60) Provisional application No. 61/429,732, filed on Jan. 4, 2011, provisional application No. 61/326,664, filed on Apr. 22, 2010, provisional application No. 61/411,647, filed on Nov. 9, 2010, provisional application No. 61/393,364, filed on Oct. 15, 2010, provisional application No. 61/373,260, filed on Aug. 12, 2010, provisional application No. 61/542,785, filed on Oct. 3, 2011, provisional application No. 61/905,106, filed on Nov. 15, 2013, provisional application No. 62/047,642, filed on Sep. 8, 2014, provisional application No. 61/888,078, filed on Oct. 8, 2013.

(51) Int. Cl.

| | | |
|---|---|---|
| *A61B 5/01* | (2006.01) | |
| *A61B 5/0205* | (2006.01) | |
| *A61B 5/024* | (2006.01) | |
| *A61B 5/026* | (2006.01) | |
| *A61B 5/11* | (2006.01) | |
| *A41B 9/00* | (2006.01) | |
| *A61G 7/057* | (2006.01) | |
| *G16H 20/40* | (2018.01) | |
| *G16H 40/67* | (2018.01) | |
| *G16H 20/00* | (2018.01) | |
| *G01P 21/00* | (2006.01) | |
| *A61B 5/0531* | (2021.01) | |
| *A61B 5/08* | (2006.01) | |
| *A61B 5/113* | (2006.01) | |
| *A61B 5/1455* | (2006.01) | |
| *A61B 7/00* | (2006.01) | |
| *G01P 15/18* | (2013.01) | |
| *A61B 5/363* | (2021.01) | |
| *A61B 5/145* | (2006.01) | |

(52) U.S. Cl.
CPC ............ *A61B 5/024* (2013.01); *A61B 5/0205* (2013.01); *A61B 5/026* (2013.01); *A61B 5/02055* (2013.01); *A61B 5/1113* (2013.01); *A61B 5/1114* (2013.01); *A61B 5/1115* (2013.01); *A61B 5/1118* (2013.01); *A61B 5/1121* (2013.01); *A61B 5/4833* (2013.01); *A61B 5/4866* (2013.01); *A61B 5/4884* (2013.01); *A61B 5/6801* (2013.01); *A61B 5/6823* (2013.01); *A61B 5/6843* (2013.01); *A61B 5/6891* (2013.01); *A61B 5/6892* (2013.01); *A61B 5/721* (2013.01); *A61B 5/7246* (2013.01); *A61B 5/7275* (2013.01); *A61B 5/7282* (2013.01); *A61B 5/746* (2013.01); *A61G 7/057* (2013.01); *A61G 7/05769* (2013.01); *G01P 21/00* (2013.01); *G16H 20/00* (2018.01); *G16H 20/40* (2018.01); *G16H 40/63* (2018.01); *G16H 40/67* (2018.01); *A61B 5/0261* (2013.01); *A61B 5/0531* (2013.01); *A61B 5/0816* (2013.01); *A61B 5/113* (2013.01); *A61B 5/1116* (2013.01); *A61B 5/14542* (2013.01); *A61B 5/14551* (2013.01); *A61B 5/363* (2021.01); *A61B 5/6804* (2013.01); *A61B 7/00* (2013.01); *A61B 2560/0223* (2013.01); *A61B 2562/02* (2013.01); *A61B 2562/029* (2013.01); *A61B 2562/0214* (2013.01); *A61B 2562/0219* (2013.01); *A61B 2562/0223* (2013.01); *A61B 2562/0247* (2013.01); *A61B 2562/0261* (2013.01); *A61B 2562/043* (2013.01); *A61B 2562/046* (2013.01); *A61G 2203/42* (2013.01); *A61G 2203/46* (2013.01); *G01P 15/18* (2013.01)

(56) References Cited

U.S. PATENT DOCUMENTS

| | | | |
|---|---|---|---|
| 5,038,137 A | 8/1991 | Lloyd | 340/573.7 |
| 5,146,206 A | 9/1992 | Callaway | 340/573.7 |
| 5,267,364 A | 12/1993 | Volk | 5/713 |
| 5,300,921 A | 4/1994 | Hoch et al. | 340/573.6 |
| 5,398,019 A | 3/1995 | Barnett et al. | 340/573.7 |
| 5,430,435 A | 7/1995 | Hoch et al. | 340/573.7 |
| 5,519,380 A | 5/1996 | Edwards | 340/573.4 |
| 5,588,437 A | 12/1996 | Byrne et al. | 600/504 |
| 5,623,760 A | 4/1997 | Newham | 29/622 |
| 5,669,377 A | 9/1997 | Feen | |
| 5,769,784 A | 6/1998 | Barnett et al. | 600/300 |
| 5,774,055 A | 6/1998 | Pomerantz | 340/573.7 |
| 5,906,016 A * | 5/1999 | Ferrand | A61G 7/00 5/600 |
| 6,014,346 A | 1/2000 | Malone | 368/10 |
| 6,030,351 A | 2/2000 | Schmidt et al. | 600/592 |
| 6,049,281 A | 4/2000 | Osterweil | 340/573.4 |
| 6,129,686 A | 10/2000 | Friedman | 600/595 |
| 6,287,253 B1 | 9/2001 | Ortega et al. | 600/300 |
| 6,305,221 B1 | 10/2001 | Hutchings | 73/488 |
| 6,397,190 B1 | 5/2002 | Goetz | 705/3 |
| 6,447,460 B1 | 9/2002 | Zheng | |
| 7,007,327 B2 | 3/2006 | Ogawa et al. | 5/609 |
| 7,090,647 B2 | 8/2006 | Mimura et al. | 600/587 |
| 7,184,963 B1 | 2/2007 | Shannon | 705/2 |
| 7,251,845 B2 | 8/2007 | Schaller et al. | 5/613 |
| 7,325,453 B2 | 2/2008 | Bremer et al. | |
| 7,378,975 B1 | 5/2008 | Smith et al. | 340/573.1 |
| 7,600,409 B2 | 10/2009 | Ukai | 73/1.39 |
| 7,634,379 B2 | 12/2009 | Noble | |
| 7,698,830 B2 | 4/2010 | Townsend et al. | 33/512 |
| 7,753,861 B1 | 7/2010 | Kahn et al. | 600/595 |
| 8,237,551 B2 | 8/2012 | Sweeney | |
| 8,284,070 B2 | 10/2012 | Chaudhari et al. | 340/686.1 |
| 8,306,666 B2 | 11/2012 | Huber et al. | 700/275 |
| 8,410,826 B2 | 4/2013 | Koto et al. | 327/108 |
| 8,410,926 B1 | 4/2013 | Gary, Jr. et al. | 340/539.12 |
| 8,436,737 B1 | 5/2013 | Trout | 340/573.7 |
| 8,475,368 B2 | 7/2013 | Tran et al. | 600/300 |
| 8,533,879 B1 | 9/2013 | Taylor | 5/713 |
| 8,594,776 B2 | 11/2013 | Mccombie et al. | 600/513 |
| 8,604,916 B2 | 12/2013 | McNeely | |
| 8,606,344 B2 | 12/2013 | Dimaio et al. | 600/407 |
| 8,674,826 B2 | 3/2014 | Becker et al. | |
| 8,684,900 B2 | 4/2014 | Tran | |

(56) References Cited

U.S. PATENT DOCUMENTS

| | | | |
|---|---|---|---|
| 8,781,504 B1 | 7/2014 | Liu | |
| 8,909,330 B2 | 12/2014 | Mccombie et al. | 600/513 |
| 8,956,293 B2 | 2/2015 | Mccombie et al. | 600/301 |
| 8,956,294 B2 | 2/2015 | Mccombie et al. | 600/301 |
| 9,005,141 B1 | 4/2015 | Najafi et al. | 600/595 |
| 9,055,928 B2 | 6/2015 | Mccombie et al. | |
| 9,141,974 B2 | 9/2015 | Jones et al. | |
| 9,492,092 B2 | 11/2016 | Mccombie et al. | |
| 9,566,007 B2 | 2/2017 | Mccombie et al. | |
| 9,655,546 B2 | 5/2017 | Shen et al. | |
| 9,901,261 B2 | 2/2018 | Mccombie et al. | |
| 10,004,447 B2 | 6/2018 | Shen et al. | |
| 10,020,075 B2 | 7/2018 | Perlman et al. | |
| 10,631,732 B2 | 4/2020 | Larson et al. | |
| 2001/0049609 A1 | 12/2001 | Girouard et al. | 705/3 |
| 2001/0050613 A1 | 12/2001 | Clark | 340/539.32 |
| 2003/0171954 A1 | 9/2003 | Guerin et al. | 705/2 |
| 2004/0015058 A1 | 1/2004 | Besson et al. | 600/301 |
| 2004/0046668 A1* | 3/2004 | Smith | A61B 5/1115 340/573.7 |
| 2005/0033200 A1 | 2/2005 | Soehren et al. | 600/595 |
| 2005/0172398 A1 | 8/2005 | Smith et al. | 5/81.1 R |
| 2005/0251914 A1 | 11/2005 | Schaller et al. | 5/601 |
| 2005/0256435 A1 | 11/2005 | Hess | 602/2 |
| 2006/0001545 A1 | 1/2006 | Wolf | 340/573.1 |
| 2006/0021240 A1 | 2/2006 | Horgan | 33/366.11 |
| 2006/0031102 A1 | 2/2006 | Teller et al. | 705/3 |
| 2006/0089538 A1 | 4/2006 | Cuddihy et al. | 600/300 |
| 2006/0097983 A1 | 5/2006 | Haggman et al. | 345/156 |
| 2006/0116904 A1 | 6/2006 | Brem | 705/2 |
| 2006/0270949 A1 | 11/2006 | Mathie et al. | 600/595 |
| 2006/0279426 A1 | 12/2006 | Bonnet | |
| 2007/0000154 A1 | 1/2007 | Dibenedetto et al. | 36/132 |
| 2007/0038155 A1 | 2/2007 | Kelly, Jr. et al. | 600/595 |
| 2007/0115277 A1 | 5/2007 | Wang et al. | 345/419 |
| 2007/0118056 A1 | 5/2007 | Wang et al. | 600/595 |
| 2007/0130893 A1 | 6/2007 | Davies | 54/1 |
| 2007/0132597 A1 | 6/2007 | Rodgers | 340/573.1 |
| 2007/0159332 A1 | 7/2007 | Koblasz | 340/572.1 |
| 2007/0175949 A1 | 8/2007 | Shelton, IV et al. | 227/176.1 |
| 2007/0241261 A1 | 10/2007 | Wendt | 250/221 |
| 2008/0001735 A1 | 1/2008 | Tran | 340/539.22 |
| 2008/0031102 A1 | 2/2008 | Oettinger et al. | 369/44.28 |
| 2008/0103447 A1 | 5/2008 | Reggiardo et al. | 604/131 |
| 2008/0129518 A1 | 6/2008 | Carlton-foss | 340/573.1 |
| 2008/0272918 A1 | 11/2008 | Ingersoll | |
| 2008/0275349 A1 | 11/2008 | Halperin et al. | 600/484 |
| 2009/0010178 A1 | 1/2009 | Tekippe | 370/254 |
| 2009/0024065 A1 | 1/2009 | Einarsson | 602/26 |
| 2009/0069642 A1 | 3/2009 | Gao et al. | 600/300 |
| 2009/0071249 A1 | 3/2009 | Kitazaki et al. | 73/514.33 |
| 2009/0099480 A1 | 4/2009 | Salgo et al. | 600/595 |
| 2009/0119843 A1 | 5/2009 | Rodgers et al. | 5/611 |
| 2009/0164250 A1 | 6/2009 | Hamilton et al. | 705/3 |
| 2009/0174565 A1 | 7/2009 | Chan et al. | 340/669 |
| 2009/0185763 A1 | 7/2009 | Park et al. | 382/311 |
| 2009/0237264 A1 | 9/2009 | Bobey et al. | 340/815.69 |
| 2009/0254003 A1 | 10/2009 | Buckman | |
| 2009/0318908 A1 | 12/2009 | Van Pieterson et al. | 606/9 |
| 2009/0322763 A1 | 12/2009 | Bang et al. | 345/474 |
| 2010/0010385 A1 | 1/2010 | Skelton et al. | 600/595 |
| 2010/0049096 A1 | 2/2010 | Ten Kate | 600/595 |
| 2010/0081385 A1 | 4/2010 | Lin et al. | 455/41.3 |
| 2010/0121226 A1 | 5/2010 | Ten Kate et al. | 600/595 |
| 2010/0121227 A1 | 5/2010 | Stirling et al. | 600/595 |
| 2010/0156653 A1 | 6/2010 | Chaudhari et al. | 340/686.1 |
| 2010/0162832 A1 | 7/2010 | Brauers | 73/862.626 |
| 2010/0231376 A1 | 9/2010 | Hirose | 340/517 |
| 2010/0268122 A1* | 10/2010 | Drennan | A61G 7/057 600/587 |
| 2010/0298656 A1 | 11/2010 | Mccombie et al. | 600/301 |
| 2010/0298661 A1 | 11/2010 | Mccombie et al. | 600/301 |
| 2010/0298742 A1 | 11/2010 | Perlman et al. | 600/595 |
| 2011/0025493 A1 | 2/2011 | Papadopoulos et al. | 340/539.12 |
| 2011/0046498 A1 | 2/2011 | Klap et al. | 600/534 |
| 2011/0046499 A1 | 2/2011 | Klewer et al. | 600/534 |
| 2011/0050411 A1 | 3/2011 | Schuman | |
| 2011/0066007 A1 | 3/2011 | Banet et al. | 600/301 |
| 2011/0066009 A1 | 3/2011 | Moon et al. | 600/301 |
| 2011/0082672 A1 | 4/2011 | Hardigan | 703/2 |
| 2011/0084806 A1 | 4/2011 | Perkins | 340/10.1 |
| 2011/0112442 A1 | 5/2011 | Meger et al. | 600/595 |
| 2011/0156915 A1 | 6/2011 | Brauers et al. | 340/573.4 |
| 2011/0201972 A1 | 8/2011 | Ten Kate | 600/595 |
| 2011/0234395 A1 | 9/2011 | Johnson et al. | 340/539.12 |
| 2011/0245732 A1 | 10/2011 | Mravyan et al. | 600/587 |
| 2011/0263950 A1 | 10/2011 | Larson et al. | 600/301 |
| 2012/0029392 A1 | 2/2012 | Jin et al. | 600/595 |
| 2012/0101770 A1 | 4/2012 | Grabiner et al. | 702/141 |
| 2012/0139722 A1 | 6/2012 | Wong et al. | 340/539.12 |
| 2012/0172685 A1 | 7/2012 | Gilbert | 600/306 |
| 2012/0253142 A1 | 10/2012 | Meger et al. | 600/301 |
| 2012/0253485 A1 | 10/2012 | Weast et al. | 700/91 |
| 2012/0259577 A1 | 10/2012 | Ganyi | 702/139 |
| 2012/0271654 A1 | 10/2012 | Croghan et al. | 705/3 |
| 2012/0277637 A1 | 11/2012 | Vahdatpour et al. | 600/595 |
| 2013/0006151 A1 | 1/2013 | Main et al. | 600/587 |
| 2013/0090571 A1 | 4/2013 | Nourani et al. | 600/587 |
| 2013/0096390 A1 | 4/2013 | Weller-Brophy | |
| 2013/0141233 A1 | 6/2013 | Jacobs | |
| 2014/0188638 A1 | 7/2014 | Jones et al. | 705/16 |
| 2014/0257057 A1 | 9/2014 | Reis Cunha et al. | 600/301 |
| 2014/0259414 A1 | 9/2014 | Hayes et al. | 5/611 |
| 2014/0313030 A1* | 10/2014 | Ten Kate | A61B 5/1115 340/539.12 |
| 2015/0011263 A1 | 1/2015 | Itamoto et al. | 455/566 |
| 2015/0082542 A1 | 3/2015 | Hayes et al. | 5/600 |
| 2015/0094618 A1* | 4/2015 | Russell | A61B 5/447 600/587 |
| 2015/0121261 A1 | 4/2015 | Collado et al. | 715/764 |
| 2015/0136146 A1 | 5/2015 | Hood et al. | 128/845 |
| 2015/0164437 A1 | 6/2015 | Mccombie et al. | 600/301 |
| 2015/0302539 A1 | 10/2015 | Mazar et al. | 705/3 |
| 2015/0351981 A1 | 12/2015 | Sazonov | 297/217.2 |
| 2016/0157798 A1 | 6/2016 | Anderson et al. | 600/427 |
| 2016/0256080 A1 | 9/2016 | Shen et al. | 600/595 |
| 2017/0027498 A1 | 2/2017 | Larson et al. | 600/595 |
| 2017/0055896 A1 | 3/2017 | Al-ali et al. | 600/301 |

FOREIGN PATENT DOCUMENTS

| | | | | |
|---|---|---|---|---|
| JP | 2003070768 A | 3/2003 | | A61B 5/107 |
| JP | 2003116858 A | 4/2003 | | A61B 10/00 |
| JP | 2004194709 A | 7/2004 | | A61G 7/00 |
| JP | 2004201758 A | 7/2004 | | A61B 5/00 |
| JP | 2006122376 A | 5/2006 | | A61B 5/22 |
| JP | 2006175206 A | 7/2006 | | A61B 5/107 |
| JP | 2006325683 A | 12/2006 | | A61B 5/00 |
| JP | 2008027030 A | 2/2008 | | A61B 5/00 |
| JP | 2008295644 A | 12/2008 | | A47C 21/00 |
| JP | 2010022723 A | 2/2010 | | A61B 5/028 |
| JP | 2010035579 A | 2/2010 | | A61G 12/00 |
| JP | 2011183121 A | 9/2011 | | A61B 5/11 |
| WO | 03/079898 A1 | 10/2003 | | A61B 5/00 |
| WO | 2007/106040 A1 | 9/2007 | | A61G 7/057 |
| WO | 2007/119070 A1 | 10/2007 | | A01K 11/00 |
| WO | 2008/113556 A1 | 9/2008 | | A61B 5/11 |
| WO | 2010/105045 A2 | 9/2010 | | A61B 5/02 |
| WO | 2010/105203 A2 | 9/2010 | | A61B 5/02 |
| WO | 2010/111363 A2 | 9/2010 | | A61B 5/103 |
| WO | 2011/087807 A2 | 7/2011 | | A61B 5/0059 |
| WO | 2011/113070 A1 | 9/2011 | | A61B 5/002 |
| WO | 2012/037470 A1 | 3/2012 | | G01C 21/00 |
| WO | WO-2012114298 A2 * | 8/2012 | | A61B 5/6892 |
| WO | 2013/042097 A1 | 3/2013 | | |
| WO | 2013/052123 A1 | 4/2013 | | A61B 5/103 |
| WO | 2013/109410 A1 | 7/2013 | | H04W 24/00 |
| WO | 2014/024094 A2 | 2/2014 | | A61G 7/057 |
| WO | 2015/054423 A1 | 4/2015 | | A61B 5/11 |

(56) References Cited

FOREIGN PATENT DOCUMENTS

| WO | 2015/074007 A1 | 5/2015 | ............... A61B 5/00 |
|---|---|---|---|
| WO | 2016/077310 A1 | 5/2016 | ............. G06Q 50/22 |

OTHER PUBLICATIONS

Papanikolaou, Panos et al., "Risk Assessment Scales for Pressure Ulcers: A Methodological Review," International Journal of Nursing Studies, vol. 44, pp. 285-296, Jan. 10, 2006.
U.S. Non-Final Office Action, U.S. Appl. No. 15/173,595, 14 pages, dated Dec. 4, 2018.
U.S. Final Office Action, U.S. Appl. No. 15/186,344, 20 pages, dated Jan. 3, 2019.
U.S. Non-Final Office Action, U.S. Appl. No. 14/244,720, 21 pages, dated Jan. 15, 2019.
U.S. Non-Final Office Action, U.S. Appl. No. 15/173,612, 54 pages, dated Jan. 17, 2019.
International Search Report and Written Opinion, Application No. PCT/US2018/041552, 12 pages, dated Oct. 4, 2018.
U.S. Non-Final Office Action, U.S. Appl. No. 15/654,928, 29 pages, dated Nov. 6, 2018.
Braden, Barbara et al., "Braden Scale—for Predicting Pressure Sore Risk," Form 3166P, 1 page, © 1988.
Halfens, R.J.G. et al., "Validity and Reliability of the Braden Scale and the Influence of other Risk Factors: A Multi-Centre Prospective Study," International Journal of Nursing Studies, vol. 37, pp. 313-319, Aug. 30, 1999.
Defloor, Tom, "The Effect of Position and Mattress on Interface Pressure," Applied Nursing Research, vol. 13, No. 1, pp. 2-11, Feb. 2000.
Keller, B.J. et al., "Pressure Ulcers in Intensive Care Patients: A Review of Risks and Prevention," Intensive Care Med, vol. 28, pp. 1379-1388, Sep. 7, 2002.
Lyder, Courtney H. et al., "Chapter 12. Pressure Ulcers: A Patient Safety Issue," In *Patient Safety and Quality: An Evidence-Based Handbook for Nurses*, Agency for Research and Quality, 33 Pages, Apr. 2008.
Peterson, M. et al., "Effects of Elevating the Head of Bed on Interface Pressure in Volunteers," Critical Care Medicine, vol. 36, No. 11, pp. 3038-3042, Nov. 2008.
Kraft, Peter et al., "Christmas 2009: Young and Old: Lying Obligquely—A Clinical Sign of Cognitive Impairment: Cross Sectional Obersvational Study," BMJ, vol. 339, 5 pages, Nov. 17, 2009.
Ostadabbas, Sarah et al., "Pressure Ulcer Prevention: An Efficient Turning Schedule for Bed-Bound Patients," IEEE/NIH Life Science Systems and Applications Workshop, pp. 159-162, 2011.
Cox, Jill, "Predictors of Pressure Ulcers in Adult Critical Care Patients," American Journal of Critical Care, vol. 20, No. 5, pp. 364-374, Sep. 2011.
Dhillon, Marshal et al., "Towards the Prevention of Pressure Ulcers with a Wearable Patient Posture Monitor Based on Adaptive Accelerometer Alignment," 34th Annual International Conference of the IEEE EMBS San Diego, CA, pp. 4513-4516, Aug. 28, 2012.
Japanese Office Action, Application No. 2012557312, 9 pages, dated Jan. 10, 2017.
U.S. Non-Final Office Action, U.S. Appl. No. 15/036,782, 28 pages, dated Mar. 29, 2017.
U.S. Non-Final Office Action, U.S. Appl. No. 14/244,720, 39 pages, dated Apr. 19, 2017.
U.S. Non-Final Office Action, U.S. Appl. No. 15/187,516, 42 pages, dated May 11, 2017.
U.S. Non-Final Office Action, U.S. Appl. No. 15/173,612, 38 pages, dated May 12, 2017.
European Invitation to Pay Additional Fees, Application No. 14862053. 7, 13 pages, dated May 23, 2017.
European Partial Supplementary Search Report, Application No. 14851948.1, 17 pages, dated Jun. 8, 2017.
International Search Report and Written Opinion, Application No. PCT/US2017/025832, 11 pages, dated Jun. 21, 2017.
U.S. Non-Final Office Action, U.S. Appl. No. 15/601,593, 31 pages, dated Aug. 15, 2017.
Invitation to Pay Additional Fees and Partial International Search Report, Application No. PCT/US2017/037589, 15 pages, dated Aug. 23, 2017.
European Extended Search Report, Application No. 14862053.7, 11 pages, dated Sep. 7, 2017.
U.S. Non-Final Office Action, U.S. Appl. No. 15/487,663, 26 pages, dated Sep. 14, 2017.
European Extended Search Report, Application No. 14851948.1, 13 pages, dated Sep. 19, 2017.
International Search Report and Written Opinion, Application No. PCT/US2017/038511, 12 pages, dated Oct. 5, 2017.
International Search Report and Written Opinion, Application No. PCT/US2017/037589, 19 pages, dated Oct. 16, 2017.
U.S. Final Office Action, U.S. Appl. No. 15/173,612, 51 pages, dated Nov. 14, 2017.
Japanese Office Action, Application No. 2016530839, 6 pages, dated Dec. 12, 2017.
U.S. Non-Final Office Action, U.S. Appl. No. 15/696,908, 28 pages, dated Dec. 22, 2017.
U.S. Non-Final Office Action, U.S. Appl. No. 15/654,928, 47 pages, dated Jan. 25, 2018.
U.S. Final Office Action, U.S. Appl. No. 15/487,663, 22 pages, dated Jan. 30, 2018.
European Extended Search Report, Application No. 17204228.5, 6 pages, dated Mar. 28, 2018.
U.S. Non-Final Office Action, U.S. Appl. No. 15/186,344, 23 pages, dated Apr. 6, 2018.
U.S. Final Office Action, U.S. Appl. No. 15/036,782, 57 pages, dated May 11, 2018.
Japanese Office Action, Application No. 2016530839, 4 pages, dated Jun. 12, 2018.
U.S. Non-Final Office Action, U.S. Appl. No. 15/173,595, 26 pages, dated Jul. 10, 2018.
U.S. Final Office Action, U.S. Appl. No. 15/654,928, 46 pages, dated Jul. 11, 2018.
U.S. Non-Final Office Action, U.S. Appl. No. 15/183,739, 25 pages, dated Aug. 9, 2018.
U.S. Final Office Action, U.S. Appl. No. 14/244,720, 80 pages, dated Aug. 13, 2018.
U.S. Non-Final Office Action, U.S. Appl. No. 13/070,189, 5 pages, dated Sep. 10, 2018.
U.S. Final Office Action, U.S. Appl. No. 15/696,908, 34 pages, dated Sep. 21, 2018.
Wang, Jue et al., "A Compound Sensor for Biomechanical Analyses of Buttock Soft Tissue in Vivo," Journal of Rehabilitation Research and Development, vol. 37, No. 4, pp. 433-443, Dec. 14, 1999.
Lowne, D.R., "Designing a Low-Cost Mattress Sensor for Automated Body Position Classification," IEEE Engineering in Medicine and Biology 27th Annual Conference, pp. 6437-6440, 2005.
DeFloor, Tom et al., "The Effect of Various Combinations of Turning and Pressure Reducing Devices on the Incidence of Pressure Ulcers," International Journal of Nursing Studies, vol. 42, No. 1, pp. 37-46, Jan. 2005.
Wai, A.A. et al., "Sleeping Patterns Observation for Bedsores and Bed-Side Falls Prevention," Annual International Conference of the IEEE Engineering in Medicine and Biology Society, pp. 6087-6090, 2009.
Hsia, C.C. et al., "Analysis and Comparison of Sleeping Posture Classification Methods using Pressure Sensitive Bed System," Annual International Conference of the IEEE Engineering in Medicine and Biology Society, pp. 6131-6134, Sep. 2009.
Yip, Marcus et al., "A Flexible Pressure Monitoring System for Pressure Ulcer Prevention," 31st Annual International Conference of the IEEE EMBS, Minneapolis, Minnesota, pp. 1212-1215, Sep. 2, 2009.
International Search Report and Written Opinion, Application No. PCT/US2012/00488, 6 pages, dated Jan. 23, 2013.
International Search Report and Written Opinion, Application No. PCT/US2014/066016, dated Feb. 11, 2015.
U.S. Non-Final Office Action, U.S. Appl. No. 15/028,018, 22 pages, dated Nov. 14, 2016.

(56) References Cited

OTHER PUBLICATIONS

U.S. Final Office Action, U.S. Appl. No. 14/244,720, 39 pages, dated Dec. 1, 2016.
U.S. Non-Final Office Action, U.S. Appl. No. 15/183,739, 18 pages, dated Jun. 28, 2019.
European Office Action, Application No. 17204228.5, 5 pages, dated Jul. 8, 2019.
U.S. Final Office Action, U.S. Appl. No. 14/244,720, 26 pages, dated Jul. 30, 2019.
European Office Action, Application No. 17204228.5, 5 pages, dated Jan. 29, 2019.
U.S. Final Office Action, U.S. Appl. No. 15/183,739, 30 pages, dated Feb. 19, 2019.
U.S. Non-Final Office Action, U.S. Appl. No. 15/189,086, 47 pages, dated Mar. 20, 2019.
Knox, Dorothy M. et al., "Effects of Different Turn Intervals on Skin of Healthy Older Adults," Advances in Wound Care, vol. 7, No. 1, pp. 48-56, Jan. 1994.
Anonymous, "By the Numbers: Braden Score Interventions," Advances in Skin & Wound Care, vol. 17, Nol. 3, p. 150, Apr. 2004.
DeFloor, Tom et al., "Pressure Ulcer Prevention and Repositioning," Science and Practice of Pressure Ulser Management, Chapter 8, pp. 67-73, 2006.
Vanderwee, K. et al., "Effectiveness of Turning with Unequal Time Intervals on the Incidence of Pressure Ulcer Lesions," Journal of Advanced Nursing, vol. 57, No. 1, pp. 59-68, Jul. 10, 2006.
Zijlstra, Wiebren et al., "Mobility Assessment in Older People: New Possibilities and Challenges," European Journal of Aging, vol. 4, pp. 3-12, Feb. 6, 2007.
U.S. Final Office Action, U.S. Appl. No. 15/654,928, 19 pages, dated May 10, 2019.
U.S. Non-Final Office Action, U.S. Appl. No. 13/070,189, 50 pages, dated May 15, 2019.
Seiler, Walter O. et al., "Decubitus Ulcers: Preventive Techniques for the Elderly Patient," Geriatrics, vol. 40, No. 7, pp. 53-60, Jul. 1985.
Seiler, Walter O. et al., "Influence of the 30° Laterally Inclined Position and the 'Super Soft' 3-Piece Mattress on Skin Oxygen Tension on Areas of Maximum Pressure—Implications for Pressure Sore Prevention," Gerontology, vol. 32, pp. 158-166, 1986.
Colin, Denis et al., "Comparison of 90° and 30° Laterally Inclined Positions in the Prevention of Pressure Ulcers Using Transcutaneous Oxygen and Carbon Dioxide Pressures," Advances in Wound Care, vol. 9, No. 3, pp. 35-38, 1996.
DeFloor, Tom, "The Risk of Pressure Sores: A Conceptual Scheme," Journal of Clinical Nursing, vol. 8, pp. 206-216, May 10, 1998.
Okuwa, Mayumi et al., "Measuring the Pressure Applied to the Skin Surrounding Pressure Ulcers while Patients are Nursed in the 30° Position," Journal of Tissue Viability, vol. 15, No. 1, pp. 3-8, Jan. 2005.
Scanaill, Cliodhna Ni et al., "A Review of Approaches to Mobility Telemonitoring of the Elderly in Their Living Environment," Annals of Biomedical Engineering, vol. 34, No. 4, pp. 547-563, Mar. 21, 2006.
U.S. Final Office Action, U.S. Appl. No. 15/173,612, 32 pages, dated Aug. 22, 2019.
U.S. Final Office Action, U.S. Appl. No. 15/189,086, 19 pages, dated Aug. 28, 2019.
Japanese Office Action, Application No. 2018169327, 12 pages, dated Sep. 9, 2019.
U.S. Non-Final Office Action, U.S. Appl. No. 15/696,908, 43 pages, dated Oct. 2, 2019.
Lalonde, N. M. et al., "Effect of Different Tilt and Seat-To-Back Angles on Trunk, Pelvic, and Hip Orientations," Proceedings of the 22nd Annual RESNA Conference, 9 pages, Jun. 25, 1999.
Shabshin, Nogah et al., "Evaluation of the Effect of Trunk Tilt on Compressive Soft Tissue Deformations Under the Ischial Tuberosities Using Weight-Bearing MRI," Clinical Biometrics, vol. 25, Issue 5, pp. 402-408, Jan. 28, 2010.
U.S. Final Office Action, U.S. Appl. No. 15/696,908, 23 pages, dated Mar. 5, 2020.
U.S. Non-Final Office Action, U.S. Appl. No. 15/189,086, 23 pages, dated Mar. 13, 2020.
U.S. Non-Final Office Action, U.S. Appl. No. 14/244,720, 24 pages, dated Mar. 19, 2020.
Lord, M. et al., "Rehabilitation Engineering: Method for In-Shoe Shear Stress Measurement," Journal of Biomedical Engineering, vol. 14, pp. 181-186, May 1992.
Mimura, Maki et al., "Mechanism Leading to the Development of Pressure Ulcers Based on Shear Force and Pressures During a Bed Operation: Influence of Body Types, Body Positions, and Knee Positions," Wound Repair and Regeneration, vol. 17, pp. 789-796, Jul. 27, 2009.
U.S. Final Office Action, U.S. Appl. No. 13/070,189, 27 pages, dated Nov. 29, 2019.
European Office Action, Application No. 17204228.5, 4 pages, dated Dec. 20, 2019.
U.S. Non-Final Office Action, U.S. Appl. No. 15/423,665, 13 pages, dated Jan. 10, 2020.
U.S. Non-Final Office Action, U.S. Appl. No. 15/173,612, 23 pages, dated Jan. 15, 2020.
U.S. Non-Final Office Action, U.S. Appl. No. 16/548,553, 22 pages, dated Aug. 28, 2020.
U.S. Non-Final Office Action, U.S. Appl. No. 15/935,385, 26 pages, dated Jul. 15, 2020.
U.S. Non-Final Office Action, U.S. Appl. No. 16/380,811, 27 pages, dated Jun. 23, 2020.
Japanese Office Action, Application No. 2019159408, 7 pages, dated Jul. 20, 2020.
U.S. Final Office Action, U.S. Appl. No. 15/189,086, 23 pages, dated Aug. 10, 2020.
U.S. Final Office Action, U.S. Appl. No. 14/244,720, 17 pages, dated Aug. 10, 2020.
U.S. Non-Final Office Action, U.S. Appl. No. 15/189,086, 40 pages, dated Dec. 16, 2020.
U.S. Non-Final Office Action, U.S. Appl. No. 16/820,403, 27 pages, dated Dec. 24, 2020.
U.S. Final Office Action, U.S. Appl. No. 15/935,385, 28 pages, dated Feb. 8, 2021.
European Extended Search Report, Application No. 20206825.0, 7 pages, dated Jan. 14, 2021.

* cited by examiner

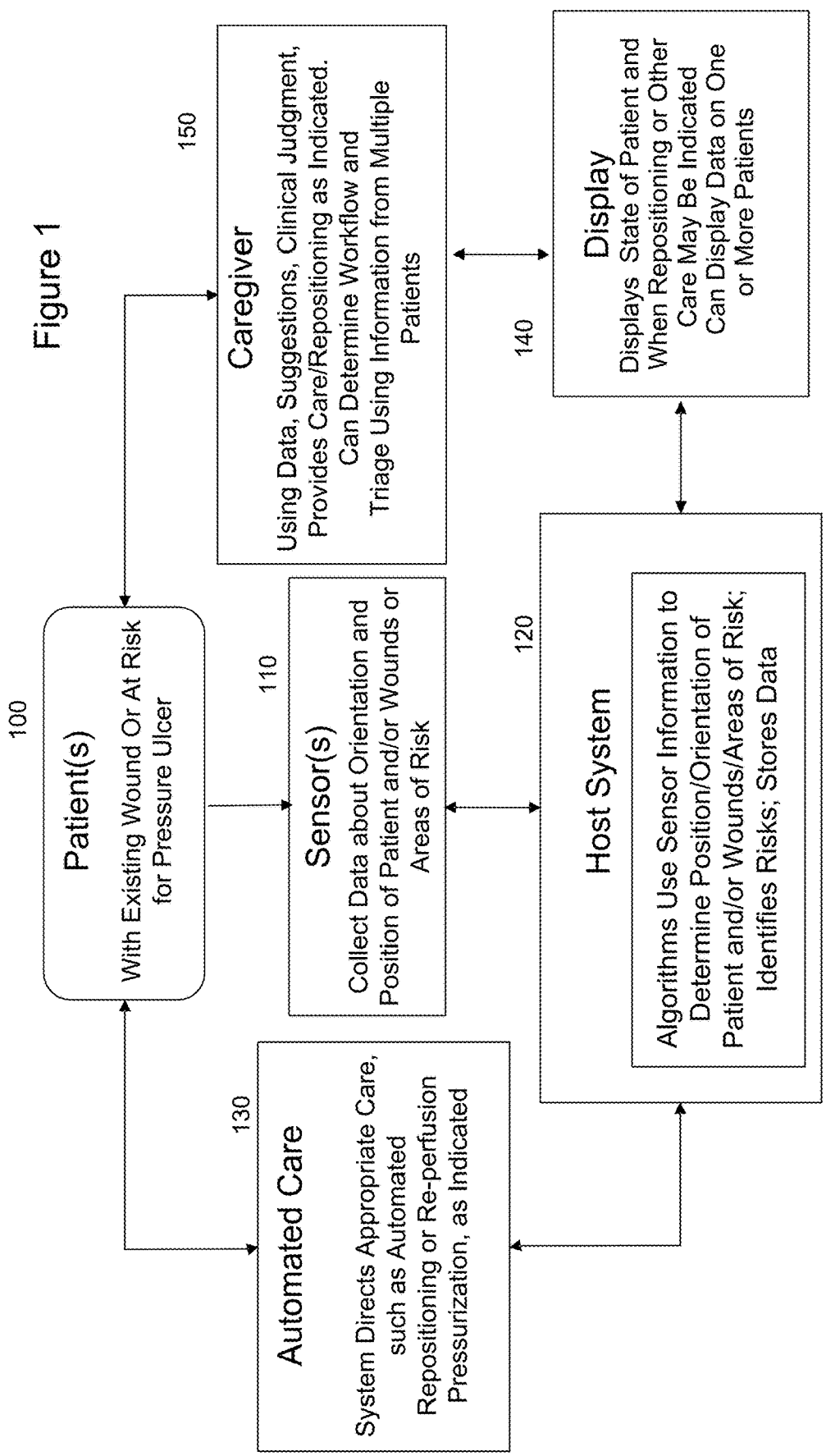

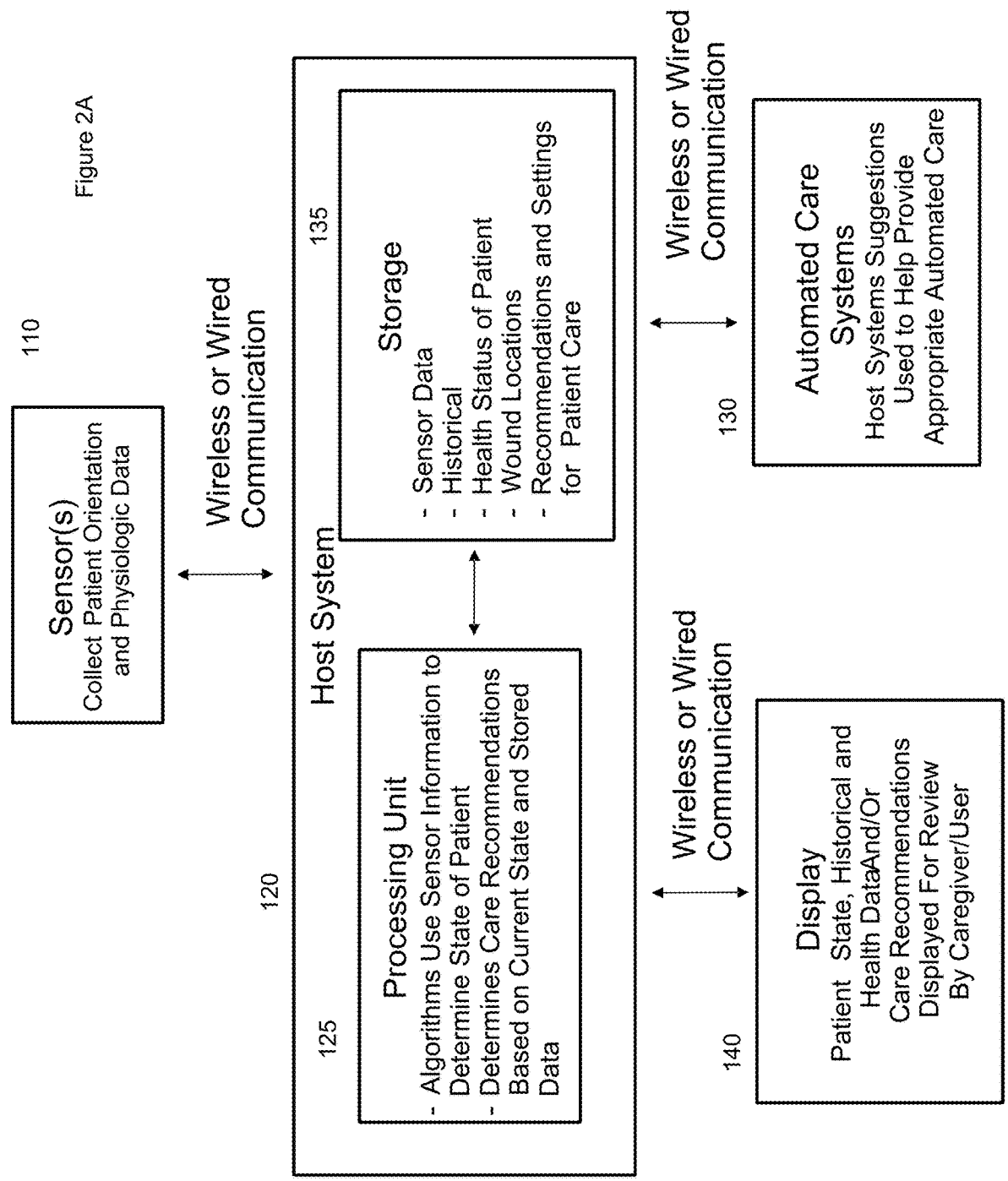

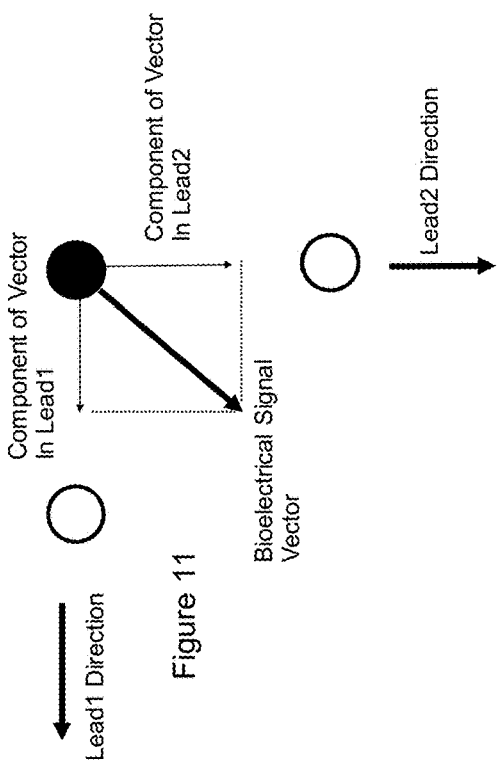
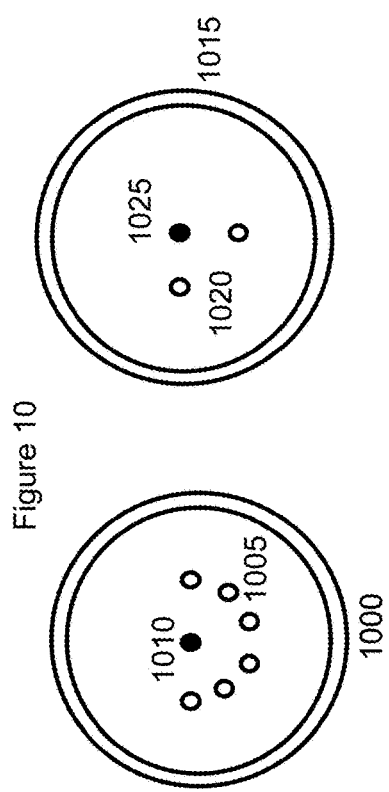
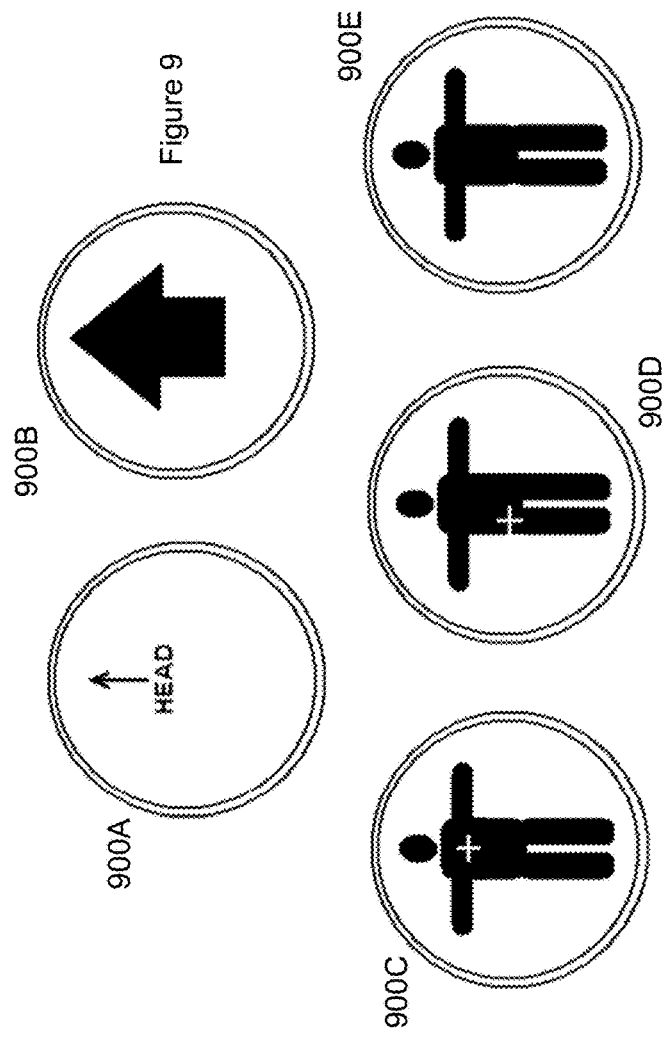

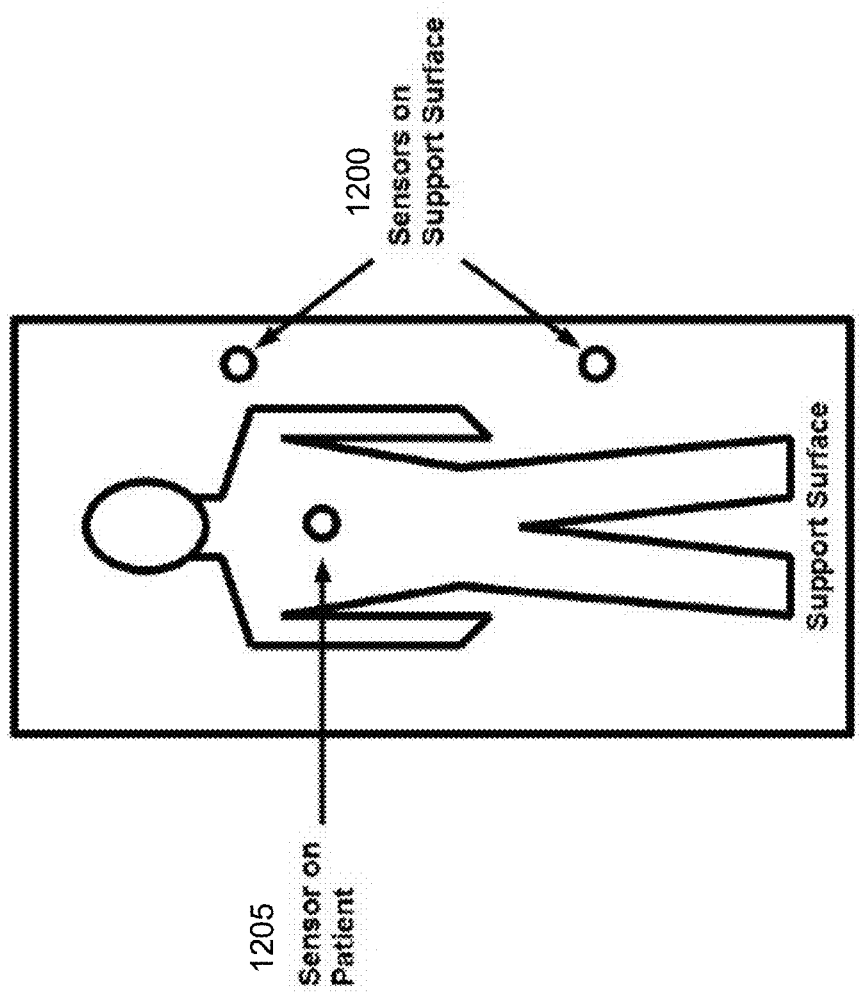

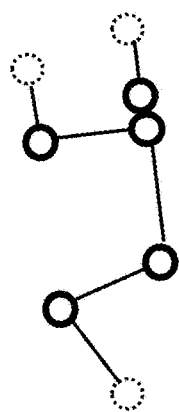
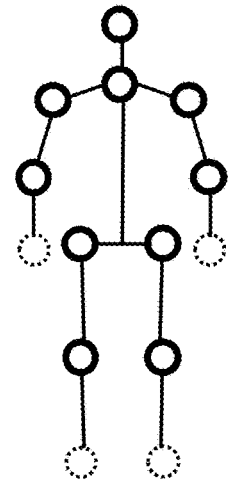
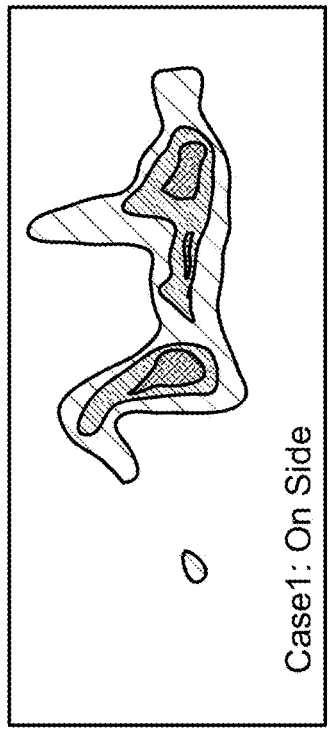
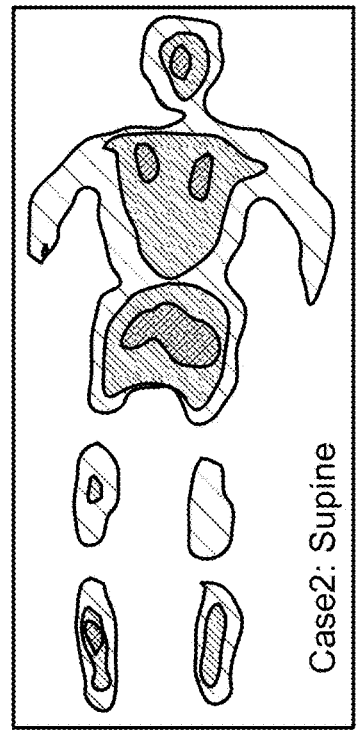
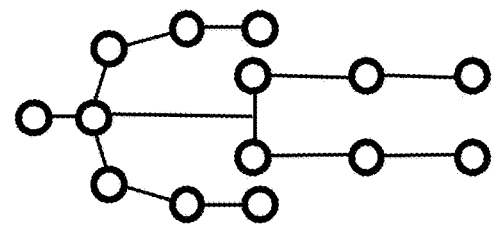
Figure 19

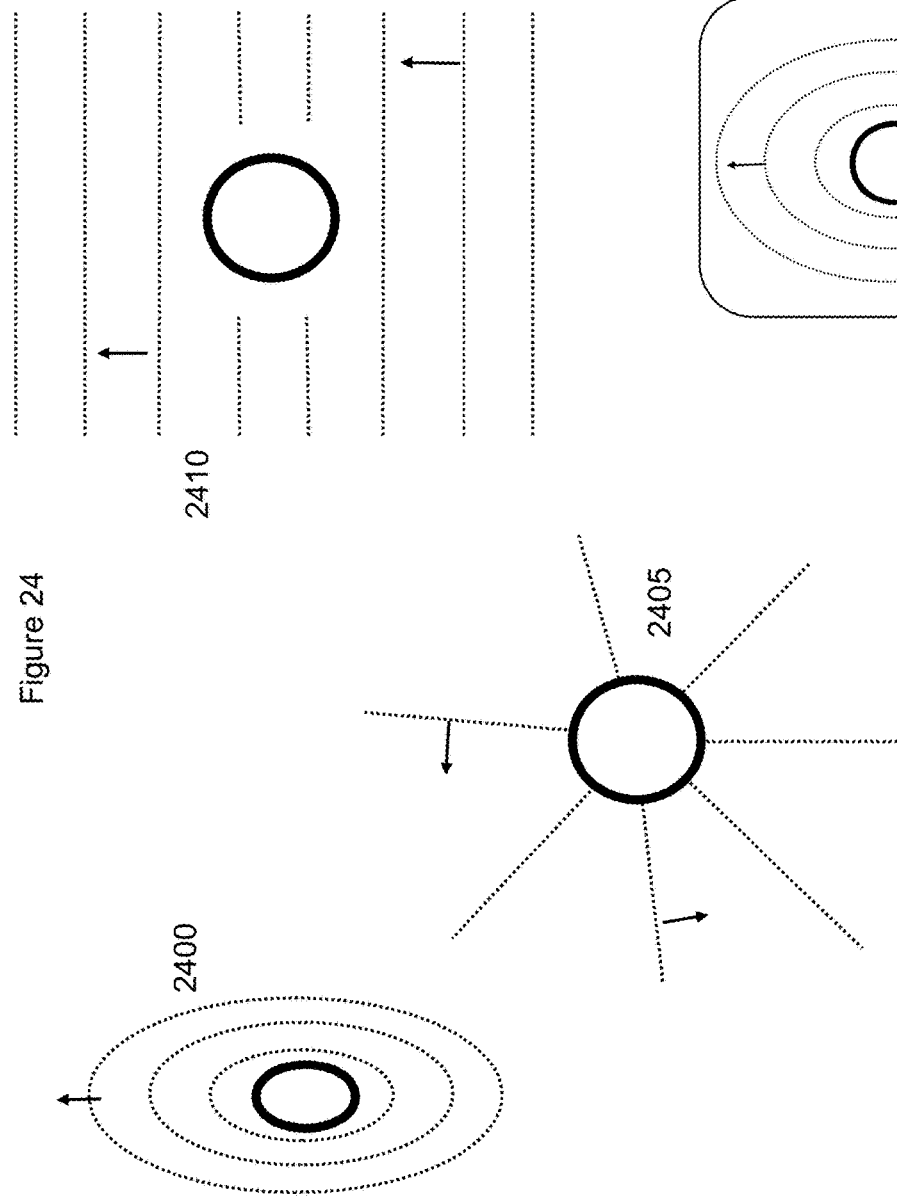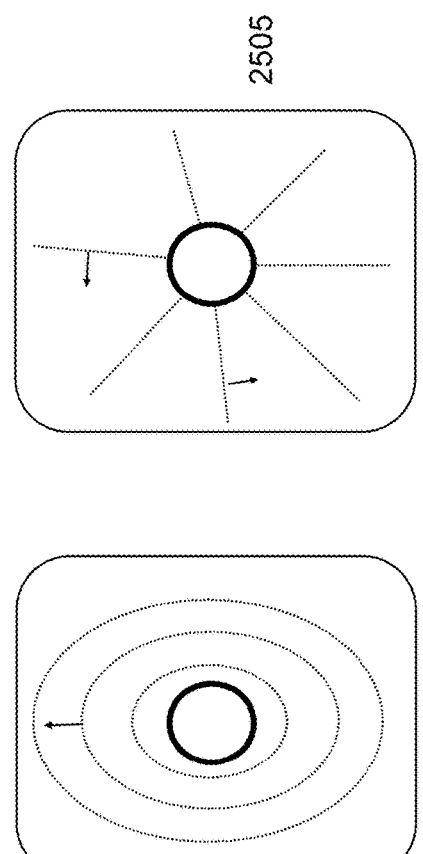
Figure 24
Figure 25

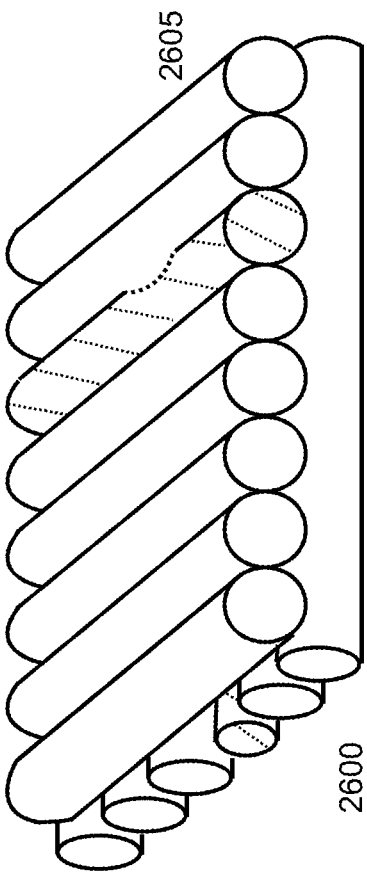
Figure 26
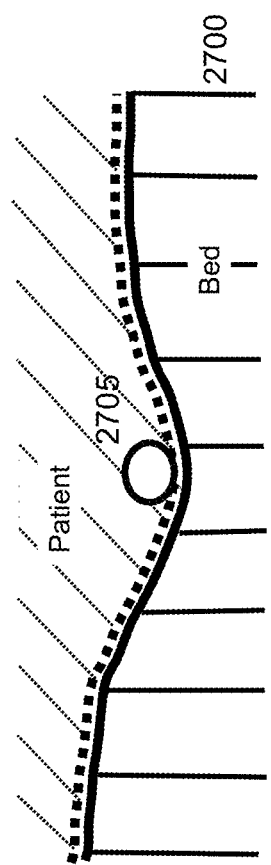
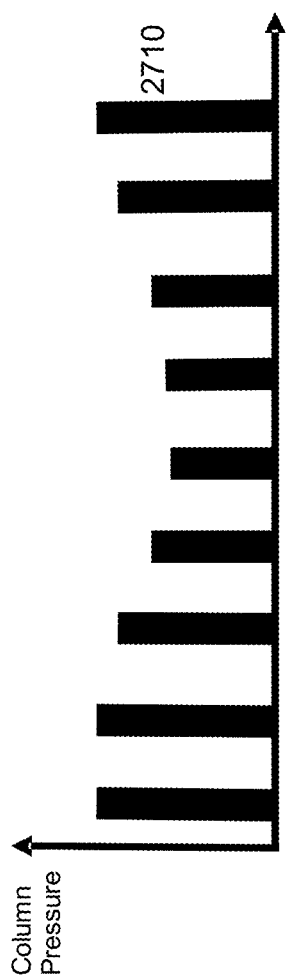
Figure 27

CALIBRATED SYSTEMS, DEVICES AND METHODS FOR PREVENTING, DETECTING, AND TREATING PRESSURE-INDUCED ISCHEMIA, PRESSURE ULCERS, AND OTHER CONDITIONS

RELATED APPLICATIONS

The present application is a divisional of, and claims the benefit under 35 USC Section 119 of U.S. patent application Ser. No. 13/070,189, filed Mar. 23, 2011, and through it further claims the benefit of the following applications: U.S. provisional Patent Application Ser. No. 61/438,732, filed Feb. 2, 2011, entitled System for Optimizing Patient Turning; provisional Patent Application Ser. No. 61/326,664, filed Apr. 22, 2010, entitled Methods and Devices that Enable the Sensing of Body Surface Markers for the Prevention and Treatment of Pressure Ulcers and Other Wounds; provisional Patent Application Ser. No. 61/411,647, filed Nov. 9, 2010, entitled Method and Device for Surface Pressure Monitoring; provisional Patent Application Ser. No. 61/393,364, filed Oct. 15, 2010, entitled Patient Position, Orientation, and Surface Pressure Monitoring Device; and provisional Patent Application Ser. No. 61/373,260, filed Aug. 12, 2010, entitled Sensing System that Automatically Identifies and Tracks Body Surface Markers to Allow for the Delivery of Targeted Therapy. The foregoing applications are all incorporated herein by reference for all purposes.

FIELD OF THE INVENTION

Aspects of the present invention relate generally to systems, devices and methods for the detection of compromised tissue perfusion and other issues affecting the health of a patient, and more particularly relates to systems, devices and methods for such detection, communicating of relevant information to a host, and providing either appropriate guidance to a caregiver to facilitate proper management of the patient or device instructions for providing automated care.

BACKGROUND OF THE INVENTION

The management of pressure ulcers poses a substantial burden to the healthcare system. Each year, the United States spends billions of dollars treating pressure ulcers and associated complications. Pressure ulcers are very common and they represent a significant source of morbidity and mortality for patients. The prevalence of pressure ulcers in the US alone is estimated to be between 1.5 and 3.0 million people, with two thirds of cases involving patients 70 or older.

Pressure ulcers, which are also known as pressure sores, bed sores, or decubitus ulcers, represent localized areas of tissue damage. Pressure ulcers often occur when the soft tissue between a bony prominence and an external surface is compressed for an extended period of time. Pressure ulcers can also occur from friction, such as by rubbing against a bed, cast, brace, or the like. Pressure ulcers commonly occur in immobilized patients who are confined to a bed, chair or wheelchair. Localized tissue ulceration results when pressure on the skin exceeds capillary filling pressure (approximately 32 mm Hg), which thereby impedes the microcirculation in the skin and the underlying subcutaneous tissue. With compromised blood flow, the delivery of oxygen and nutrients to target tissues is impaired. If blood flow is not restored promptly, the skin and subcutaneous tissue will die and a pressure ulcer will develop.

Pressure ulcers will initially appear as areas of red or pink skin discoloration, but these areas can quickly develop into open wounds if left untreated. Open wounds can lead to severe health complications by exposing patients to life-threatening infections. The primary goal in the treatment and prevention of pressure ulcers is to relieve pressure on and around affected tissues. Pressure relief can be accomplished by frequently changing the position of immobilized patients and by using support surfaces that minimize surface pressure. Although pressure management is the most critical aspect of any successful treatment program, it is also important to ensure that patients receive adequate nutrition, engage in daily exercise, and follow a good skin care and personal hygiene protocol.

A Braden score is commonly used by caregivers to assess a patient's risk for developing a pressure ulcer. The Braden scale is composed of six criteria, which when taken together, can be used to estimate a patient's likelihood of ulceration and can also be used to determine the level of pressure ulcer prevention procedures required for a specific patient. The six components of the Braden scale are: sensory perception, moisture, activity, mobility, nutrition, and friction/shear forces. Each component is rated on a scale of 1 to 4, with the exception of friction/shear which is rated on a scale of 1 to 3. The maximum score is 23, and higher scores reflect a lower risk of developing pressure ulcers. In general, patients with a Braden score of less than 18 are considered to be at high-risk for developing a pressure ulcer.

Various devices and methods for treating and preventing pressure ulcers have been developed. The cornerstone of pressure ulcer prevention is to turn patients on a regular basis, such as every one or two hours. Patients confined to a wheelchair, chair, or other surface should be moved in such a manner. Intermittent relief of surface pressure has proven to be highly effective in preventing the development of pressure ulcers. However, various factors limit compliance with turning/repositioning protocols.

Alarm systems have been developed to help improve compliance with patient turning/repositioning protocols. Generally, these alarms are triggered when the system detects an inadequate amount of patient movement over a predefined time interval. Movement can be detected using various modalities, which include vibration sensors, pressure sensors, and video cameras. Although these systems can detect patient movement, they cannot reliably determine if the perceived movement resulted in adequate depressurization from specific regions of the body.

Also, current alarm systems cannot compute the cumulative pressure-time index (or pressure dose) at specific regions of the body. Although some alarm systems have been designed to measure the surface pressure distribution over a support surface, they are unable to directly correlate the measured pressure with discrete regions of a patient's body. For example, although a pressure sensitive mat placed under a patient can measure the overall surface pressure, it cannot automatically and directly measure the surface pressure at discrete regions of the body, nor can it directly track the cumulative pressure dose at specific regions of the body over time. Furthermore, pressure sensitive mats cannot easily and robustly distinguish between pressure resulting from patient contact with the support surface vs. pressure resulting from non-patient contact with support surface (i.e. books, food trays, etc.).

In addition to turning regimens, pressure ulcer prevention and management also commonly involves the use of pressure reducing support surfaces, which are well known in the art. Such support surfaces attempt to minimize the overall surface pressure and some support surfaces, such as alternating-pressure mattresses, are designed to modulate the surface pressure as a function of time. Although it is desirable to minimize the overall surface pressure, it is important to recognize that different regions of the body have different surface pressure thresholds.

For example, areas underlying bony prominences, such as the hips and sacrum, have relatively low surface pressure thresholds, which is why pressure ulcers commonly occur at these locations. Support surfaces are currently not able to detect or differentiate among specific regions of a patient's body. Without this detection ability, support surfaces are not able to selectively modulate surface pressure at specific regions of a patient's body. Also, current support surfaces cannot automatically identify areas of compromised tissue perfusion, so they are unable to automatically redistribute pressure away from ischemic areas.

There is a long-felt, definite and even urgent need for a system, method, and device that helps to prevent, detect, and/or treat pressure-induced ischemia and pressure ulcers by optimizing surface pressure at areas of compromised tissue perfusion. Various aspects of the present invention accomplish these objectives and substantially depart from the conventional concepts and designs of the prior art.

SUMMARY OF THE INVENTION

The present invention overcomes the limitations of the prior art by providing systems, methods and devices for patient management, including the detection, treatment and prevention of wounds such as pressure ulcers, among other things, and conditions likely to cause such wounds. Furthermore, the present invention provides communication from one or more sensors monitoring a patient to a host system to alert caregivers to key conditions and to enable an improved, more reliable method for patient care. Alternatively, the host system can initiate an automated care event. Some aspects of the present invention relate to sensing systems that locate sites of compromised tissue perfusion or tissue injury and substantially optimize surface pressure at those locations.

Other aspects of the present invention relate to sensing systems that provide information regarding the position, orientation, and/or movements of a patient, and allow for surface pressure optimization based on this information. Here the position refers to the shape that the body takes independent of orientation, for example, knees bent, back straight, arms above head. The orientation refers to direction that the body is facing and the angle, for example, supine, prone, rotated left, rotated right, tilted Trendelenburg, tilted reverse Trendelenburg, etc. Movement refers to changes in either position, location, or orientation, achieved by bending, translating, or turning, respectively. Such sensors can be placed directly on the body, or on or in the support surface, or on or in clothing worn by the patient, or can be sensors capable of monitoring patients from more remote locations. In a presently preferred arrangement, a sensor comprising a multi-axial accelerometer provides data representative of patient position, orientation, and movement, which is then processed by a host system, which can be remote from the sensor, as described hereinafter Other aspects of the invention provide techniques for selectively modulating surface pressure at and around sites of compromised tissue perfusion, or sites of tissue injury, or sites considered to be at risk for developing tissue injury or sites where pressure is not desirable, thus substantially eliminating at least some of the conditions likely to lead to the formation of pressure ulcers, as well as aiding in the treatment of pressure ulcers and other wounds.

Still other aspects of the present invention comprise the use of body surface markers together with systems and techniques for optimizing surface pressure at locations corresponding to such body surface markers. For example, body surface markers can be placed over areas of damaged tissue or areas thought to be at high-risk for developing pressure sores (i.e. hips, heels, sacrum, etc). The support system can then attempt to focus pressure-relieving maneuvers at and around these locations. Body surface markers can include, but are not limited to, the following: stickers, wound dressings, socks, undergarments, and sensible ink or other media, films, or adhesives. Depending upon the implementation, body surface markers can be comprised of anything that has at least one sensible property that is in some way distinguishable from the patient by a host system. As used herein, "sensible" means "capable of being sensed." In at least some embodiments of the present invention, pressure distribution over time and location is then selectively optimized with respect to the body surface markers in an effort to optimize tissue perfusion.

Still further aspects of the present invention are configured to minimize or eliminate physical contact with injured tissue, areas of compromised tissue perfusion, areas identified to be at-risk for compromised tissue perfusion, or areas corresponding to body surface markers. An objective of an embodiment of the present invention is to control the surface pressure at sites of tissue injury, sites identified as having compromised tissue perfusion, or sites corresponding to body surface markers. These aspects of the invention allow for increased blood circulation and increased airflow to critical areas, thus promoting the healing of existing pressure ulcers and preventing the formation of other pressure ulcers.

THE FIGURES

FIG. 1 illustrates in block diagram form an embodiment of a system in accordance with one aspect of the invention in which one or more sensors provide to a host data representative of a patient's position, orientation, and movement, and the host uses that information, together with other patient information, to identify risks with respect to either avoidance or treatment of pressure ulcers on the patient, among other things.

FIG. 2A illustrates in block diagram form an embodiment of the hardware of a system in accordance with one aspect of the invention.

FIG. 9 illustrates a variety of indices applied to the sensor of FIG. 3 for ensuring proper location and orientation on the patient.

FIG. 10 illustrates two arrangements of electrodes for the sensor of FIG. 3, the first comprising seven electrodes including common, and the second comprising three electrodes including common.

FIG. 11 illustrates an electrode orientation by which only two electrodes are required when spaced at a known angle.

FIG. 12 illustrates the use of sensors placed both on the patient and the support surface that can be used to determine orientation relative to the support surface.

FIG. 19 illustrates how a system and algorithms can use a model of the human body and how the body moves in addition to a pressure map to determine an estimate of the orientation and positioning of a patient.

FIG. 24 illustrates patterns of pressure wave motion in reference to a marker.

FIG. 25 illustrates patterns of pressure wave motion as in FIG. 24 but applied to a smaller pressure modulating surface.

FIG. 26 illustrates a matrix of horizontal pressurized rows in two non-collinear orientations that can be pressurized or depressurized to target pressure optimization to a particular location or coordinate within the matrix.

FIG. 27 illustrates a gradient of pressure change, in contrast to a more sudden pressure change, that is created in the support surface in response to a sensed marker, as represented by the star.

DETAILED DESCRIPTION OF THE INVENTION

Figure 2B:
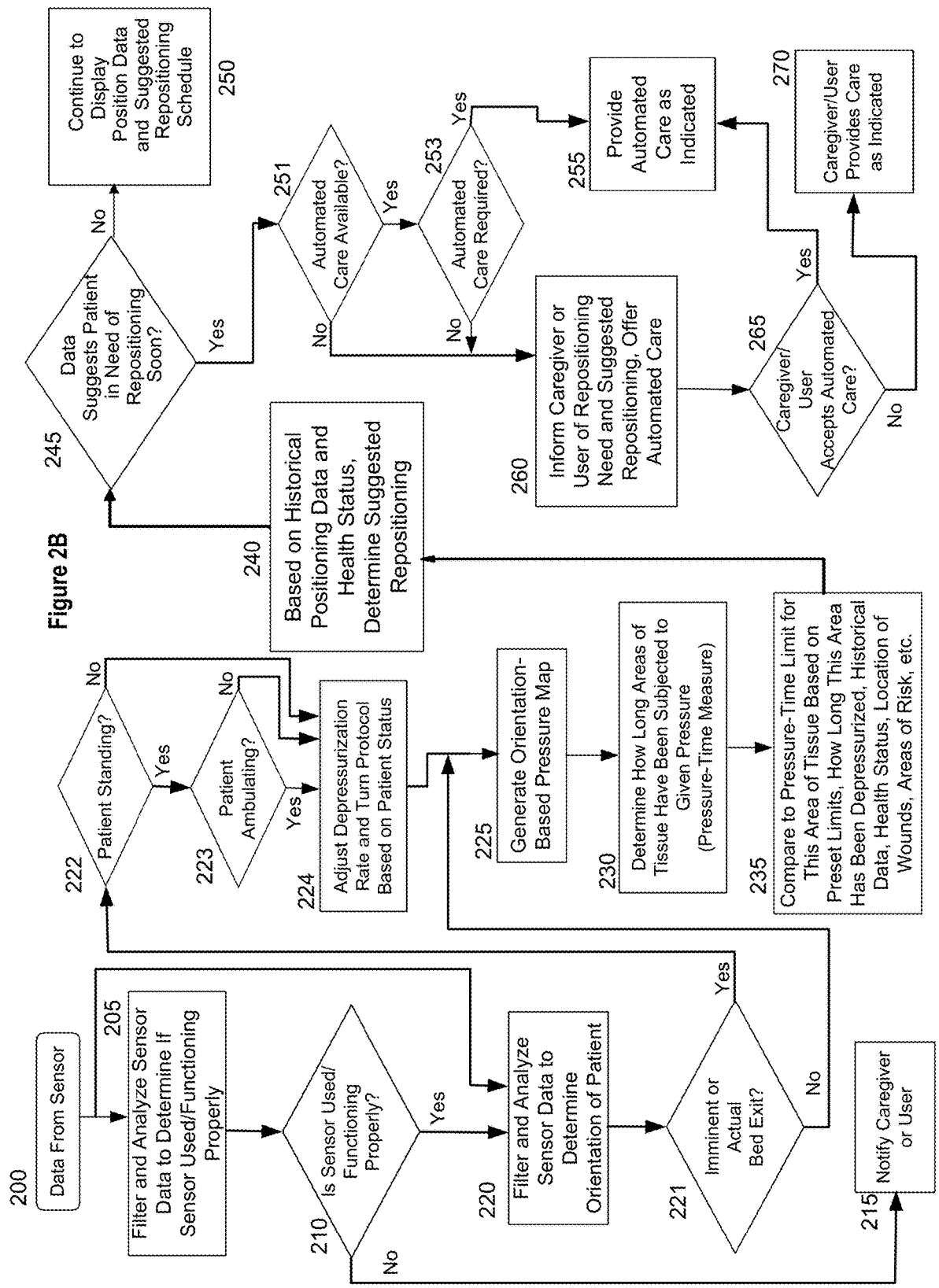
FIG. 2B illustrates in flow diagram form an embodiment of the process flow for comparing new sensor data from a patient with historical patient information for the purpose of preventing or treating pressure ulcers on the patient, and capable of running on the system of FIG. 2A.

Referring first to FIG. 1, an embodiment of a system in accordance with an aspect of the invention is illustrated in flow diagram form. A patient 100 requiring monitoring, and in at least some instances having an existing wound or being at risk for developing a pressure ulcer, is associated with one or more sensors 110. The sensors collect data about the orientation, position, and movement of the patient and/or wounds and/or areas of compromised tissue perfusion and/or areas of risk. The sensors communicate with a host system 120, typically a computer running at least one program for processing the incoming sensor information to determine the position or orientation or movements of a patient, wounds or areas of compromised tissue perfusion or areas of risk on the patient. The program also uses historical and other data to analyze the sensor data and identify risks. In at least some embodiments, the data, including both the sensor data and the analytical data, is stored for future use.

Depending upon the embodiment, the output of the host system can provide direction to an automated care system, as shown at 130, or can display messages for the attention of a caregiver as shown at 140. In the latter instance, the caregiver uses the suggestions from the system together with training and judgment and makes a determination regarding management of a patient's care, as shown at 150.

Referring next to FIG. 2A, an embodiment of the hardware components of the system of FIG. 1 can be better appreciated. More specifically, the sensors 110, a variety of which are described in greater detail hereinafter, collect patient orientation and physiologic data. In some instances, this can include heart rate, respiratory rate, and other data in addition to patient orientation, position, and movement. The host system 120 typically comprises a processing unit 125 together with at least one data storage device. The processing unit executes one or more software programs to analyze the sensor information and determine the state of the patient, to determine care recommendations based on the current state of the patient and relevant stored data, and, in some instances directs the operation of an automated care system 130. The data store 135 typically comprises a hard disk, RAM, EEPROM, solid state disk, or other memory device, and stores current and historical sensor data, health status of the patient, wound locations if any, at risk locations if any, as well as recommendations and settings for patient care. In some systems, the data store can be integrated with or linked to one or more of the hospital's databases, such that data in the data store 135 is updated whenever the hospital records are updated. The host system 120 communicates by either wired or wireless links with the display 140 and/or one or more automated care systems 130.

Referring next to FIG. 2B, the operation of the software component of the system of FIG. 1 and FIG. 2A can be better appreciated. Data 200 from the sensor is initially filtered and analyzed, as shown at step 205, to determine if the sensor is both used and functioning properly. That determination is made at step 210; if the sensor is not functioning properly, a notice about the deficiency is sent at step 215. However, if the sensor is functioning properly, the process continues at step 220, where the raw sensor data is filtered and analyzed to determine the orientation of the patient. Next, at steps 221-223, a check is made to determine whether the patient has exited the bed, or is in a position to imminently exit the bed, or is standing, or is ambulating. Such checks can be made as described in co-pending U.S. patent application Ser. No. 14/543,887, filed 17 Nov. 2014 and incorporated herein by reference. Sensing modalities that can be used to make such determinations include one or more of accelerometers, magnetometers, altimeters, and general location sensing techniques (i.e. triangulation and sensor position localization), each used singly or in multiples.

In the event that the patient is either about to exit the bed, or has exited the bed to stand, or is out of the bed and ambulating, an adjustment to the pre-existing turn protocol is appropriate in some embodiments. In each instance, the patient either is not or soon will not be supported by the support surface. Two adjustments may be appropriate to the turn protocol, depending upon the embodiment. First, the patient does not need to be turned, and, second, the tissues that were recently pressurized when the patient was on the support surface will now start to depressurize. Further, the rate of such depressurization will typically exceed the rate of depressurization if the patient had remained on the support surface and been turned as described herein. This faster rate of depressurization occurs because: 1) the body tissues are not under any pressure from a support surface, 2) the cardiac output is likely increased with ambulation and thus tissue perfusion is improved relative to a sedentary patient, and 3) patients that are ambulatory are generally at lower risk for pressure ulcers and thus require a less stringent turning protocol.

In some implementations, detection of ambulation (or standing) is cause to immediately reset the turn clock and amend patient history to reflect immediate depressurization of all body tissues. In other implementations, detection of ambulation (or standing) will cause the body tissues to depressurize at an accelerated rate; that is, the depressurization will take much less time. For example, if tissues depressurize at a rate of 1× when on a support surface, the same tissue may depressurize at a rate of 2× upon ambulation. The adjustment to depressurization rate or time can be varied based on patient-specific data, or can be a fixed value, or any other suitable arrangement, and the turn protocol is adjusted to reflect the need [or lack thereof] for a current turn as well as the change in depressurization rate. Patient-specific data related to such adjustments can be, for example, how often the patient exits the bed, how long they stand, how far and how quickly they ambulate, falls or a lack thereof when out of bed. A patient who exits the bed once a week for a few steps may be assigned a different depressurization rate or time, and turn protocol, than a patient who ambulates daily for 100 feet.

In some embodiments, detection of ambulation (or standing) is cause to temporarily disable, suspend, or otherwise discontinue the patient's turning schedule. When a patient is not supported on a support surface, there is no need for the patient to be turned or repositioned and therefore the turning protocol (and all associated alerts/notifications) can temporarily be suspended. As soon as it is determined that the patient has returned to a support surface, the turning protocol (and all associated alerts/notifications) can be resumed. In some embodiments the amount of depressurization that has occurred while the turn protocol has been suspended can be taken into account when the turn protocol is resumed.

If the patient is not about to exit the bed, nor standing, nor ambulating, the process advances directly to step 225 with no adjustments to the depressurization rate or the existing turn protocol. If an adjustment has been made at step 242, the process advances to step 225 with that adjustment implemented for the further steps.

Then, at step 225, an orientation-based pressure map is generated, followed at step 230 by a pressure-time determination to assess how long areas of tissue have been subjected to a given pressure. A time input can be derived from the host 120, or a separate time base can be used to make the pressure-time measurement. Then, at step 235, the pressure-time measurement is compared to a preset limit, and, together with historical data, how long the area has been depressurized, when the most recent depressurization of the area occurred, health conditions of patient, location of wounds, areas of risk, and other factors, together with historical positioning data as shown at step 240, a determination is made regarding suggested repositioning.

Then, at step 245, a determination is made as to whether the data suggests that the patient should be repositioned soon. If no, the process ends at step 250, with, in some embodiments, the display of orientation, position, and movement data and a suggested repositioning schedule. If yes, and an automated care function exists as checked at 251 and is required as checked at 253, the decision at step 245 results in a directive to provide automated care at step 255. Alternatively, or in the event that automated care is not successful or is not required, a message is sent to a caregiver at step 260 advising of the need for repositioning, as well as a suggested new position. In the event automated care is available to the caregiver as an option, the caregiver either accepts the suggestion, indicated at 265, or provides alternate care at step 270 based on judgment and training.

An aspect of the present invention is the sensor itself. Acceptable sensors for the system of the present invention can vary widely, and include sensors both in continuity with the patient's body or remote to the patient's body. Possible sensors include accelerometers, RFID sensing, resistive, capacitive, inductive and magnetic sensors, reflective sensors, infrared sensors, video monitoring, pressure and stress sensors, transcutaneous oxygen pressure sensors, transcutaneous $CO_2$ sensors, hydration sensors, pH sensors, ultrasound sensors, remote optical spectroscopy sensors, and laser Doppler flow sensors, among others.

Figure 3:
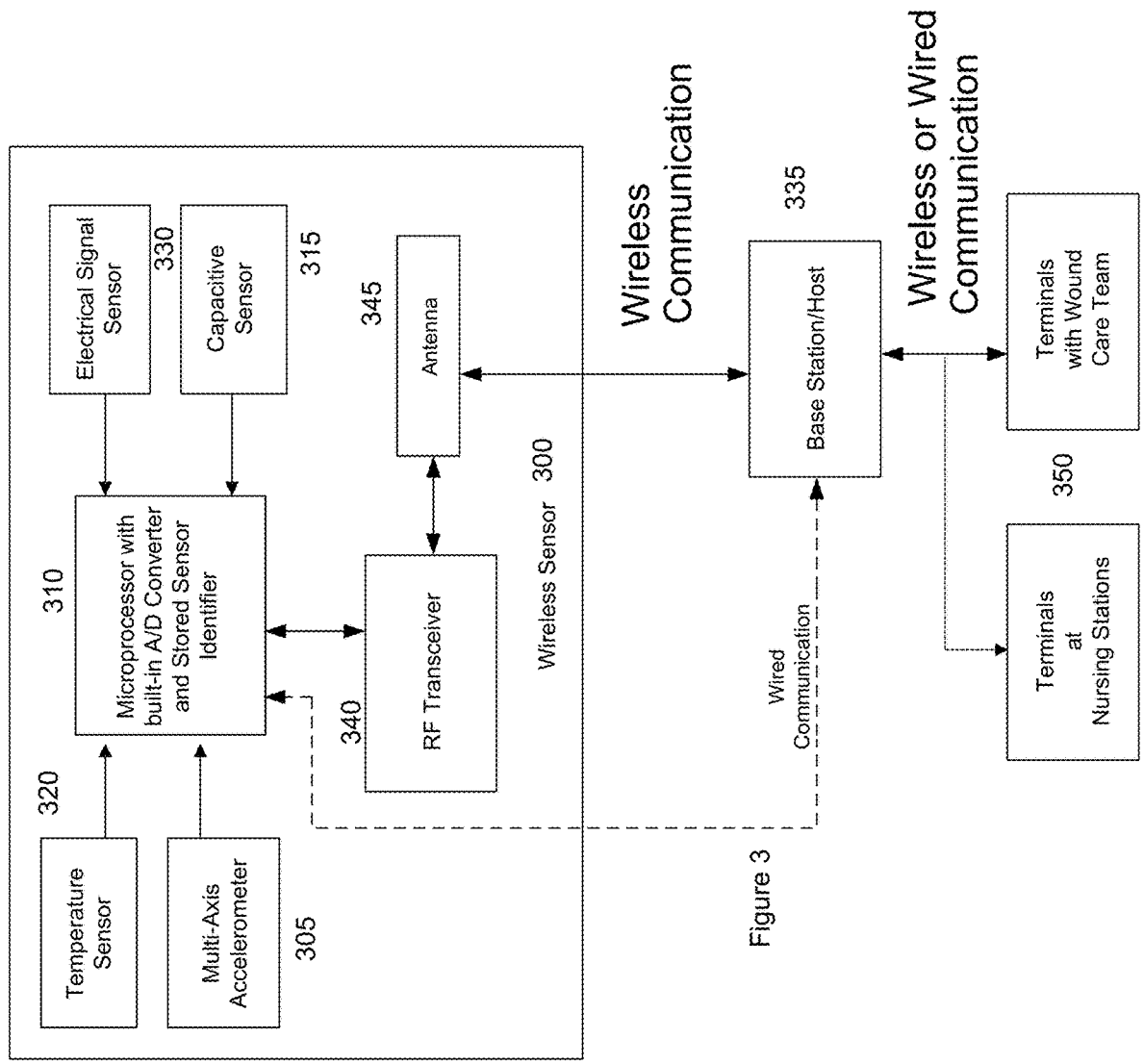
FIG. 3 illustrates an accelerometer-based sensor in accordance with one aspect of the invention.

As shown in FIG. 3, one presently preferred form of a sensor comprises a multi-axial accelerometer 305 with associated processor 310 and related electronics, as shown in FIG. 3, and generally indicated by 300. One acceptable accelerometer is the type LIS344ALH three axis accelerometer available from ST Microelectronics, although sensing on three axes is not required in all embodiments. In addition to the accelerometer, the sensor 300 can also comprise a capacitive sensor 315, a temperature sensor 320, a moisture sensor 325, and an electrical signal sensor 330. The microprocessor 310 can comprise a built-in A/D converter and stored sensor identifier, and communicates with a base station/host 335 which can include a transceiver for wireless communications, located near enough to reliably receive wired or wireless signals, through an RF transceiver 340 and antenna 345. Alternatively, the transceiver/base station 335 communicates with a remote host. In either case, the host ultimately links to viewing terminals 350 that can be, for example, integrated into the patient sensor or support system, in the patient room, at the nursing station, or at other locations. It will be appreciated that, while not shown, a battery or other power source is provided in the sensor 300. It will be appreciated by those skilled in the art that the functions of the host can reside in several different locations in a system in accordance with the present invention. For example, the host functionality can largely reside in the sensor itself, or that functionality can coexist within the base station, or it can be external to both, or the functions can be split across multiple devices.

In an embodiment of the sensor, the device is stored such that battery life is preserved until the unit is put into use.

Alternatively, the sensor is designed with a rechargeable battery or other energy storage device such as a capacitor. A rechargeable sensor can be recharged by connecting with a cable to some other energy source such as a power converter or can be recharged wirelessly through the use of an inductive charger. A non-rechargeable system may have lower cost and be more suitable for one-time disposable use in a hospital or other short-term care environments while a rechargeable sensor may have greater initial cost but may be more economical in a long term-care facility, such as a nursing home. The sensor can be activated by, for example, removing the adhesive backing on the unit, or by a conventional switch, or by exposure to ambient light in the patient's room, or activated upon exposure to a patient. Alternatively, the sensor can be activated by passive RFID, which can be built into the unit itself or embedded in the adhesive backing of the unit. The sensor can also be active by RF or inductive loops. Precautions are also typically taken to protect the sensor's accelerometers. Precautions can be taken, for instance, to prevent damaging accelerative forces from acting on the accelerometer. In an embodiment, the casing of the sensor unit can be compressible so as to decrease the accelerative force of a fall or impact. Alternatively, or additionally, the accelerometer can show when an acceleration large enough to cause damage or a need for recalibration is experienced and the senor unit can then signal that it is damaged or in need of calibration. In other embodiments, the sensor can also include an additional accelerometer capable of sensing accelerations greater than the acceptable range for a primary accelerometer, to be used to measure accelerations that can damage or cause a requirement for recalibration in a more sensitive accelerometer. In an accelerometer with more than 2 axes, all 3 axes can be used to determine orientation, providing more than one calculation of orientation that can be compared and used as an indicator that an accelerometer is damage or in need of recalibration The sensor, together with other system components as shown in, for example, FIG. 1, can provide real-time monitoring of a patient's orientation and surface pressure distribution over time, whereby patients requiring intervention can easily be identified. One embodiment utilizes small, thin, inexpensive, wireless and disposable sensors that safely monitor the 3-dimensional orientation of a patient over time. In one embodiment of the present invention, the sensors have an adhesive backing, such that they can be affixed to the patient's body. In an embodiment, one or more sensors can be placed on the body at known anatomic locations, although the anatomical location of the sensor(s) is not required to be known in some alternative embodiments of this aspect of the invention, as explained in greater detail hereinafter. The sensors can be placed on the body in a location that does not increase the risk for tissue damage. In one instantiation of this embodiment, a small sensor is affixed to the sternum or the anterior superior iliac spine (ASIS) of the patient. The sensors can also be embedded in articles worn by the patient, such as shirts or underwear bracelets, belts, or collars, as long as the sensor does not move significantly relative to the patient.

The sensors used in the present embodiment can contain one or more accelerometers, gyroscopes, magnetometers, or other devices, which are capable of measuring one or more conditions of the patient. The accelerometer can reliably and accurately measure patient tilt, patient orientation, patient movement, and vibration, and shock, as would occur with a fall. The accelerometer can be coupled to a wireless transmitting device, such that there are no wires extending from the patients to whom the sensors are attached. Wireless communication can be achieved via radio frequency transmission. Monitoring the wireless communication from the body sensors enables real-time tracking of the condition of the patient, including patient orientation and orientation-based pressure distribution over time. Alternatively, wireless communication can be implemented using an infrared or other optical link.

The present embodiment can be used to accurately monitor the static angle and acceleration of patients relative to the support surface. By continuously measuring the patient's orientation relative to the support surface the invention can determine to what extent the patient needs to be repositioned and/or the extent to which a next-scheduled turn can be skipped or delayed. Warnings can be given in response to a predefined condition, such as prolonged patient position at a specific angle relative to the support surface. The sensor data can be transferred to a central location that manages a network of monitored patients to ensure that all patients are being repositioned adequately. The network can be used to provide warnings to caregivers and to coordinate patient repositioning schedules amongst caregivers.

The sensors and monitoring system described in this embodiment are able to track the cumulative amount of time that a patient has been in a specific orientation relative to a support surface. The system can also estimate the surface pressure exerted on different regions of the body based on the direction of the gravitational force vector (as determined by the accelerometer), the orientation of the support surface, and the estimated magnitude of that force vector (as defined by physical attributes of the patient, such as height, weight, BMI, mass distribution, etc.). A computer can analyze the patient orientation/surface pressure data over time for each patient, and recommend optimal repositioning maneuvers based on this data. Furthermore, the cumulative surface pressure distribution for each patient can be seamlessly tracked and recorded as the patient moves to and from different support surfaces (i.e. bed, chair, wheelchair, couch, etc.). Information regarding each patient's pressure ulcer history, Braden score, and other conditions of the patient can be entered into the monitoring system. The computer can recommend an optimal repositioning schedule based on patient-specific data.

In one embodiment, the sensing system is properly secured to the patient in order to accurately determine the patient's orientation and surface pressure distribution. In an embodiment, the system of the present invention comprises means for automatically determining if the sensor system is properly attached to the patient. A system that can detect and notify the caregiver when the sensor is not attached, not attached properly, not oriented on the patient properly, not located on the patient properly, or is otherwise not working properly is desirable. Such a condition, if not detected, can result in the patient being in an orientation sufficiently long to develop a pressure ulcer or experience some other adverse medical condition. Depending upon the embodiment, the present invention can use any of several methods to verify proper location, orientation, and operation of the sensor. One set of embodiments comprises means and method for detecting biometric parameters that indicate if the orientation sensor is properly secured to the patient. In this approach, the orientation sensor is considered properly attached to the patient only when detected biometric parameters fall within predefined values based on known physiological behavior. If the detected biometric parameters fall outside of predefined limits, then the patient orientation sensor is considered to be improperly secured to the patient, or not attached to the patient, and caregivers can be alerted. The detected biometric parameters can include, but are not limited to, skin capacitance, respiratory rate, heart rate, and temperature. In the event of any error condition, where the measured parameters are out of range, the system notifies the caregiver that the system or more specifically, the sensor or base station is not working properly Another method to determine if the sensor is functioning properly is to range-check the raw data collected by the sensor. In the case of a sensor that is measuring acceleration in three axes, the magnitude of the acceleration or the components of acceleration that exceed a predefined maximum or minimum reasonable acceleration would indicate that the accelerometer or interface electronics are not working properly. In the case of other types of sensors, raw resistance, raw capacitance, raw inductance, etc. can be range checked against reasonable minimum and/or maximum values. The sensor can also monitor circuit voltage levels and current levels, battery voltage and battery current draw, battery charge state and report anomalous values to the base station. The sensor can have and compare multiple time bases, for example, more than one clock, oscillator, and/or timer. If the time bases give different values for elapsed time then the sensor can report anomalous values to the base station. Alternatively, a sensor with a single time base can compare elapsed time against a time base located in the base station.

An additional method for detecting if a sensor is not working properly is to compare the computed orientation, or location at a point in time or a range of orientations or locations over time against what might reasonably be expected. For example, if the computed orientation is an orientation that is impossible for the patient to assume then the sensor is likely not working properly. A paralyzed patient that is computed to suddenly change from a supine to a prone position may indicate a problem with the sensor. A sensor that rotates more than a prescribed maximum angular deviation, for example, 180 degrees in any plane, may indicate a failed sensor. A range of angular deviations and orientations can be identified such that, if the sensor is found to be outside of range, an error is indicated. Similarly, a sensor that assumes more than a prescribed maximum angular acceleration may indicate a failed sensor. A range of orientations that is unexpected or a computed orientation that is unexpected could also indicate that a sensor has been attached to the wrong body location. For example, a body extremity, such as the foot can assume orientations and undergo a range of orientations that is different than those for the pelvis or thorax.

A properly working RF communication link between the sensor and the base station, and between the base station and the nursing station, can be verified at a regular interval by communicating an expected message between these separate system components at prescribed intervals. Failure to receive the proper message at the proper time indicates the failure of the communication link.

Bio-metric data collected by the sensor can be used to verify its proper attachment, location, and/or function. For example, even if the primary purpose of the sensor is to collect orientation data, the sensor can also measure pulse rate, respiratory rate, skin capacitance, optical properties, or other physical properties of the patient to verify that the sensor has been properly attached, oriented, positioned, and/or is functioning properly.

The sensing system described in the present invention can be used to measure a patient's respiratory rate. As the chest rises and falls during respiration, a sensor 300 placed on or near the patient's thorax will undergo a cyclic pattern of acceleration/deceleration. The computer system of the present invention, including appropriate software as described herein, can interpret this cyclic pattern of acceleration/deceleration as a respiratory rate when it fits into physiologic parameters associated with human breathing, including but not limited to the rate, amplitude, and waveform of the accelerations/decelerations. In an embodiment, the system can be designed such that it uses the respiratory rate to ensure that the sensor is properly affixed to the patient's body. If the system does not detect a respiratory rate, it can be interpreted that the patient is apneic or the sensor may have fallen off the patient or the sensor may not be properly attached to the patient. If the system detects an abnormal respiratory pattern (which can include abnormal breathing rate and/or abnormal magnitude of chest rise/fall during respiration), it can be interpreted that the patient is in respiratory distress. The system can identify abnormal breathing patterns, such as hyperventilation, periodic respirations, sighing, air trapping, etc. If an abnormal respiratory pattern is detected, caregivers can immediately be alerted via an alarm mechanism.

In a similar fashion, the sensing system described in the present invention can be used to measure a patient's heart rate. As the heart beats in the chest cavity, a sensitive accelerometer placed on or near a patient's thorax will undergo a cyclic pattern of accelerations/decelerations. A cyclic rise and fall of the chest wall that is within physiologic limits (including, for example, amplitude, frequency, and waveform consistent with a physiologic heart rate) can be measured by an accelerometer 305 and can be interpreted by the system of FIG. 1, for example, to be the patient's heart rate. The system can be designed such that it uses the heart rate to ensure that the sensor is properly affixed to the patient's body. If the system does not detect a heart rate, it can be interpreted that the patient is in cardiac arrest or the sensor may have fallen off the patient or the sensor may not be properly attached to the patient. If the system detects an abnormal heart pattern or arrhythmia (which can include abnormal heart rate and/or abnormal magnitude of chest rise/fall during a heartbeat), it can be interpreted that the patient is in cardiac distress. The system can identify abnormal heart patterns or arrhythmias, such as tachycardia, bradycardia, fibrillation, etc. If an abnormal heart pattern or arrhythmia is detected, caregivers can immediately be alerted via an alarm mechanism. The sensor may also contain an embedded electrical activity sensor that is capable of detecting the electrical activity of the heart. The sensor can also be correlated with an EKG in order to increase the sensitivity/specificity of the monitoring system.

The patient orientation and surface pressure monitoring system described herein can be designed to automatically feedback directly into the pressure control system of patient support surfaces. Many support surfaces are capable of regulating surface pressure at discrete locations. By providing the pressure control system with information regarding the patient's position, orientation, location, movements, and surface pressure distribution over time, the surface pressure of the support surface can be optimized. The surface pressure can also be regulated such that the patient is automatically rolled or repositioned to relieve pressure on any high-risk areas.

Depending upon the implementation, the sensing system described in the present invention can be designed for home care, nursing care, or ambulatory care monitoring, without requiring direct caregiver support. The sensor can be worn by a patient (either affixed to their skin or embedded in an article of clothing) and the orientation/surface pressure distribution of the patient can be monitored either constantly or periodically. If the system detects the potential for pressure-induced injury, an audible and/or visual alarm can go off. The alarm can notify the patient of the need to change position/orientation, and upon doing so, the alarm can automatically turn off. The alarm can be programmed to turn off only if the patient repositions themselves sufficiently. In one embodiment, the alarm system described herein can be programmed to have increasing levels of audio or visual stimulation. For example, when the system detects that repositioning is indicated, a low-intensity sound can be produced by the system. If the patient does not reposition themselves, the intensity of the sound can increase until the patient has sufficiently repositioned themselves. If the patient is unable to reposition him or herself, then caregivers can be alerted. The sensing system described herein can be used as a telemedicine patient monitoring solution.

The patient orientation and surface pressure monitoring system described herein can be used to help prevent SIDS (Sudden Infant Death Syndrome). An infant position/orientation sensor is able to detect if an infant is lying facing up or face down on a support surface. Recommendations are in place for infants to sleep face up, so as to prevent accidental asphyxiation. The sensor unit can be used to inform caregivers when an infant, or any other person, is lying prone. The sensor can inform or alert caregivers when the infant is in a predefined orientation relative to a support surface and can also remotely send data to caregivers, such as via phone, pager, or computer system. The patient monitoring system of the present invention is capable of also measuring heart rate, respiratory rate and breathing patterns by analyzing movement of the chest wall. Information regarding respiratory rate and/or breathing pattern can be displayed and/or correlated with infant or patient position/orientation to increase the specificity of detecting potentially harmful orientations. The patient orientation sensor can be affixed directly to the patient's skin, or embedded in an article of clothing, such as a diaper or pajamas. An embedded temperature sensor can also be used to determine the skin surface temperature of the user. The sensing system can also monitor the physical location of the user, and indicate if the user has fallen, is walking, is rolling, is crawling, etc.

Figure 4A:
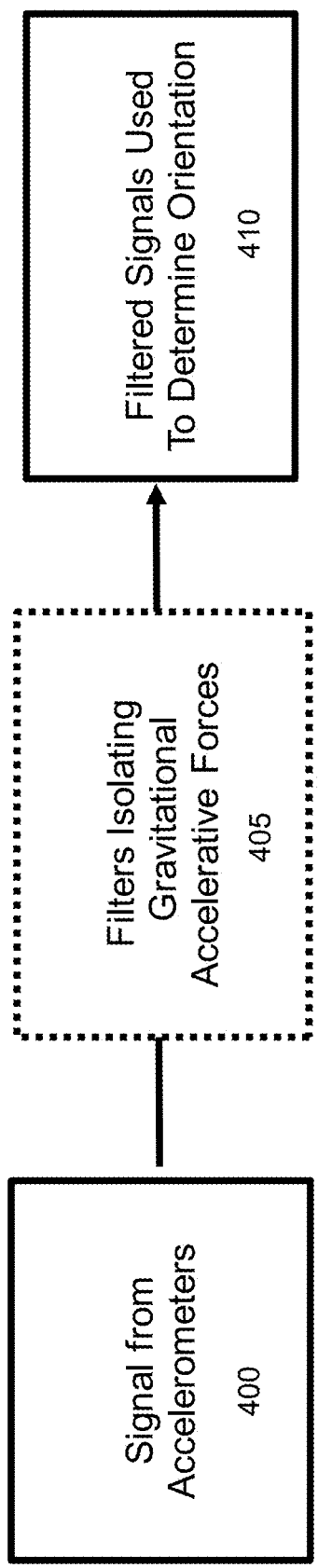
FIG. 4A illustrates the processing of signals from a sensor as shown in FIG. 3 to determine at least orientation.
Figure 4B:
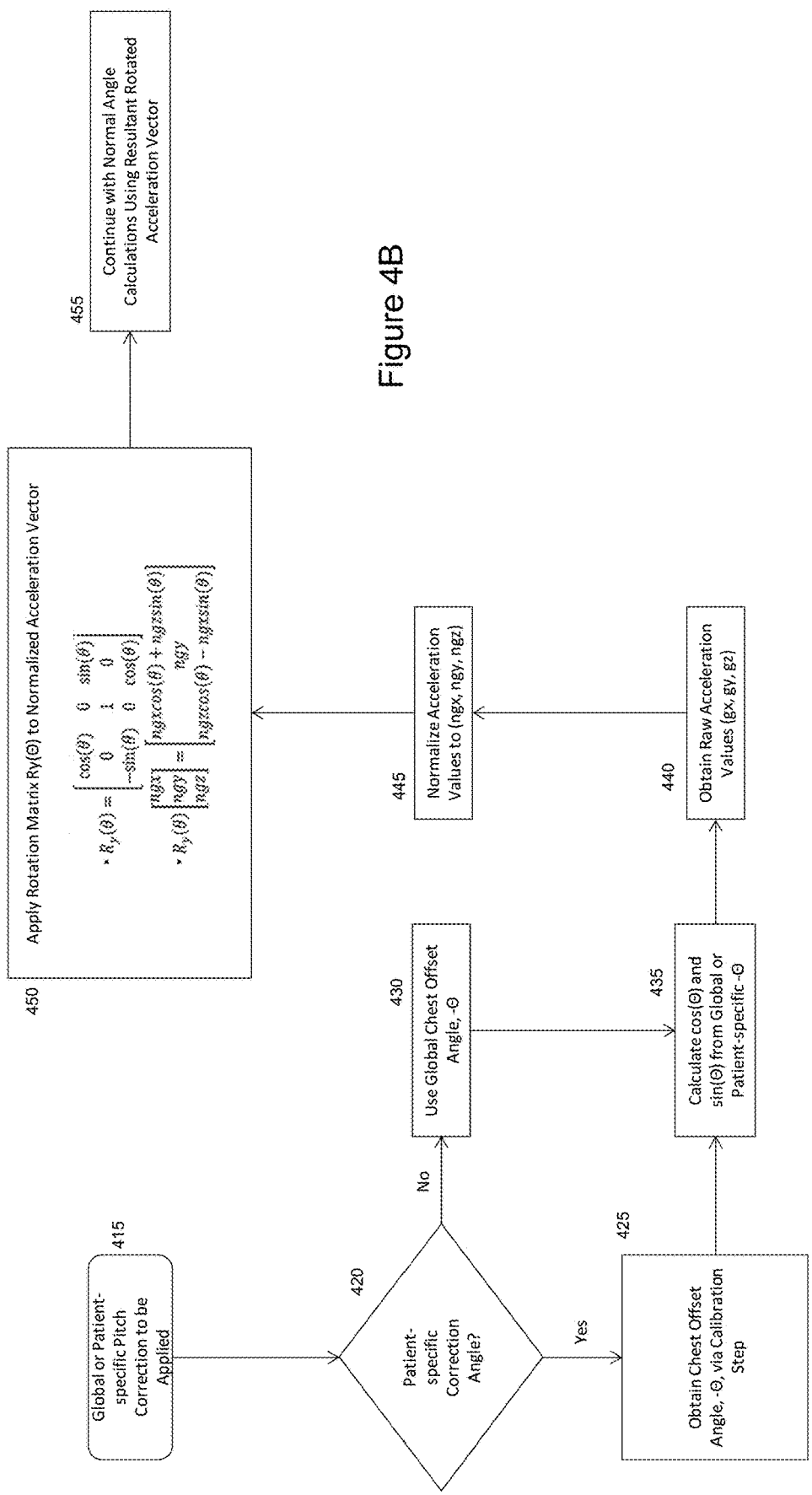
FIG. 4B illustrates in flow diagram form application of a correction factor to align acceleration data with a rotational axis of the body.

The sensor 300 not only detects accelerations due to changes in a patient's position/orientation, but also accelerations due to heartbeats, breathing, other movements, etc. To improve the detection of patient a patient's position/orientation, it is desirable to separate sensor signals caused by changes in a patient's position/orientation from acceleration signals caused by other forces including breathing, heartbeats, etc. To determine a patient's position/orientation, only the acceleration due to gravity is needed. At the same time, it can be useful in some embodiments to be able to monitor heart rate, breathing, and other vital signs with the sensor 300, as discussed in greater detail hereinafter. To determine patient position/orientation, it is desirable to filter out signals due to other sources, and this can be accomplished by the use of a low pass filter since patient turns are typically slow compared to other movements detected by the sensor 300. An example of a cutoff frequency for the filter can be 0.1 Hz (since the lower end of normal respiratory rates is approximately 0.2 Hz), though other frequencies can be used. Other methods for isolating the gravitational accelerative forces include taking the average, median, mode, or some combination of these of the accelerative signal over several readings. These methods allow for approximately removing the higher frequency and more random, less constant, or more cyclical accelerative forces. Components of the signal that give acceleration above 1 g can also be removed as noise, since the gravitational acceleration does not likely exceed 1 g for a user at rest. An additional method for isolating low frequency accelerations is to include an inertial mass on the accelerometer swing arm to reduce its inherent responsiveness to high frequency movement. Such an arrangement is shown in FIG. 4, where the raw signal 400 from the accelerometer is passed through one or more filters 405 for isolating the accelerative force due to gravity. Once the proper signals are isolated, the patient's position/orientation can be determined successfully, as at 410.

Figure 5B:
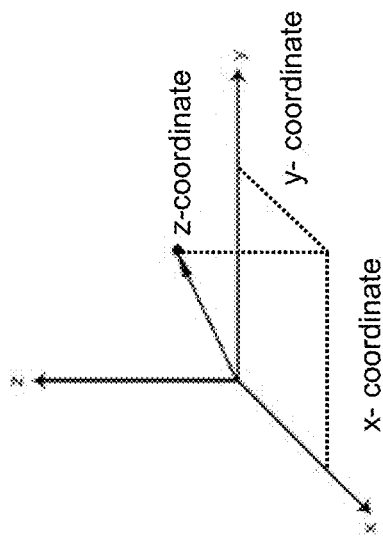
FIGS. 5A-5B illustrates the orientation of x-y-z axes relative to a patient using a sensor as shown in FIG. 3.
Figure 5A:
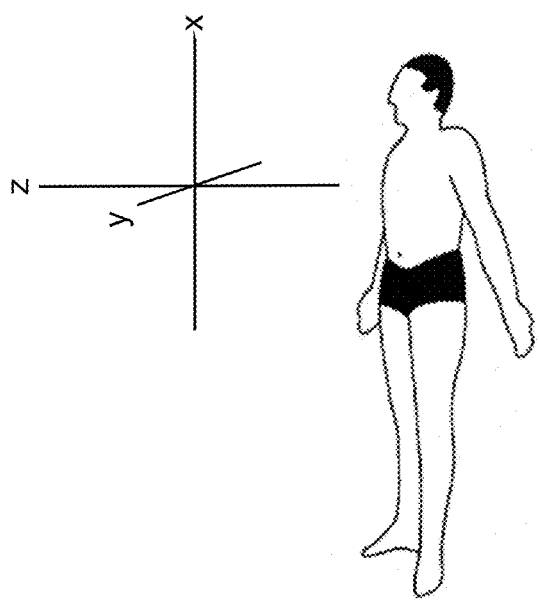

The method for using the sensor 300 to determine orientation can be better appreciated from FIGS. 5A-5B. The sensor is attached to the user such that the orientation of the user is measured by the accelerative forces experienced by the accelerometer. The separate axes of the multi-axis accelerometer are often oriented orthogonally relative to each other, and shown in FIG. 5B. Shown in FIG. 5A is a 3-axis accelerometer with one axis (x in this case) aligned along the cephalic-caudal axis of the user, another (y) aligned along the left-right axis, and another (z) aligned along the anterior-posterior axis. The side-to-side rotation of the user is picked up by the z and y-oriented accelerometers. The Trendelenburg and reverse Trendelenburg tilts of the user (head to toe tilt) are picked up by the x and z oriented accelerometers. As such, it may be redundant to have more than 2 orthogonal axes sensed by accelerometers. However, the redundancy can be used for several purposes including: confirming the orientation calculation, and using different accelerometers for different angles of orientation to allow for the accelerometers to operate in their most accurate angle zones.

Consider an example, where the user is tilted 30 degrees to the right side. The component of gravitational acceleration along the x-axis accelerometer does not change. However, it does change on the y-axis and z-axis. With the patient lying flat, the z-axis accelerometer experiences the maximum acceleration due to gravity in the downward/posterior direction, as it is parallel to the direction of gravity. The y-axis accelerometer experiences minimal gravitational acceleration as it is perpendicular to gravity. As the user tilts to the right, the component of gravity experienced by the z-axis accelerometer decreases and the component of gravity experienced by the y-axis accelerometer increases. When the user reaches 30 degrees of tilt to the right side, the z-axis accelerometer experiences approximately cosine(30)g of gravitational acceleration. At this orientation, the y-axis accelerometer experiences sine(30)g=0.5 g of gravitational acceleration. For other orientations involving tilting about the x-axis/cephalic-caudal axis, the acceleration experienced by the z and y accelerometers will follow a similar relationship where 30 is replaced by the angle of tilt. Similarly, if the user is tilted in the Trendelenburg or reverse-Trendelenburg positions, the z-axis accelerometer experiences approx cosine(angle)g of gravitational acceleration and the x-axis accelerometer experiences sine(30angle)g of gravitational acceleration. By knowing the gravitational acceleration experienced by the accelerometers, one can then find the angle of the tilt. In the case of a simple tilt where there is only tilting about one axis, this can be accomplished by taking the arc-sine or arc-cosine of the ratio of the measured acceleration due to gravity to magnitude of gravitational acceleration.

Figure 6:
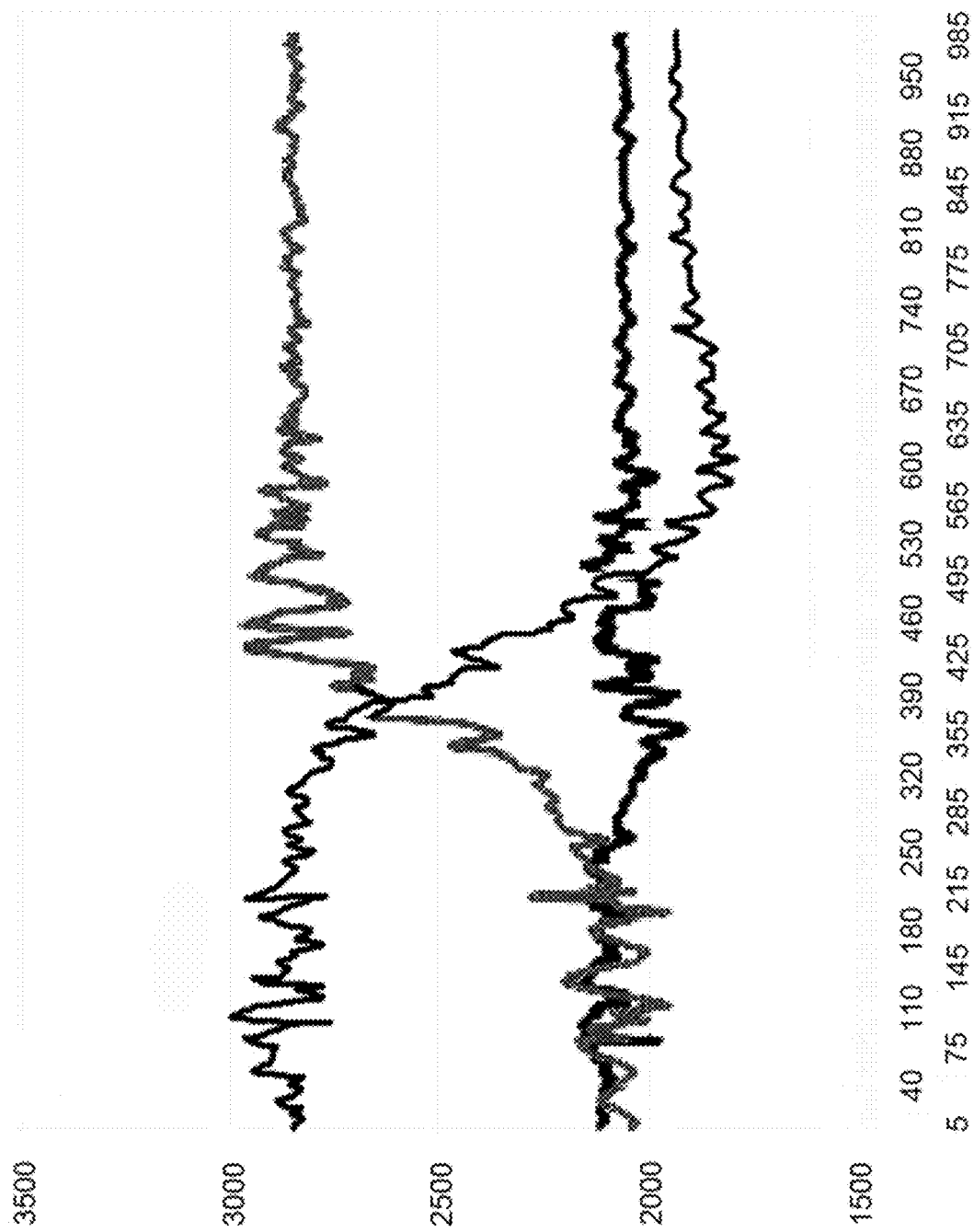
FIG. 6 illustrates a sample response of the x-y-z accelerometers due to a ninety degree turn, or roll, by a patient, such as turning from a supine position to lateral decubitus position.

FIG. 6 shows sample data from a 3-axis accelerometer showing a 90 degree turn of a user. The z-axis accelerometer initially shows a 1 g acceleration when the sensor is flat and then shows approximately 0 g when the sensor is at 90 degrees. Note that in FIG. 6 the acceleration is not in units relative to g but as output from the accelerometer. The opposite is true for the y-axis accelerometer. In the case of tilting about more than one axis, the component of the gravitational acceleration experienced by the accelerometers is reduced compared to a non-tilted state. For instance, if the user is in the reverse-Trendelenburg position (head tilted up relative to feet) by 5 degrees, then when the user is now tilted side-to-side (i.e. about the x axis), the z-axis accelerometer experiences cos(5 degrees)*g instead of the full g. As the user is tilted about the x-axis, the z-axis acceleration measurement continues to be decreased at a ratio of cos(5 deg). Similarly, for the y-axis during side-to-side rotation (about the x-axis), the y-axis gravitational acceleration measured is decreased at a ratio of cos(5 deg). A similar calculation is used for any angle of inclination of the z-axis, replacing the 5 degrees by the angle of inclination. Similarly for a rotation about the x-axis, the gravitational acceleration measured by the z and y-axis are decreased at a ratio of cos(angle of rotation).

In general usage, if there is tilting about more than one axis, the user is tilted in the Trendelenburg or reverse-Trendelenburg position and being rotated about the x-axis. In this case, the x-axis acceleration can be used to determine the angle of tilt about the y-axis using techniques as described above. This angle of tilt is then used in the calculation of the rotation about the x-axis, by dividing the ratio of the experienced acceleration by the magnitude of gravitational acceleration by cos(angle of tilt about y-axis) before proceeding with the calculations to determine the angle of tilt, again as described previously, e.g.:

arcsin{[(measured gravitational acceleration in y-axis accelerometer)/g]/[cos(angle of tilt about y-axis)]}="angle of tilt about x-axis"

The angle of tilt about the y-axis can be measured by other means as well. The tilting about the y-axis is often related to the tilting of the support surface. This tilting of the support surface can be determined by placing or attaching a separate orientation sensor in a fixed position relative to the support surface and determining the orientation of the support surface, or part of the support surface. This can also be achieved by having information regarding the orientation of the support surface entered into the system. This data collection can either be done manually or by directly communicating with the support surface (if the support surface has orientation sensors and has the ability to output the data in a usable format).

In some embodiments it is desirable to calibrate the accelerometers to achieve a desired accuracy. Calibration determines constants that enable acceleration to be described in real, physical units. During "calibration", the device's raw output can be calibrated by determining the appropriate constants that can be used to determine physical units such as m/s/s, ft/s/s, g's, etc. The calibration process can involve determining the readings from the accelerometers throughout a representative sample of its orientations. Calibration constants can be determinedand used to get more accurate acceleration data. One method of determining the calibration constants is to orient the sensor such that it experiences 1 g and −1 g of acceleration along each of the axes in which acceleration is measured. The sensor can then be calibrated such that the output from the accelerometer when it experiences 1 g or −1 g of acceleration is associated with a 1 g or −1 g acceleration, respectively, This process can be done prior to distributing the sensor to end users, or it can be performed by the end user using instructions or calibration tools that can be provided. The calibration constants can provide, for example, multipliers and offsets such that a calibration equation may be acceleration=(accelerometer reading)*M+O, where M is the multiplier and O is the offset. Depending on the degree of linearity of the accelerometer readings throughout its range, the calibration equation can take on forms other than that of a linear equation.

In addition to calibrating the accelerometers, it is also helpful in at least some embodiments to calibrate the angle of the accelerometers with respect to the rotational axis of the patient on whom the sensor will be placed. A typical placement of the sensor of the present invention is on the sternum. However, for most people, the sternum is not perfectly parallel to the rotational axis of the body, which basically runs vertically from the center of the skull down to the feet. Instead, for most people there is a slope downward from the sternum to the neck, and this downward chest angle, or pitch, can vary significantly, perhaps as much as −50 degrees or more although 30 degrees is more typical, measured with respect to a line parallel to the rotational axis and tangent to the sternum.

Thus, to improve the accuracy of the sensor in detecting the rotation of the user, a correction factor or offset equal to the opposite of the patient's downward chest angle can be applied by applying a rotation matrix to rotate, about the Y-axis, the gravity vector detected by the accelerometer by the appropriate offset. Expressed mathematically, the correction is:

$$R_y(\theta) = \begin{bmatrix} \cos(\theta) & 0 & \sin(\theta) \\ 0 & 1 & 0 \\ -\sin(\theta) & 0 & \cos(\theta) \end{bmatrix}$$

$$R_y(\theta) \begin{bmatrix} ngx \\ ngy \\ ngz \end{bmatrix} = \begin{bmatrix} ngx\cos(\theta) + ngz\sin(\theta) \\ ngy \\ ngz\cos(\theta) - ngx\sin(\theta) \end{bmatrix}$$

For a correction of angle θ (i.e., the offset for a downward slope of −θ), the process performed in the processor comprises: the cosine θ and sine θ are calculated; raw acceleration values are collected from the accelerometer; the acceleration values are normalized to give ngx, ngy and ngz; and the rotation matrix shown above is applied. With the now-corrected values in hand, the remainder of the process of determining the user's orientation, or change in orientation, continues in the normal manner. It will be appreciated by those skilled in the art that the normalization can occur before or after the rotation. In some embodiments, it is adequate to apply a fixed correction offset for all patients. In embodiments which utilize such a global offset, it can be beneficial to choose an offset value conservatively, i.e., smaller, since some chests have shallower angles, or even a positive angle. In a more generally applicable embodiment, it can be desirable to determine a correction offset based on the actual chest angle of the specific patient or other user. This can be done by placing the patient in a known orientation, for example either supine or standing vertically, such as against a wall. The accelerometer measurements from the sensor are then taken, and the chest angle for that specific patient can be calculated from those measurements with reference to the known orientation.

An embodiment of the process described above can be appreciated from FIG. 4B. The process starts at 420, with the decision that a correction is to be applied. If a patient-specific correction angle is available, as discussed above, the process advances to step 425 where that correction value is retrieved from its storage location, typically expressed in degrees or radians and indicated by θ. If a global correction value is to be used, the process advances from step 420 to step 430 where the global correction value is retrieved from its storage location. In either event, the sine and cosine of the correction value θ are calculated at 435. The uncorrected, or raw, acceleration values are also retrieved either from the accelerometer (and associated processing as appropriate for signal compatibility) or from a storage location, shown at 440. In the exemplary embodiment illustrated in FIG. 4B, the acceleration values are then normalized in step 445, and a rotation matrix is applied at step 450. As noted above, normalization can be performed either before or after the application of the rotation matrix. In either approach, the normalized output of the rotation matrix step is provided to the remainder of the process for determining orientation, as shown at 455.

In some instances, the sensor of the present invention is not placed on or near the sternum, and instead is placed laterally of the patient's midline, and closer to the clavicle. In such instances, a roll correction may be desirable in addition to the pitch correct discussed above. The calculations for correction of roll are analogous to those described above, although the rotation matrix is applied around the X-axis. Further, in the event that the sensor is not placed on the patient in accordance with indicia on the sensor, a yaw correction may also be desirable. In an embodiment, correction for yaw can be achieved by the combination of an accelerometer and a magnetometer, with the magnetometer calibrated to magnetic north or providing a reference magnet in a known and repeatable location, such as the at the patient's head or foot or aligned with the patient's longitudinal body axis.

Calibration of the accelerometers throughout their desired range of orientations can allow for more accurate orientation measurement. Each type of accelerometer, or each individual accelerometer, can be tested and calibrated depending on the level of accuracy desired. A plot of the angles calculated based on the accelerometer data vs. the actual angle being measured can be used to create a regression that can then be used to improve the accuracy of the calculation. Once the regression is made, the calculation of orientation can be made using data from the regression. The physiologic heart rate has a range, speaking generously, of approximately 30 to 350 bpm. So when isolating the accelerative signal from the heart beat, one can choose to look at signals within this range or a similar frequency range. A band pass filter can be used to attenuate signals with frequencies above and below this range. Since the accelerative forces due to the heart beat can be large relative to the other accelerative forces experienced in a resting user, there may not be a need to significantly filter the data in order to detect the heart rate with reasonable accuracy. The heart rate can be detected by looking for periodic signals that have a higher than normal amplitude or a low-pass filter can be used to attenuate signals above a certain frequency. For example, frequencies higher than approximately 6 Hz (i.e. 350 bpm) can be attenuated. It is also possible to increase or reduce the amount of filtering, by changing the attenuation or changing (shifting, narrowing, broadening, etc.) the band pass frequencies. For instance, for a resting patient, the range of frequencies that are most common may be 35-120 bpm. A band pass filter covering this range may be useful for most cases. It is possible to capture other frequencies by having a separate, wider, or shifted filter that is added on with a different gain or analyzed separately to accommodate for less common heart rates. The attenuation can also be turned down to similarly increase the range of frequencies. A tight band pass filter (eg. covering a narrower range of frequencies or having greater attenuation, etc) can provide cleaner signals; for example, a Butterworth filter can be used, although many other types of filters can also be used.

The quality of the filtering becomes more important when the signal is smaller or when there is more noise. Some examples of when this can occur include: the sensor is not placed close to the heart (eg. in the pelvic area), when the user has more material intervening between the sensor and the heart or artery (eg. skin, fat, non-organic materials like clothing, etc.), or when the pulse is weaker (eg. impaired heart contraction or low blood pressure/pulse pressure). In such cases the filtering becomes more important and the methods described above for improving the filter may be required to isolate the heart rate. The optimal placement of the sensor is in close proximity to the heart (or major arteries) in order improve detection of the pulse and heart rate. Placing the sensor on the chest, especially near the sternum, is optimal for detecting the heart rate. Placing the sensor at locations close to the aorta or other large arteries are good sensor placements for detecting the heart rate at locations more distant from the heart.

When the sensor is placed with the 3 axes oriented as shown in FIG. 5A, the heart rate (and breathing rate), is sensed mainly by the z-axis accelerometer. When positioning a sensor that is intended to detect heart rate or breathing rate, the quality of the signal is improved if at least one accelerator is positioned in approximately the anterior-posterior axis (or z-axis as shown above).

In certain cases it can be useful to keep track of when:
the heart rate (HR) is above a certain threshold
the HR is below a certain threshold
when the HR changes quickly
when the HR is irregular
when the magnitude of acceleration is above or below a certain threshold
when the magnitude of acceleration changes quickly or is at a rate above a certain threshold
when the heart rate detected by the accelerative sensors is different from the heart rate detected by electrical signal sensors.

This can be important for cases of ventricular fibrillation, where electrical signals from the heart are present but the mechanical heart beat is not present or is irregular. In such a case, the accelerometer data can be compared with EKG data, where the signal detectors for EKG data are either external or internal to sensor 300.

Detecting the mechanical activity and/or electrical activity of the heart, as described above, can provide an indication of abnormal physiologic conditions, such as tachycardia, bradycardia, arrhythmias, heart attacks, pulseless electrical activity (PEA), heart failure, etc.

Sensing a patient's breathing rate is also desirable in some embodiments of the invention. The physiologic breathing rate has a range, speaking generously, of approximately 3 to 100 bpm. When isolating the accelerative signals resulting from breathing, it is desirable for at least some embodiments to choose to look at signals within this or within a similar frequency range. As with heart rate, a band pass filter can be used to attenuate signals with frequencies above and below this range. Often the accelerative forces that result from breathing, especially with breathing at rest, are small relative to the heart rate. As such, filtering can be desirable. Methods to improve the filtering beyond a basic band pass filter can be implemented if appropriate to the embodiment. This includes, for example, narrowing the band to between 5-30 breaths per minute. A band pass filter covering this range may be useful for most situations. Another issue is that the range for physiologic breathing and heart rate can overlap. One can take advantage of the fact that the heart rate is usually higher than the breathing rate. The narrowed band pass filter can achieve the desired differentiation. The filtering can also be adaptive, such that the heart rate is detected first and then the filter adjusts so as to have an upper cutoff that is below the heart rate. As with heart rate, a tighter band pass filter can yield cleaner signals; again a Butterworth filter can be used, among a variety of acceptable band pass filters.

In certain cases it may be useful to keep track of a patient's breathing rate, such as when:
- the breathing rate (BR) is above a certain threshold
- the BR is below a certain threshold
- when it changes quickly
- when it is associated with the administration of medications
- when it is irregular
- when the magnitude of acceleration is above or below a certain threshold
- when the magnitude of acceleration changes quickly or at a rate above a certain threshold
- when the heart rate is below the breathing rate
- certain patterns of breathing, eg. Cheyne-Stokes respirations Detecting the respiratory rate and breathing pattern, as described above, can provide an indication of abnormal physiologic conditions, such as tachypnea, hypoventilation, Cheyne-Stokes (strokes, brain injury, encephalopathy, heart failure), etc.

Patients may move on their own, and it can be useful to determine their activity level or lack thereof. It is important to isolate this signal from other physiologic signals. In general, there are components of acceleration that are due to the normal voluntary movements of a user. These movements can have a magnitude that is greater than the acceleration due to breathing, heartbeats, and pulses. One method of isolating a user's movement-based acceleration is to isolate the accelerations that have magnitudes beyond those expected to be due to breathing and heart beat/pulses. This threshold of magnitude can be pre-programmed based on physiologically normal accelerations due to heartbeats, pulses, and breathing. The threshold can also be directly measured from the accelerations measured on the user, either at the same time or during another time when the patient is determined to be still. Another method of isolating movement-based accelerative signals is to subtract the filtered signals of the heart rate and breathing from the initial signal.

The user may be subjected to environmental noise, such as due to machinery. Many patients that are at risk for pressure ulcers are put on "alternating-pressure" mattresses. These mattresses have a series of individual air columns that independently modulate their pressure, thereby creating depressurization waves that travel under the patient. Although these waves can travel very slowly, they can cause subtle movements of the patient that will need to be accounted for. Algorithms for filtering out this noise, as well as any other environmental noise, will be straightforward for those skilled in the art, given the teachings herein. Environmental noise can also be due to electrical interference, etc. Undesirable environmental noise sources may include nearby electrical or mechanical equipment, building HVAC or other infrastructure systems, and/or other human activity.

The movement-based accelerative sensing can be used to monitor the activity level of the patient in order to encourage activity or to discourage activity. It can also be used to automatically determine mobility for the purposes of charting, for example for determining some of the components of the Braden scale (i.e. mobility, activity, shear forces, etc.).

Other signal analysis can be performed on the signals from the accelerometers. The overall waveform of acceleration due to heart beat/pulse is known, as well as the waveform for the accelerations involved in breathing. Signal analysis can be used to analyze the waveform of accelerative signals to gain more information from the signal, such as its source or association with different physiologic conditions. For example, the waveform for a breath is different from the waveform for a heart beat or pulse. Thus, the waveform and/or the frequency can be used to help isolate/identify the HR and BR. The waveform of a patient turn can also be identified. In addition, within the accelerative waveform of the heart beat/pulse, there can be different physiologic conditions that affect the waveform. For instance, a different waveform exists between normal heart beats and ventricular fibrillation. Changes in waveform or abnormal waveforms can be detected in this way. This applies similarly for breathing. The algorithms can also learn from the normal state of the user to help better identify the range of normal HR and BR as well as the normal waveforms for a particular user. This will be useful when any of these change greatly. This algorithm can also learn from greater data sets from one user or multiple users to improve its accuracy and precision.

Figure 7:
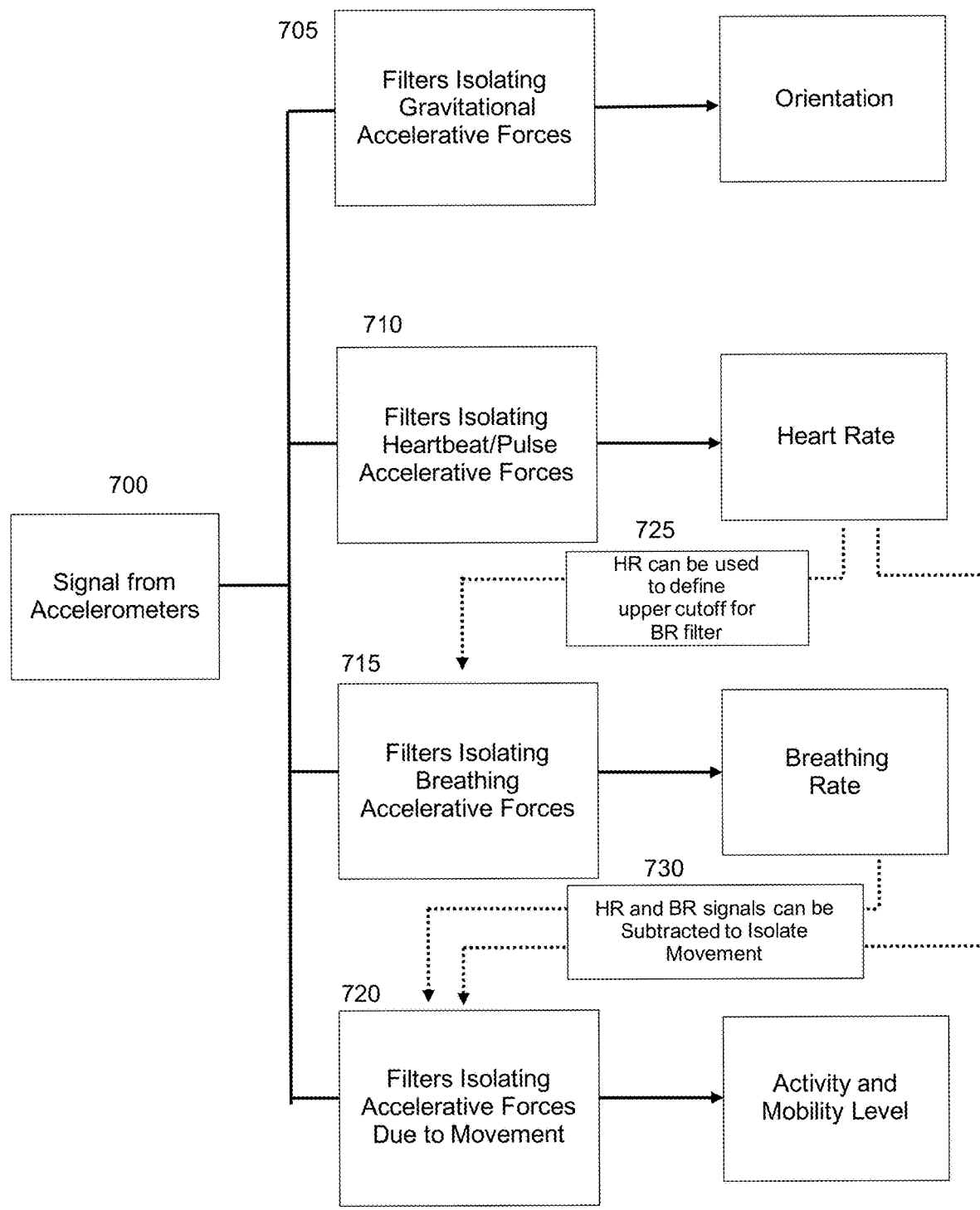
FIG. 7 illustrates in flow diagram form the filtering steps used to isolate orientation, heart rate, breathing rate and movement data from the raw accelerometer signals, including feedback paths for improving filtering.

FIG. 7 illustrates the foregoing process, and shows the filters used to isolate orientation, heart rate, breathing rate, and movement data from the initial accelerometer signals, as well as paths to enable the filters to learn. More specifically, in an embodiment, signals 700 from the accelerometers are received by a set of four parallel filters 705-720, including a filter 705 for isolating gravitational accelerative forces, a filter 710 for isolating heartbeat/pulse accelerative forces, a filter 715 for isolating breathing accelerative forces, and a filter 720 for isolating accelerative forces due to movement. In addition to movement and orientation, the acceleration measurements can be used to detect other characteristic accelerative events, such as falls. At block 725, the heart rate output is used to provide an upper cutoff for the breathing rate filter, and feeds from block 725 to filter 715. Likewise, heart rate and breathing rate can be subtracted to isolate movement, as shown by block 730 feeding to filter 720.

Figure 8:
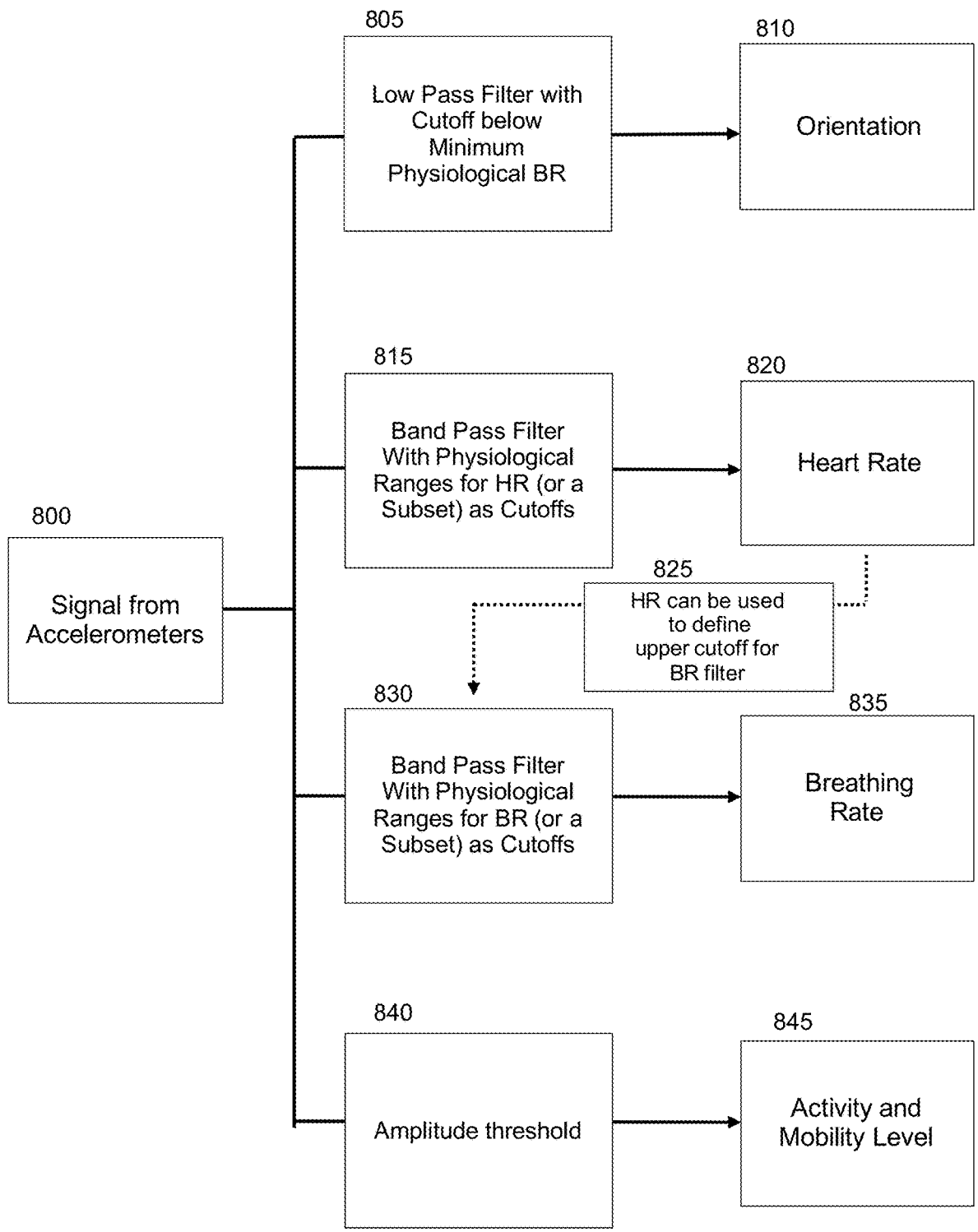
FIG. 8 illustrates in flow diagram form an embodiment of a filter in accordance with this aspect of the invention.

Referring next to FIG. 8, one of the filters of FIG. 7 can be understood in greater detail. The accelerometer signal 800 is provided to low pass filter 805, with a cutoff below the minimum physiological breathing rate, to isolate orientation as shown at 810. To isolate heart rate, the signal 800 is fed to a band pass filter 815 with a physiological range of heart rates, or a subset, as the cutoff, yielding an output of heart rate as shown at 820. In addition, heart rate data is fed via block 825 to a band pass filter 830, which also receives the signal 800 and isolates breathing rate as shown at 835, including using heart rate as the upper cut-off for breathing rate. Amplitude threshold block 840 also receives the signal 800, and isolates activity and mobility level as shown at block 845.

There are instances when a patient's vital signs can be affected by positional changes. The position/orientation sensors described herein can be correlated with a patient's vital signs in real-time. Data from the position/orientation sensors can be correlated with vital sign measurements that are obtained via standard modalities (EKG, blood pressure cuff, manually counting palpable pulsations of the arterial pulse, manually counting respirations, etc.). Data from the position/orientation sensors can also be correlated with vital signs using a single sensor that can determine both the patient's position/orientation and vital signs. In one implementation, an accelerometer placed on the patient can determine the position/orientation of a patient, as well as the heart rate and respiratory rate. When the sensing system detects dramatic changes in heart rate that are associated with changes in position/orientation, caregivers can be notified that the patient may have orthostatic hypotension. Patients with orthostatic hypotension will commonly experience a decrease in blood pressure upon standing that is associated with a rapid acceleration in heart rate (usually an increase of over 20 bpm). In fact, the diagnosis of many conditions (i.e. orthostatic hypotension, autonomic dysfunction, postural orthostatic tachycardia syndrome, etc.) can be aided by using a tilt-table test, where patients are put on a platform that tilts and vital signs are monitored.

There are other instances when a patient's vital signs are affected by position. For example, when patients with CHF lie flat they can develop respiratory distress that manifests as an increased respiratory rate. Similarly, patients with morbid obesity or obstructive sleep apnea can develop respiratory distress when they lie flat (the extra weight due to fat around the chest and neck can increase the work of breathing) and these patient's breathing patterns can change based on the postural changes. In one implementation, an accelerometer placed on the patient can measure both the patient's position/orientation and respiratory rate. When the sensing system detects changes in respiratory rate that are associated with changes in position/orientation, caregivers can be notified and further workup initiated.

Conditions that can be affected by position can be entered into the monitoring system. For example, if a particular patient has CHF resulting in severe orthopnea, this condition is entered into the system and then the turning recommendations allow for the patient's head/chest to remain elevated by 30 degrees throughout the day (patient's with CHF can't handle the extra fluid load that occurs when lying supine, hence they get short of breath when lying flat). As a consequence, since the patient's head/chest is elevated throughout the day (thereby increasing the pressure-dose on the sacrum), the system can then recommend increasing turning frequencies, etc. to help prevent sacral ulceration. Any condition of the patient (i.e. paralysis, amputations, injuries, diabetes, anorexia, obesity, etc.) can be defined in the system.

It has previously been described herein how sensing the patient's breathing pattern and heart rate can be used to determine if the sensor is properly affixed to the patient.

Similarly, electrodes or capacitive sensors which are capable of measuring the body's electrical activity, impedance, or resistance can be used to determine if the sensor is properly affixed to a patient. A thermometer can also be used to determine if the sensor is properly secured to the patient. When the skin surface temperature reading shows temperatures sufficiently close to the expected skin temperatures, it can be assumed that the sensor is affixed to the patient. Similarly, if a sudden change in the skin surface temperature is detected, it can be inferred that the sensor has lost continuity with the patient.

Another technique that can be used to determine if the sensor unit is properly attached to the patient is a tab that is attached to a conductor within the sensing unit's circuitry. After the unit is affixed to the patient, if the unit is subsequently removed, the tab detaches and changes the circuit in a measurable way, such as by changing the resistance. This allows the sensing unit to know that it has been removed from the patient and the sensing unit can send this information to the host or other reader. In some arrangements, the tab can also be affixed with greater strength to the patient due to differences in affixing compound or a heat-activated bonding substance.

The sensor unit can be oriented to work automatically when placed anywhere on the patient. In this care, orient means to determine the direction of the accelerometer with respect to gravity or with respect to the patient. During "orientation", the accelerometer's direction can be determined with respect to gravity by measuring the acceleration in the three axes as the device is rotated in each of the three axis of rotation. Some placements can be at the sternal notch or the xiphoid process of the sternum or the anterior superior iliac spine (ASIS). The sensor unit can also be placed anywhere on the patient and oriented to the patient. In an embodiment using this approach, the patient lies supine with the sensor unit in place. A button on the reader unit, the sensor itself, a remote, or a computer interface can be pushed or a command sent once the patient is supine, and the reader unit will then associate the reading from the sensor unit with the supine position. Thus, the sensor unit can be at placed at any angle relative to the patient and the system will be able to oriented accordingly. The signal to the system that the patient is supine can come in any number of forms including voice activation, etc.

Different sensors can be pre-calibrated for use on patients with different body types. For example, a sensor that has a unique identifier can be placed on patients that have a specific BMI. In such a manner, the system will detect the unique identifier from the sensor, and automatically calibrate the monitoring system for a patient with a specific BMI.

Similarly, the sensors placed on the support surface can be pre-calibrated for use on support surfaces with different properties. For example, a sensor that has a unique identifier can be placed on support surfaces that have a specific surface pressure profile (i.e. dry pressure, air pressure, air fluidized, etc). In such a manner, the system will detect the unique identifier from the sensor, and automatically calibrate the monitoring system for a support surface with a specific surface pressure profile.

In at least some embodiments, the sensing system is designed such that it does not require any additional manipulation by a care provider. As previously described, the sensor can automatically be activated when its adhesive backing is removed. The removal of the adhesive backing allows for the activation of a sensor circuit and hence discharge of the unit's on-board battery. To conserve power, the sensor can locally store acceleration data and transmit this information to the receiving station(s) at predefined intervals. A disposable sensor unit can be designed such that it is able to transmit acceleration data for an extended period of time, such as days or weeks.

The sensor unit can be designed such that it does not draw power (or at least very little power) when it is in its packaging. In some embodiments, it is activated immediately before being placed on the patient. Alternatively, a signal received from the transceiver can serve to activate the sensor unit. One type of activation signal can be an RF signal that is sent to the unit. If the sensor unit is not a passive RF unit, the unit can temporarily act as a passive tag before activation and be powered by the received signal. As another alternative, a passive tag or an RF receiver/transceiver that has the ability to passively receive signals can be initially included as part of the sensor, and can be used to allow for a signal to be received by the by the sensor without using stored energy in the sensor. This signal can be used to activate the sensor. The passive tag can then be removed promptly following activation, as a method for reducing the size of the sensing unit and allowing the passive receiver/transceiver antenna to be larger.

For units that sense physiologic variables such respiratory rate, heart rate, and/or temperature, in an embodiment the reader can allow for a period of time (seconds, minutes, or hours) after activation before it expects physiologic values to be measured. This can allow time to attach the sensor to the patient before the system expects to receive physiologic data.

Another variation has the sensor activated by a switch on the unit.

Proper placement of the sensor 300 on the patient is important in at least some embodiments. In at least some embodiments, the sensor is placed on the patient such that there is no potential for movement of the sensor with respect to the patient. In an embodiment, the sensor is adhered directly to the skin using an adhesive patch, which can be similar to that used for standard EKG leads, although in other instances the sensor can be removed from the adhesive backing to permit replacement of the sensor while protecting the patient's skin.

The sensor is ideally placed on the anterior thorax, pelvis, upper thigh or shoulder. In ideal usage there is little relative movement between the sensor and the user's pelvis, which enables an approximate determination of the orientation of the user's pelvis. In an embodiment, the sensor must be placed at a location on the body where the orientation of the sensor approximates the orientation of the patient's pelvis and/or thorax.

By knowing the orientation of the patient's pelvis and/or thorax, the surface pressure distribution across other body structures can be estimated. For example, if it is determined that a patient is in a completely supine orientation, it is then known that surface pressure is being exerted on the patient's sacrum, and ischium. However, based on the patient's orientation and the known anatomic relationships that exist between different body structures, it can be inferred that structures such as the posterior occiput, elbows and heels are also experiencing pressure. If the patient then turns to a left lateral decubitus position, it can be determined that surface pressure has been transferred to the patient's left hip, as well as other body structures, such as the left shoulder, left elbow, left occiput, and left lateral malleous.

When the patient's pelvis is determined to be in a left lateral decubitus position, it is very unlikely (if not impossible) for surface pressure to be exerted on the patient's right hip, right occiput, right elbow, right shoulder, or right lateral malleolous. There are anatomic relationships that exist between different body parts that prevent pressure from being exerted at these locations. In such a fashion, the overall surface pressure distribution map of a patient can be estimated based on the known orientation of one or more body structures, such as the pelvis or thorax.

In at least some embodiments, it is preferred that the sensor not be placed on the limbs or head, because the orientation of the limbs does not always approximate the orientation of the pelvis/thorax. The location of placement may be different if the primary concern is for preventing and managing pressure ulcers at locations other than the pelvic region. For example, if the patient has a pressure ulcer on their right heel, a sensor can be placed on or near the right foot, ankle, or lower leg to better approximate and monitor the orientation and surface pressure distribution of the affected region. In an embodiment, the sensor should not be placed in a location where it will be susceptible to being rolled on.

In order to accurately determine a user's orientation, it is important in at least some embodiments to know the orientation of the sensor with respect to the patient. o facilitate properly orientating the sensor with respect to the patient without requiring significant training, an index mark can be provided on the sensor 300. Such index marks can provide information including but not limited to which direction the sensor should be oriented (eg, top of sensor towards the patient's head) or where on the patient the sensor should be placed. Examples of index marks are shown on the different sensors 900A-900E illustrated in FIG. 9, including two, 900C-D, with cross-hairs on a representation of a human for indicating the location where the sensor should be placed and where the orientation of the human image on the sensor is to be aligned with the user (i.e., head pointing in same direction in image and user). The three other examples in FIG. 9 are for indicating simply the desired orientation of the sensor including an arrow, an arrow labeled "head", and a human image representation. In an embodiment, the orientation of the sensor with respect to the patient must be determined to accurately determine the relative surface pressure distribution of the patient. The indicia need not reference the head, as long as there are sufficient and simple instructions or indicia to place the sensor relative to an identifiable landmark on the body and a in a relative orientation to that landmark, whether the landmark be the sternum, belly button, anterior superior iliac spine (ASIS) spine, leg or other. The indicia can include but are not limited to markings on the sensor, the shape of the sensor itself, different materials or colors used on different parts of the sensor, or asymmetry of the sensor. The shape of the sensor or adhesive backing can also be more suitable to fitting in or conforming to specific areas of the body in specific orientations. The sensor can be incorporated into articles that may be worn by the patient such that when the article is worn the sensor is in an appropriate location and orientation.

In an embodiment, it is possible to automatically determine the orientation of the sensor 300 by, for example, sensing bioelectrical signals in the body. It is well understood that electrical impulses propagate away from the heart in a well-defined pattern, and the body has a known and well-defined polarity that can be detected. Referring next to FIG. 10, by providing the sensor 1000 with multiple bioelectrical sensors 1005 positioned circumferentially around the outer surface of the sensor, the plurality of bioelectrical sensors can be used to detect the average direction of electrical propagation, and either the sensor itself or the remote host can process the data to identify the orientation of the sensor 1000 with respect to the heart. In such an arrangement, the sensor 1000 can be placed on the patient at virtually any location on the thorax/pelvis (and in any orientation) and the sensor can automatically determine its orientation with respect to the patient.

Referring still to FIG. 10, the sensor picks up the electrical signal between the electrodes shown as open circles in reference to the common electrode 1010 shown as a solid circle and depending on the vector of the body's electrical signal at the location of the sensor can determine its orientation with respect to the patient. The magnitude of the signal (which can be an average or integrated magnitude) from the different electrodes gives an indication of the direction of the vector. For instance, if the signal from one of the electrodes shows a greater magnitude than the rest, then the vector can be determined to be closest to the direction of the line intersecting that electrode and the common electrode. The vector can also be determined to be in the direction between the two electrodes with the greatest magnitude of detected signals. As the signal detected in the electrodes can be positive or negative, the plurality of electrodes need only span approximately 180 degrees, for example, roughly a semicircle, to determine the vector direction within a 360 degree range, thereby reducing the number of electrodes needed per device and the number of sensing inputs and/or A/D converter inputs.

An alternate method for reducing the number of electrodes is to use two electrode sensing vectors spaced at a known angle (90 degrees is one exemplary implementation) as shown in FIG. 11. Based on the magnitude of the detected bioelectrical signals in each, the vector direction can be determined. This is illustrated in FIG. 10 where sensor 1015 comprises with electrodes 1020 and common electrode 1025.

Alternatively, using the sensor's built-in accelerometer, normal physiologic movements of the body due to respiratory and cardiac activity can be detected. The heart and lungs produce movements of the thorax, and these movements have a characteristic trajectory. By analyzing the trajectory of motion of the thorax due to cardiac and respiratory activity, it is possible to know the orientation of the sensing unit with respect to the patient.

As a still different alternative for self- or auto-calibration, the system can identify any accelerations that fall outside of the range of what is known and expected from normal movements of the human body. If the accelerometer is not placed correctly on the patient, when the patient is rotated it will appear that they are moving in a manner that is not compatible with normal body movements. If this is the case, caregivers can be alerted to confirm that the sensor is properly placed on the patient. Alternatively, the system can automatically re-calibrate itself to some extent by knowing the range of possible patient movements and correlating this information with data from the sensor. Caregivers can also provide input to the system regarding which direction they turned the patient and a learning-algorithm can then be used to calibrate the orientation sensor.

Since the system will coordinate patient turning, and may be used to document compliance with turning protocols, it is important in at least some embodiments to be able to confirm that the sensor is properly affixed to the patient. The sensor can detect specific physiologic parameters when it is properly placed. Sudden loss of signal of physiologic parameters indicates that the sensor is no longer properly placed on the patient, or the patient is having an acute event. For example, in one embodiment, the sensor can detect the capacitance of the skin. If the detected capacitance suddenly changes, it can be determined that the sensor has lost continuity with patient. If it is determined that the sensor has been removed from the patient, the sensor can be locked out and rendered nonfunctional, thereby avoiding any risk of accidental or fraudulent manipulation of the sensor.

In addition, each sensor can be assigned a unique identifier, and, in an embodiment, can be linked to a particular patient, for example either by a scan or other electronic data entry. Aside from avoiding erroneous readings, this permits a single monitoring system, such as shown in FIG. 1, to monitor a plurality of sensors.

In many cases it is important that the sensor data is associated with a certain patient. This may be the case in care settings in which there is more than one patient. It may also be the case in single patient settings in which the data from the patient needs to be stored and identified or associated with the patient. The needs of different care settings vary in terms of how they want the data from the system to be married to the patient/user. In one potential usage scenario, the care facility wants the patient data to be married to a sufficiently unique patient identifier, such as a medical record number (MRN). Other identifiers can include name, date of birth, room number/bed number, etc.

Where the care facility would like to associate the data with an MRN, there are several ways that the association can be made. In one method, a user may enter the MRN into the system of the present invention. The system can then send data along with the MRN or can be polled for the MRN associated with the data as needed.

The system can also assign a unique identifier to the data from a given sensor or group of sensors. This unique identifier can be different from the unique identifier of the patient used by the care facility. The unique identifier can also be a sufficiently unique identifier associated with the sensor itself that is used by the system to distinguish which sensor the received data is coming from. The care facility can then associate the unique identifier from the system with their identifier of the patient separately, in a separate computer system for instance.

One method for easily associating the MRN with the sensor can be that the user/caregiver scans the MRN from a scanable identifying unit on the patient (eg, bracelet with barcode, or RFID) or from some other source: eg chart, sticker, bed, etc. The sensor can also be scanned or polled for its identifier and the patient identifier and sensor identifiers can be married automatically at the bed side with the patient to reduce the likelihood of error. In an embodiment, the scanning system forms part of the present invention, and can be comprised of, but not limited to, an RF reader, a barcode reader, or a visual text recognition system. The sensor itself may include a scanner for the patient identifier and can then transmit that information to the host system.

During the marriage process, the system will need to know which sensor or sensors are being married to the patient identifier. The communication range of the sensors may mean that sensors other than the desired sensor(s) are within range. One method to associate the correct sensor is to have a short range RF reader to read the specific sensor being used. The user/caregiver may use a handheld short range reader to scan in the correct sensors. The short range reader may also be on a base station reader within the room. The user/caregiver can hold the desired sensor(s) in close proximity to this short range reader when performing the marriage of the sensor and patient identifiers. The short range reader may also be the same reader as the reader for receiving sensor data, but placed in a short range read mode, which may be achieved by reducing the power of the reader's transmission or increasing the threshold of received signal power for the received communications. The user/caregiver may activate the short range reading mode of the reader with a button or by other means. The marriage may also occur when the sensor is activated.

In one example of use, the caregiver first scans the patient's bracelet with a handheld scanner which includes the barcode scanner. The unique identifier of the patient is read into the system. The system then prompts for a sensor to be scanned. The caregiver scans one or more sensors with the handheld scanner which also includes a short range RF reader. The system then marries the identifiers for the patient and sensor.

The same methods above can be used for identifiers other than the MRN such as the name, date of birth, room, bed, etc.

In the case of the room or bed, the base station may be able to determine from signal strength or its read range what bed or room the sensor is in. For example, a base station may have sufficient read range only to receive data from sensors within a room or from a specific bed. Directionality of the base station reader may also be used to determine the location of a sensor. This directionality can be achieved with an antenna with greater directionality. One or more antennas can be used in a setting where there will be one or more patients per base station. A single antenna can vary its direction between communications. The user/caregiver can change the direction the antenna is pointing or the direction of its maximal gain on the base unit, where an indicator can show the antenna's direction. The system can then associate the bed or room number with data from a sensor or group of sensors. This marriage of sensor(s) to a specific room or bed may be sufficient for a given care facility to determine which patient is being monitor by which sensor(s).

The monitoring system of the present invention can track, record, and display relative surface pressure distribution data for a patient and alert caregivers when it's indicated to reposition a patient. Since the orientation sensor is placed in a known orientation relative to the patient (using visual indices and auto-orientation mechanisms), the system has the ability to know when pressure is being exerted on specific areas of their body. The system can also determine the cumulative amount of time that pressure has been exerted on specific areas of the body, and thereby calculate the pressure dose for specific areas of the body. The system can monitor the pressure dose at specific areas of a patient's body, and use this information to determine a patient's requirement for repositioning. The system can use this information to help ensure that patients are turned as often as necessary, but not more often than necessary. In addition, the system can suggest the optimal direction to reposition a patient by analyzing the pressure dose at specific areas of the patient's body and suggesting repositioning maneuvers that allow for the patient to be preferentially positioned onto regions of the body that have a low pressure dose.

Still further, the system that can automatically detect when a patient initiates a turn by themselves or if a turn is initiated by a care-giver. In an embodiment of this aspect, an RFID tag on the caregiver's badge configured to be recognized by the orientation sensor on the patient or by the base station residing near the patient. When the two (ID badge and patient sensor) come in close proximity with each other, and the system subsequently detects a patient turn, it can be noted that the turn was performed when a caregiver was present. Other methods for doing this include having a button on the sensor or user interface that is pressed to indicate a care-giver turn was performed; still others will be apparent to those skilled in the art, given the teachings herein. This information can be helpful, as it may be a factor that helps indicate when a patient is sufficiently mobile, and thus no longer requires continued monitoring and caregiver assistance. However, if a patient is determined to not be moving sufficiently on their own, it may indicate that this patient requires continued monitoring and caregiver assistance.

In another aspect of the present invention, the system not only keeps track of how long a user has been exerting pressure on specific areas of their body, but also keeps track of how much time specific areas of the body have had to depressurize. This is important because sufficient blood flow to a tissue (where it is free of pressure above a threshold that restricts blood flow), is required for a sufficiently long period of time in order to resupply said tissue with oxygen and vital nutrients. This is referred to as the re-perfusion interval. The desired re-perfusion interval can be set by the user, by caregivers, or can be taken from a protocol. The re-perfusion interval may also vary depending on the patient. For example, a patient's co-morbidities, Braden score, nutrition status, past history of pressure sores, or feedback from perfusion sensors can be used to determine an appropriate re-perfusion interval.

Knowing the patient's orientation relative to the support surface can be important for pressure ulcer management. When information regarding both the orientation of the support surface relative to gravity and the orientation of the patient relative to gravity is provided, the system can determine the relative normal force of the support surface (pressure) as well as the tangential force of the support surface (shear force).

Orientation/inclination sensors 1200 can be placed on the support surface to directly measure the orientation of the support surface as shown in FIG. 12. These can be placed, for instance, on the mattress, the bed frame, etc. These sensors can be the same or different from the sensors 1205 that are placed on the patient. These sensors can communicate with the same or different wired or wireless transceivers. By using different sensors for the support surface and the patient, or by using sensors with different unique identifiers, the system can easily distinguish between information sent from the support surface sensors and information sent from patient sensors. One or more support surface sensors can be placed on or they can be contained within the support surface. With one sensor, tilting of the support surface as a unit (eg. right, left, Trendelenburg, etc) can be measured. With more than one sensor, the orientations of different parts of the support surface can be determined, such as with tilting of the head of the bed.

Support surfaces can have embedded sensors that are used for determining its orientation and positioning. Data from these sensors can be used to provide our system with information regarding the orientation of the support surface. In such an embodiment, the host communicates with the components of the support surface, for example, embedded the processor(s) r or sensor(s), to gather this data.

Support surfaces have several common orientations and configurations. These include flat, head up, Trendelenburg position, reverse Trendelenburg position, rotated right, rotated left, combinations of these, etc. The orientation data for these common and possible support surface positions can be programmed into the system so that the orientation data does not have to be measured directly. A user can select which orientation the support system is in (including specific angles in some embodiments) and the system can use that data to determine the orientation of the patient relative to the support surface.

If information regarding the orientation of the support surface is not provided to the system, it can be interpreted that the support system is in a default orientation, such as horizontal to gravity.

Knowing the orientation of the patient relative to the support surface, and the orientation of the support surface relative to gravity, allows the system to generate an estimate of where on a patient's body surface pressure is being exerted, and an orientation-based surface pressure distribution map can be generated. This data may also be used to estimate the magnitude of the pressure per unit weight of the patient. Information regarding the weight and mass distribution of a patient can be used to estimate the absolute pressures being experienced at different regions of patient's body.

Figure 13:
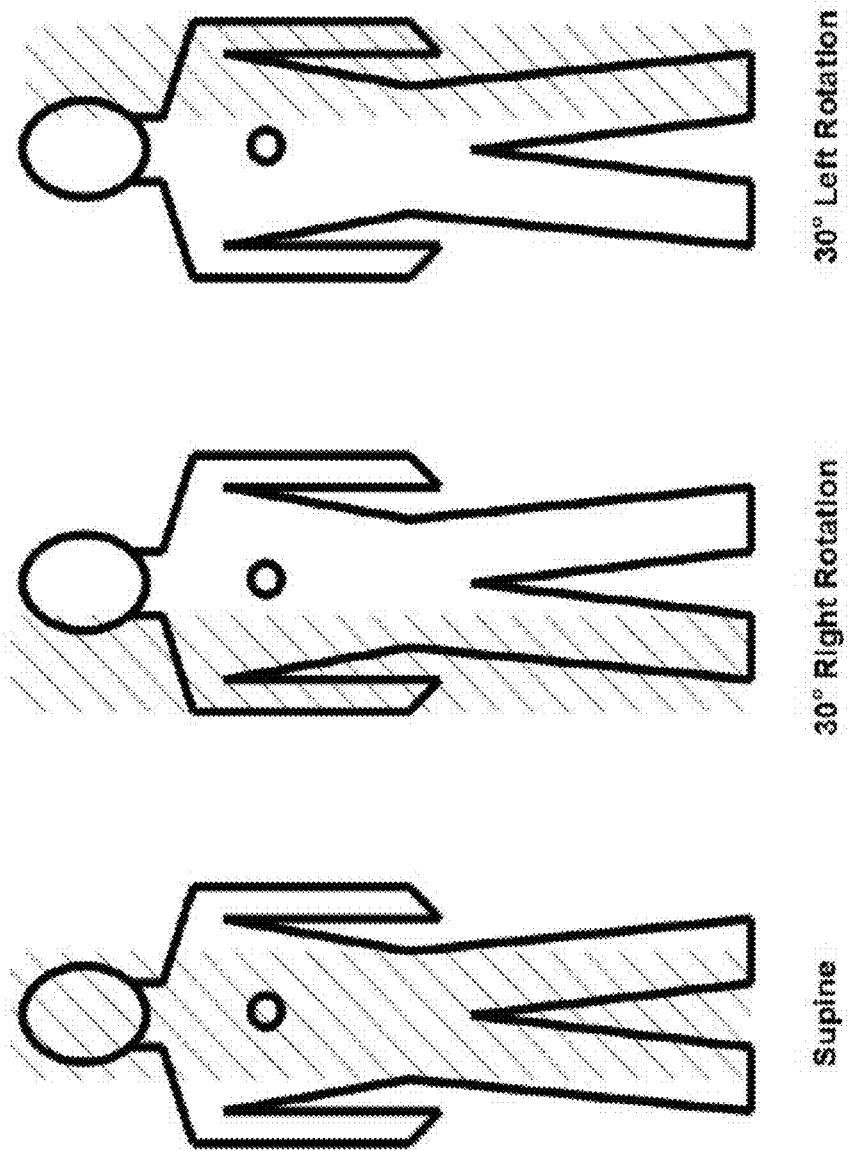
FIG. 13 illustrates a visual representation of an orientation based pressure map in three patient orientations: supine, right rotation, and left rotation.

At different angles of patient rotation relative to the support surface and to gravity, the patient experiences pressure on different portions of their body. This is the basis for the turning protocols, which allows for periodic depressurization of areas of the body in sequence. The system can determine, from the orientation of the patient relative to the support surface and to gravity, which areas of the body are experiencing pressure, and thereby creates an orientation-based pressure distribution model of the patient. A representation of the orientation-based pressure map is shown in FIG. 13. The system can also keep track of how long the patient is in any given position and thus how long certain areas of the body are experiencing significant pressure. As the patient is repositioned, the system can monitor the angle of patient rotation, and determine if there was a sufficient change in a patient's orientation, so as to provide a threshold level of depressurization at specific areas of the patient's body. For example, if the patient is insufficiently rotated, certain areas of the body may not experience depressurization. The system can monitor and track the pressure at different body regions using the orientation-based pressure distribution model. The system can determine when certain body regions require depressurization, and thus indicate that a change in patient orientation is required. In such a fashion, the system can optimize a patient turning schedule and ensure that patients are turned as often as necessary, but not more often than necessary. The system can also ensure that patients are turned with sufficient frequency and with sufficient de-pressurization intervals so as to provide sufficient time for tissue perfusion.

The orientation-based surface pressure distribution model determines the surface pressure distribution as a function of the patient's orientation relative to a support surface. When the patient is supine, surface pressure is distributed over the back of the patient. When the patient rotates onto their side, surface pressure is distributed along the corresponding side as a function of the angle of patient rotation.

An orientation-based relative surface pressure distribution model can be generalized without taking into account actual or absolute pressure estimates. However, the present invention can also incorporate a patient's weight, mass distribution, BMI, and other characteristics in order to estimate an orientation-based absolute surface pressure distribution model. Certain patients and/or caregivers may choose to calibrate orientation-based pressure distributions by going through a calibration procedure that can involve rotating at different angles and viewing pressure distribution using a pressure measurement device, such as a pressure mat.

Knowing the orientation of the patient relative to the support surface and the orientation of the support surface relative to gravity allows the system to estimate the shear forces acting on the patient, in addition to the normal force pressure. Shear force acts on the patient when the support surface is angled and there are forces acting tangential to the patient's skin. These shear forces contribute to tissue damage and minimizing shear force is important for pressure ulcer management and skin health.

Figure 14:
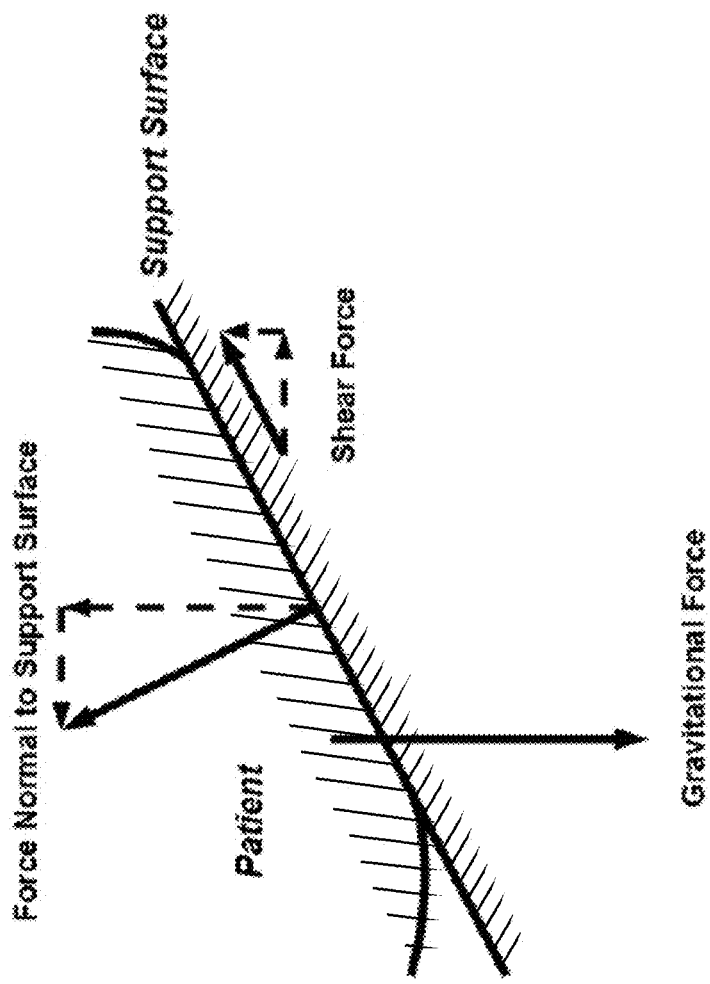
FIG. 14 illustrates the directions and certain orthogonal components of the gravitational force, normal force, and shear force experienced by a patient on an inclined support surface.

One method for estimating the shear force on a patient comprises determining the orientation of the patient relative to gravity and determining the orientation of the support surface relative to gravity. A processing device and corresponding algorithms then determine the orientation of the patient relative to the support surface. When the patient is static, the gravitational force acting on the patient is countered by the component of the normal force of the support surface that is in the opposite direction of the gravitational force vector and countered also by the component of the shear force that is in the opposite direction of the gravitational force vector. The directions of gravitational, normal, and shear forces are illustrated in FIG. 14, as well as their components parallel and orthogonal to the direction of the gravitational force, where the below relationships can be seen:

Gravitational force−Vertical component of normal force=Vertical component of shear force Shear force=Vertical component of shear force/sin (Angle of Inclination of support surface)

Thus, the angle of the support surface gives a measure by which we can determine the relative magnitude of shear forces acting on the patient. Knowing patient specific data, such as the weight of the patient, can allow an estimation of the absolute magnitude of the shear force.

The estimate of the shear force can be combined with the orientation-based pressure map and the support surface orientation data to provide an estimate of where the shear force is acting. The tissue areas that are receiving pressure are also areas that may be subjected to more shear force. The magnitudes of pressure and shear force for any given area of tissue can be correlated. This information can be used to create an orientation based shear force map. The system can use this data to adjust its repositioning recommendation in order to minimize shear force damage. For instance, the amount of time a given area receives shear force or a magnitude of shear force experienced can be measures that the system attempts to minimize or limit.

The single sensor or sensors positioned only on the patient can be used to determine the orientation of the patient relative to the support surface and to gravity. For example, any sustained inclination in the x-z plane as defined in FIG. 5A can be interpreted as an inclination of the bed. Through an analysis of the orientation with respect to gravity, over time, of a single sensor placed on a patient, support structure orientation can be determined for structures having more flexible configurability.

The present invention also permits automation of various parameters typically used to calculate a patient's Braden score. At present, some of these parameters are taken subjectively. However, the present invention permits some of these parameters to be determined much more objectively, and with automated data entry into the patient chart, the monitoring system, the support surface, or any associated data storage unit. The parameters that are assessed subjectively by the prior art, but which can be objectively assessed using the monitoring system described herein, include the patient's mobility level, activity level, moisture level, and any friction and shear forces experienced by the patient. The mobility and activity level can be measured by the sensor unit as described above. With the addition of a moisture sensor, the unit can also provide an objective assessment of the skin moisture level. The acceleration of the patient relative to the support surface, as described above, can also be analyzed to determine the magnitude of any friction and shear forces experienced by the patient. The ability of the patient to move without sliding can be determined by the accelerations experienced by the accelerometer. Integrated accelerations to determine cumulative distances moved, and the addition of gyroscopes and/or magnetometers can help determine friction/shear forces experienced by a patient. While the two remaining variables that comprise the Braden score, (i.e. nutrition status and sensory perception) can not be measured by the monitoring system described herein, these variables are much less likely to change frequently and they can more or less be considered constant. Thus, once information regarding the patient's nutrition status and sensory perception are provided to the system, the system can thereinafter automatically and objectively determine a patient's Braden score in real-time.

With the improved monitoring of patient repositioning and surface pressure distribution data, it is possible to better assess the effectiveness of a turning protocol. Whereas many current protocols suggest turning every two hours, this may not be the best protocol for all patients. For example, certain patients with existing wounds, poor nutrition, poor wound healing, etc, may require more frequent turning. Certain patients, with better health and fewer wounds may require less turning, allowing for better rest and reduced caretaker involvement. Improved monitoring can be invaluable for facilities who want to assess the effectiveness of the turning protocol. The present invention can also include features which allow for active data collection to automatically suggest variations in the turning protocol. In an embodiment, the system can use data about the patient, such as the Braden score or components that affect the Braden score of a given patient. Other useful data includes the presence of wounds, pressure ulcers, history of pressure ulcers, etc. Data about pressure ulcer development and progress, such as healing or worsening, can also be entered. Depending upon the embodiment, the present invention can adjust the suggested turning regimen based on how well a patient is doing on the current regimen or how well the patient has done in the past on a turning regimen. The invention can also allow for minor adjustments in the turning regimen and use data about the progress to determine which regimens are better. Changes in regimen can include, but are not limited to, frequency of turns, time spent in a given position, time that certain areas of tissue spend in depressurized states, orientation angle, amount of pressure and time spend on wounded or previously wounded areas, etc. In some embodiments, additional sensors and data can be used to assess the progress, including perfusion sensors, area and depth measure of the wound, stage of wound, etc. Data can be collected from more than one patient, for example patients within a facility or ward or in fact all patient to help assess the performance of and determine potential improvements for care protocols.

A pre-existing pressure ulcer or other wound, may be more easily damaged by pressure and shear forces. Part of the treatment for that ulcer or wound may be to reduce the maximum pressure experienced by the damaged tissue and surrounding tissue and/or to reduce the amount of time that pressure is exerted on the tissue. Similarly, the treatment may include limiting the amount of shear force experienced by the tissue.

In another aspect of the present invention, the locations of existing pressure ulcers, wounds, and other pressure-sensitive areas of the body can be identified and entered into the monitoring system. The threshold amount of time that pressure can be exerted on the pressure-sensitive region can be adjusted, as well as the depressurization interval desired. In some instances, it is desirable to have no pressure on an area of damaged tissue, since the pressure appropriate for wounds such as pressure ulcers, incisions, skin flaps, etc., is much less than that for healthy tissue. In such a scenario, if it is determined that pressure is being exerted on an area of damaged tissue, the system can set off an alarm to inform the patient and/or caregiver(s) to adjust the position so as to depressurize the wound area. In addition to wounds, the system can also be configured to permit entry of any other areas that require surface pressure monitoring. These areas can include shoulders, hips, feet, etc. The user/caregiver can enter the location in many ways, some examples including: a pull-down menu of wound sites, a text entry, a graphical interface with a graphical representation of the patient in 2D or 3D, etc. These are described in more detail below. In addition, different sensors can be pre-programmed for use at specific body regions. The pre-programmed sensors can contain information about the location at which they are meant to be placed and/or contain specific pressure thresholds, depressurization interval thresholds, or other care data.

The user or caregiver can manually enter the locations of the wounds. One method of entry is to show a 2D (from one or more views, eg posterior, anterior, L lateral, R lateral) or 3D model of the patient (or a generalized patient, perhaps chosen from a list to closely match the patient) and have the user select the locations where the pressure ulcers or other wounds are present on the model. This model can be represented on a computer display with a mouse or touch-screen interaction to allow for location selection. Selections on a 2D model can be mapped to a 3D model of the patient.

Another method includes choosing from common or possible locations for pressure ulcers, such as: ischial tuberosity, trochanteric, sacral, malleolar, heel, patellar, pretibial, nose, chin, forehead, occiput, chest, back, and elbow locations. If the location of the wound falls outside of the list and no entry approximate sufficiently the location, then the user may enter locations relative to the entries, eg 2 cm @ 3 o'clock direction from patellar location.

The user may choose from one or more entry methods depending on what is more appropriate and efficient. The user can also enter details about the pressure ulcer including stage, size, shape, depth, age, skin care details, etc. Depending upon the embodiment, the system can also self-populate data on wound and ulcer locations based on the chart, which can be later adjusted by the user. In other embodiments, sensible markers can be placed on the patient to designate the location of the wounds or ulcers.

Using the location of the wounds and ulcers, the treatment can be personalized. In an automated treatment/prevention bed, for instance, pressure can be reduced at the location of the wounds and different pressure varying modes can be used. For recommendations of repositioning regimens, the recommendations can reduce the amount of time the patient may spend on locations of wounds or ulcers. If positing on an existing wound or ulcer in unavoidable, embodiments of the present invention can take into account the relative severity or risk of deterioration of the different ulcers, which can, for example, be entered by the user, to determine which ulcers/wounds it preferentially avoids.

Several features can exist in the present embodiment that make the sensor less expensive to manufacture and thus more amenable to being disposable. One such feature is that only the electronics and circuitry needed to fulfill the duties of the sensor can be included in the design. In one simplified embodiment, the main components can include only an accelerometer, A/D converter, microprocessor, RF transceiver, and antenna, with many of the desired features, including basic physiological signal monitoring, covered by the these components. In some embodiments, a 3-axis accelerometer can be replaced by a 2-axis accelerometer. The microprocessor need not be powerful in all embodiments, where much of the computation is configured to take place on the host system. Also, one or more components can be included on a single chip, for example a chip with a microprocessor, A/D converter, and RF transceiver, or a chip with all of these plus the accelerometer. Such an embodiment can signficantly reduce the cost and/or size of the sensor. Again depending upon the embodiment, the battery, or other energy storage unit like a capacitor, can be disposable rather than rechargeable. This can reduce the size and cost of the energy storage unit. The sensor battery can also be designed to operate until it is greatly discharged, which allows for a greater amount of usable energy for the same energy capacity storage but is less amenable to a rechargeable unit. As well, with a non-rechargeable unit, the electronics and circuitry needed for recharging, including leads or an inductive loop or antenna, can be left out of the sensor.

The system can be used to monitor patients that are receiving vibration or percussion therapy. Often, patients with lung disease will require regular vibration/percussion therapy to help clear mucus and secretions from their airways. The sensors described herein can detect vibration of the chest wall. The monitoring system can be used to quantify the magnitude of vibration/percussion therapy, the session length of time, and the frequency of sessions. The monitoring system can be used to help coordinate vibration/percussion therapy for patients. If a patient is not receiving adequate vibration/percussion therapy, caregivers can be alerted via an alarm mechanism. The monitoring system of the present invention can also provide feedback to devices used for automated means of vibration/percussion therapy. The force of vibration/percussion therapy produced by an automated source (such as a bed) can be regulated based on data from the sensor placed on the patient in accordance with the present invention.

The sensing system described in the present invention can be used to monitor patients that have been prescribed an incentive spirometer. Many hospitalized patients are encouraged to use an incentive spirometer to help prevent atelectasis and improve lung function. As previously discussed, the sensors described herein can detect acceleration of the chest wall. The monitoring system can be used to quantify the magnitude of incentive spirometry therapy, the session length of time, and the frequency of sessions. Statistics regarding a patient's incentive spirometer usage can be provided to both the patient and caregivers. If a patient is not receiving adequate incentive spirometry therapy, caregivers can be alerted via an alarm mechanism. The sensing system described herein can be used to assess compliance with, and adequacy of, prescribed incentive spirometry regimens.

In an embodiment, the monitoring system comprises a sensor affixed to a patient whereby the sensor data is wirelessly transmitted to one or more signal receiving stations. The receiving stations can be placed at fixed and known locations, such that the approximate location of monitored patients can be determined by triangulation, received-signal-strength-indication (RSSI), time-delay of transceived EM signal, or other means known in the art of real-time location tracking.

In an embodiment, the present invention can be used to identify patients that have fallen while attempting to exit a bed or chair. The sensor in such embodiments can detect sudden accelerations and/or decelerations of monitored patient. If the monitoring system of the present invention detects a possible patient fall, caregivers can immediately be alerted via an alarm mechanism.

The sensing system can be used to detect when, and how often, patients get out of bed. It is common practice to encourage hospitalized patients to get out of bed frequently. Getting patients out of bed and walking around can help prevent hospital-related complications, such as pressure ulcers and deep venous thrombosis (blood clots). The sensors described herein can determine how long a patient is out of bed, how far they travel, and how fast a patient walks. If a patient is not getting out of bed or walking sufficiently, caregivers can be alerted via an alarm mechanism. The sensing system can objectively assess a user's level and adequacy of ambulation.

Additional sensing elements for detecting other physiologic characteristics can be attached to or incorporated within the sensor 300 in addition to the one or more accelerometers and RF units previously described. One such sensor is a pedometer. This can be used to track the number of steps a patient takes or the amount of movement he/she engages in. The data from the pedometer can be sent in conjunction with the data from the accelerometer. As previously mentioned, electrical leads can be incorporated to monitor the heart or other muscle activity. Likewise, capacitive sensors or piezo-electric sensors can be incorporated to detect heart sounds, breathing sounds, or other vibrations. Similarly, a pulse oximeter can be incorporated to provide oxygenation data, and a temperature sensor can provide temperature monitoring.

Since the sensor 300 is, in at least some embodiments, powered by a battery or similar device, it is desirable in some embodiments to conserve power. Aspects of the present invention include power management, including burst data transmission, either at regular intervals or in response to a predefined trigger. Portions of the sensor can be powered down when not needed, including the transceiver, microprocessor, sensors, etc. In an embodiment, the sensors can be used for a period, then powered down, and still successfully monitor heart rate and breathing. Capacitive and temperature sensors in some embodiments may need only one reading between power downs.

Low power states can be indicated in a variety of ways, including flashing, varying intensity on a display, different response when interrogated, and transmission of battery information or "I'm alive" information.

As discussed previously, in some embodiments it can be desirable to be able to remove the sensor from the backing affixed to the patient. In such circumstances, it is desirable both to ensure that the orientation relative to the patient is maintained, and also to ensure that the new sensor is secure, an asymmetric relationship between the backing and the sensor can be used, together with any suitable locking mechanism. In other embodiments, the relationship between the sensor and backing may not be fixed, but automatically sensed indicators such as electrodes, reflective patches, etc., can be used to inform the system of the new relative position.

While the foregoing discussion has described an accelerometer-based sensor in detail, other sensors are also accepted, as discussed previously. Thus, referring next to FIGS. 15A-15B and 16A-16B, resistive sensors in accordance with the present invention can be better appreciated.

In an embodiment of one aspect of the present invention, a support surface that contains a plurality of air columns is embedded with an array of sensors that can detect the presence of surface markers, although a single sensor works in at least some embodiments. Surface markers can be placed on areas of the body that are most susceptible to developing pressure sores, such as the hips, heels, and sacrum. Surface markers can also be placed on areas of the body that are resistant to developing pressure ulcers. Surface markers can also be incorporated into garments, such as socks or underwear. Other wearable items such as bracelets or belts can incorporate surface markers. Surface markers can also be incorporated into wound dressings, which are then placed over injured tissue. Specific areas of the user's body can also be demarcated using a sensible ink pen. The support surface can be programmed to optimize surface pressure beneath surface markers. The support surface can also be programmed to perform pressure modulating maneuvers at areas corresponding to surface markers. The pressure modulating maneuvers can be used to encourage blood flow to areas corresponding to surface markers, and can be varied over both space and time. Therapeutic measures can also be targeted to areas corresponding to body surface markers. Therapeutic measures can include light therapy (including infrared, near-infrared, or low-level laser light), ultrasonic therapy, electromagnetic therapy, or other therapies. Targeting energy (heat) to areas corresponding to body surface markers may cause local blood vessel dilatation, and thus promote blood flow to those specific areas. Therapeutic measures can be derived from within the support surface, or they can be external to the support surface.

In another embodiment of the present invention, a support surface that contains a plurality of air columns is embedded with one or more sensors, such that the perfusion status of the user can be determined at discrete locations on their body. The tissue perfusion map generated by the sensor array can then be used to identify areas of compromised tissue perfusion. The support surface can use the tissue perfusion map to optimize pressure distribution and reduce or eliminate surface pressure at areas identified as having compromised tissue perfusion. Depending upon the implementation, the pressure within one or more air columns can automatically decrease at areas correlating to compromised tissue perfusion, thereby decreasing surface interface pressure at these locations.

In another embodiment of the present invention, if tissue perfusion cannot be optimized automatically by the support surface, caregivers can be alerted. Caregivers can then manually optimize the surface pressure distribution of the patient to prevent tissue damage. With such a method, caregivers can monitor the perfusion status of a patient. The system can be programmed to automatically alert caregivers of any areas that register potentially impaired or compromised tissue perfusion.

The support surface can utilize one or more sensors to determine the physical presence of the user and/or locate specific areas of a user's body (which could be demarcated by wound dressings or other surface markers). Depending upon the embodiment, sensors can also be used to determine the perfusion status, orientation, and other biometric data of the user. The sensors can be embedded within the support system, or can be external to the support system. Depending upon the particular implementation, types of sensors that can be used in these aspects of the present invention include, but are not limited to, resistive, capacitive, inductive and magnetic sensors. Reflective, RFID, infrared, pressure, and stress sensors can also be used in some implementations. Likewise, transcutaneous $CO_2$ sensors, hydration sensors, pH sensors, ultrasound sensors and remote optical spectroscopy sensors can also be used in certain implementations. Each of these is discussed briefly, below.

Figure 15A:
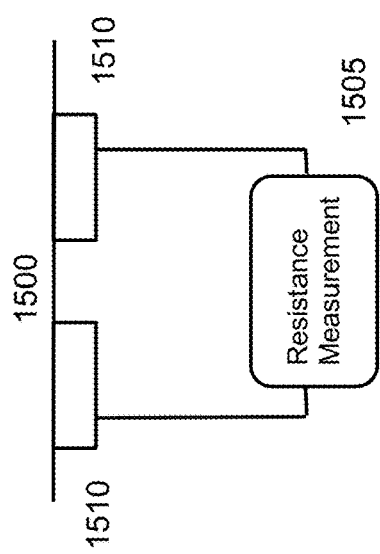
FIGS. 15A-15B illustrate the operation of a resistive sensor in accordance with the present invention.
Figure 15B:
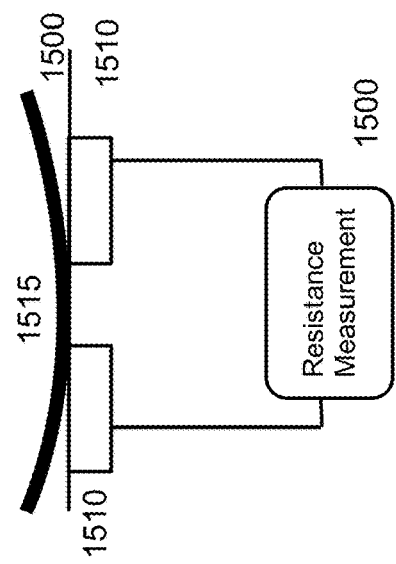

Resistive sensors can be used to sense the presence of a user, or discrete areas on a user's body, as shown in FIGS. 15A-15B. In this aspect of the invention, the resistance between two electrodes is continuously monitored. The entire user, or discrete areas on a user's body, can be covered in a material that has a known resistance. When this material comes into contact with the resistive sensors that are embedded into the support system, a measurable change in resistance occurs. This measurable change in resistance can be used to identify the presence of the user. A computer can be used to synthesize data from multiple resistive sensors in order to generate a physical location map of the user. This map can be used to show the location of the entire user (or discrete parts of the user) in relationship to the support system.

The resistance of the material that is used to cover the user must be sufficiently different from the intrinsic resistances sensed by the sensors of the support system when the user, or material worn by the user, is not present. The intrinsic resistance of the support system can be due air, bedding, plastic, etc. The resistance of the material that is used to cover the user can be of lower or higher resistance than the intrinsic resistances sensed.

In one implementation of this method, a sensing system can be designed with one or more resistive sensors placed across its surface. The user wears clothing embedded with low or high resistance fibers, or a body surface marker with low or high resistance properties is placed over a specific area of the user's body. When the low or high resistance material comes into contact with the resistive sensors of the sensing system, the resulting increase or decrease in resistance is measurable, and can be used to identify the presence of the user or discrete areas of the user's body.

Multiple different materials with differing resistances can be placed on the user in some embodiments. With such a method, the materials of differing resistances can be used to demarcate specific areas of the user's body. For example, if a user had several different wounds, each wound is covered in a wound dressing that had a different resistance. When the wound dressings come into contact with the sensing system, the resulting changes in resistance can be used to determine the location of each wound in relation to the support system of the present invention. Being able to differentiate between different wound sites or different regions of the body also allows embodiments of the present invention to adapt differently to the different sites. For example, there may be different maximum pressures allowed at each site or different methods of varying the pressure at each site. Another usage is to have the materials of different resistances placed on different parts of the user's body, which allows embodiments of the present sensing system to locate and differentiate between different body parts. This can be used, for instance, to improve the mapping of the user with respect to the support system. Note that the ability to differentiate between different regions of interest, and allowing for different actions to be taken once the regions are differentiated, can be applied for other sensing modalities as well that allow for markers that can be differentiable. Here different resistances are used, but different capacitances, RFIDs, and other differentiable markers can be used.

It should be noted that the user does not necessarily need to be covered in a resistive material in all embodiments of the invention. If the intrinsic resistance sensed by the system in the absence of the user was sufficiently different from the resistance sensed when the user's skin or clothing was in contact with the sensing system, then no special covering on the user is necessary. In such a method, the skin or clothing interacts with the resistive touch sensors of the sensing system, and causes measurable changes in resistance. A user location map can then be generated to identify all locations where skin or clothing was in contact with the sensing system.

The system can be designed to accommodate for bed sheets, clothing, or other materials potentially intervening between the resistive sensor and the object to be sensed.

In FIG. 15A, one embodiment of a resistive sensor is shown. The resistive sensor 1500 is embedded into the support surface 1505 and the resistance between two leads

1510 is measured. The resistance between the leads changes when the patient 1515, or a marker material with a different resistance, is placed between the leads. The change in resistance is detected by the resistive sensor, and this information is sent to a computer for integration with other sensor data.

Figure 16A:
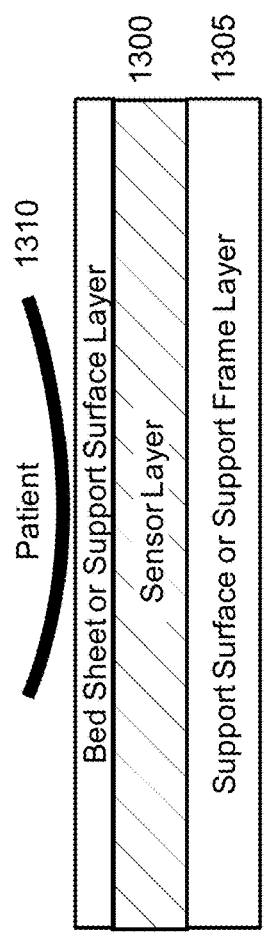
FIGS. 16A-16B illustrate the operation of a sensor layer such as might be used with resistive, capacitive, inductive or magnetic sensors in accordance with the invention.
Figure 16B:
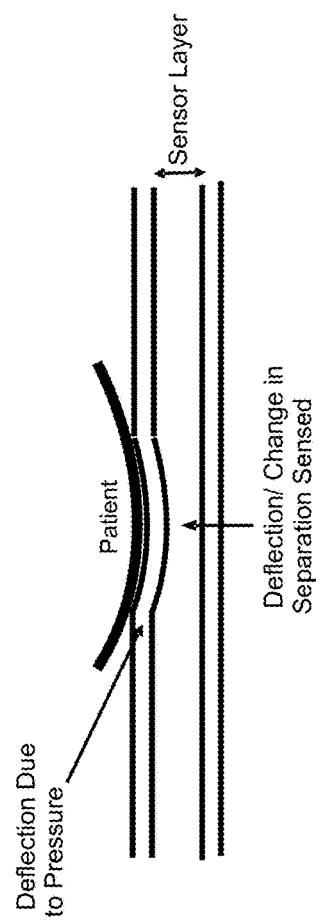

In another embodiment, shown in FIGS. 16A-B, resistive sensing can be implemented in the form of a pad 1600 which incorporates a resistive touch technology similar to that found in some touch sensitive displays. In such an embodiment, nothing needs be placed against, worn by, or applied to the patient. In an embodiment, such a pad covers the support surface 1605 or can be placed within or beneath the support surface (assuming that pressure due to the presence of a patient is effectively transmitted through the support surface) and comprises two resistive layers 1610 and 1615 vertically separated, such as by an array of small dots or columns. Pressure from the patient 1620 laying on the pad results in the touching of the two layers, from which the location of the applied pressure can be determined. In an alternative arrangement, a plurality of resistive pads can be used, where each pad permits the pressure applied by the patient to be better quantified and resolved. Body parts causing the regions of contact can be identified through software adapted to recognize pressure distributions, which allows the orientation of the patient to be determined, as well as the magnitude of the pressure applied by the various body parts.

An alternative method that can be used to sense the presence of a user, or a discrete area on a user's body, is to use capacitive touch sensors. Here, an electrode can sense the body's capacitance. In such a method, one or more capacitive touch sensors can be used to determine the location of the user in relation to the support system. In an embodiment, the user can also wear a material with a known capacitance, which can then be detected by the capacitive touch sensors. Specific areas on the user's body (e.g. wound areas) can also be demarcated using materials with different capacitances. By strategically placing materials with differing capacitances over a user's body, a physical location map of the user can be generated. When multiple different materials are used (with each having a different capacitance) the capacitive touch sensors can be used in combination to differentiate between discrete areas on the user's body. When used in such a manner, specific areas on a user's body can be "tagged" and surface pressure can be independently regulated at each tagged location. This is important for the management of a user with multiple wounds, where each wound may have a different maximum pressure threshold.

Capacitive sensors can be used in a manner similar to resistive sensors, as described above. As with resistive sensors, capacitive sensors need not be placed against, worn by, or applied to the patient to be effective. The capacitive sensors can be incorporated into a pad, as described previously. Likewise, multiple body regions can be identified and their localized contact pressure can be quantified by measuring the capacitance resulting from the patient's proximity to the sensor. Depending upon the implementation, one or a plurality of sensors may be desired.

Inductive sensors can also be used to detect the presence of a user, or discrete areas on a user's body. These sensors use an induction loop to generate a magnetic field. The inductance of the loop can be changed by the presence or absence of nearby metallic materials, which can be placed on the user. For example, the user can wear clothing that is embedded with a metallic material, or an adhesive surface marker can be embedded with a metallic material, or a wound dressing can be embedded with a metallic material. Materials that have different inductive properties can be placed on the user's body at strategic locations. Such a method allows the inductive sensors to differentiate between different locations on the user's body, thereby generating a physical location map of the user.

Inductive sensors can be used in a manner similar to resistive and capacitive sensors, as described above.

Magnetic sensors also allow for non-contact sensing, and can utilize a magnetoresistive effect, a Hall effect, magnetic attraction, or any other means known in the art for measuring magnetic field magnitude and/or direction. One or more magnetic sensors can be used by the sensing system to detect the presence of magnetic materials in proximity to the support system. Specific areas of the user's body, or the user's entire body, can be demarcated by wound dressings, surface markers, or clothing that has been embedded with magnetic materials. Specific areas of the user's body, or the user's entire body, can also be demarcated using a magnetic ink pen or any other marking capable of being magnetically sensed. The sensing system can then detect the magnetic field strength and/or magnetic field direction created by the magnetic materials to detect the physical presence of a user and/or locate specific areas on a user's body and/or detect any movement of the user relative to the support system. The magnetic sensors can measure the magnetic field strength and/or the magnetic field direction produced from any magnetic materials placed in proximity to the sensing system. There may be some advantages to measuring magnetic field direction versus magnetic field strength, which include: insensitivity to the temperature coefficient of the magnet, less sensitivity to shock and vibration, ability to withstand larger variations in the gap between the sensor and the magnet, and the ability to detect angular or linear movement of magnetic objects. The support system can be programmed such that pressure relieving or pressure eliminating maneuvers are performed at or around areas demarcated by magnetic materials placed on the user's body. The support system can also be programmed such that pressurization/depressurization sequences are preformed at or around areas demarcated by magnetic materials placed on the user's body. Such a method can be used to encourage blood flow to specific areas of a user's body.

It will be appreciated, from the discussion of resistive, capacitive and inductive sensors, that magnetic sensors can also be placed in a mat covering the support surface, and which has, for example, two layers where the applied pressure from the patient moves the layers together in a way that can be measured resistively, capacitively, inductively, or magnetically, without requiring special clothing or wound dressings or other markers.

A variation of the location markers is that the markers can contain a reflective or retroreflective material and a light sensor can detect light reflected from the marker. The sensor can be located next to a light source, for example an LED. When the marker is positioned in such a way that the light from the light source reflects back from the marker it can be sensed by the light sensor.

Another variation of the location sensor is using RFID and radio frequency triangulation. The position can be sensed using RFID by having sensors with a small and/or directed volume in which the sensors are able to detect the IDs. Having one or more RFID sensors in known positions will allow the sensing system to gain information about the RFID tags once they are in the range of the sensors. The RFID tags can be embedded in body surface markers. An array of sensors on the sensor system that detects the RFID tags imbedded in body surface markers and wound dressings is one possible implementation. Alternatively, radio frequency communication between tags and readers can be used to triangulate the location of the tags.

Infrared (IR) sensors can be used to detect the radiant heat of a user in some embodiments. In one implementation of this approach, a sensing system has one or more infrared sensors placed across its surface. Alternatively, the IR sensors can be placed below the surface of the support system, where all material between the user and the sensor allows infrared radiation to pass through it sufficiently to obtain an accurate reading. Alternatively, the IR sensors can be placed external to the support surface, where there is sufficient line-of-site with the user. Such a method allows for the remote detection of a user's radiant heat. Thus, infrared sensors can be used to measure the skin surface temperature over a large area without directly contacting the skin. By identifying all locations within the support system that are transmitting IR radiation, the physical location of the user relative to the support system can be determined.

The use of infrared sensors is an established and reliable method for indirectly measuring skin perfusion. Infrared sensing of the user's body can provide useful information regarding the temperature of the user at discrete locations on their body. Temperature mapping, also known as thermography, can be used to identify locations on the user's body that have abnormal thermal characteristics. When tissue becomes ischemic, there is a measurable drop in skin surface temperature. Thus, skin temperature is a marker for perfusion, and abnormal changes in skin temperature may indicate perfusion abnormalities within tissues. Both the absolute temperature of the skin, and temperature changes over time ($\Delta T$) can be used as markers for perfusion abnormalities. To determine the $\Delta T$ at discrete areas on the user's body, the thermal map of the user must be correlated to a physical location map of the user. Correlation of the physical location map of the user with other biometric data can be performed in the manner previously described. Since skin temperature variations are known to correlate with perfusion abnormalities, interface pressure can automatically be relieved at areas registering abnormal temperatures. Such a method can be used to optimize the user's perfusion status. Infrared sensors can comprise a two-dimensional array of discrete sensors such as semiconductor photodiodes, bolometric detectors, or other temperature sensors known in the art. Alternatively, a thermal imaging camera having a CCD or other two dimensional imaging sensor can also be used.

Pressure sensors can be used to detect both the physical presence of the user, and indicate areas of potentially compromised tissue perfusion. As surface interface pressure increases, the probability of compromising tissue perfusion also increases. Sustained surface pressures above 32 mmHg have been shown to correlate with impaired blood flow, and thus greatly increasing the risk of tissue necrosis.

Pressure sensors can be used in conjunction with other sensors to optimize pressure distribution over the entire support system.

The critical interface pressure threshold may vary between different locations on the user's body. For example, areas corresponding to wounded tissue may not tolerate any surface pressure. Tissues overlying bony prominences may have relatively low surface pressure thresholds. Tissues overlying thick layers of fat or muscle may tolerate relatively high surface pressures. To assign different surface pressure thresholds to specific locations on the user's body, the sensing system needs to be able to correlate user position and surface pressure data. Further description on how to correlate the physical location map of the user with other biometric data is contained herein.

In an embodiment, the pressure distribution map of a user can also be analyzed to determine the position/orientation of said user relative to the support surface. In such a fashion, the pressure at distinct regions of the patient's body can be determined.

A stress sensor can be used in some embodiments to measure the stress applied to the support surface due to the pressure created by the user's body. Some examples of stress sensors are strain gauges or piezoresistors or resistive fabrics/threads that change resistance upon stretching. Stress sensors can be placed on the surface of the sensing system, or within the walls of the sensing system. The stress sensors can also be placed in a sheet or mat that overlies the support surface. The stress sensors will stretch or compress as a function of the externally applied pressure due to the user's body weight. The stress sensors can also be placed directly on the user's body to measure skin stretch or compression. In addition to estimating pressure, the stress sensors can be used to gather data about shear stress. The data from the stress sensors can be used both to determine the physical location of the patient and to help identify areas of potentially compromised perfusion due to increased pressure or shear forces.

Transcutaneous oxygen pressure ($TcPO_2$) sensors can be used in some embodiments both to detect the physical presence of the user and to indicate areas of potentially compromised tissue perfusion. The $TcPO_2$ is a noninvasive method for assessing the perfusion status of a user. The $TcPO_2$ is related to the degree of ischemia, with decreasing oxygen pressures indicating areas of compromised tissue perfusion. The $TcPO_2$ is considered to be a sensitive and reliable determinant of a user's perfusion status.

$TcPO_2$ sensors can be placed on the patient or on the support surface. The transcutaneous oxygen pressure can also be measured remotely, as described later in this document.

Similarly, transcutaneous carbon dioxide pressure ($TcPCO_2$) sensors can be used in an embodiment both to detect the physical presence of the user and to indicate areas of potentially compromised tissue perfusion. $TcPCO_2$ monitors offer a non-invasive method of continuously measuring carbon dioxide tension. The $TcPCO_2$ is related to the degree of ischemia, with increasing carbon dioxide pressures indicating areas of compromised tissue perfusion $TcPCO_2$ sensors can be placed on the patient or on the support surface.

In an embodiment, hydration sensors can be used both to detect the physical presence of the user and to indicate areas of potentially compromised tissue perfusion. The assessment of tissue hydration can be used to detect dehydrated or edematous tissue. The hydration status can also be measured remotely, as described .later in this document.

The pH at discrete locations on the user's body can be detected remotely using a near-infrared light sensor in some embodiments. This technique can be used to accurately detect small changes in the pH of subcutaneous tissues. This technology works by detecting the difference in absorbance between protonated and unprotonated molecules. As tissue becomes ischemic, the acid content increases, and the ratio of protonated to unprotonated molecules increases. Thus, an increase in protonated molecules correlates with impaired perfusion, and the support system can automatically offload pressure at areas identified as having impaired perfusion.

Ultrasound can be used in some embodiments as a sensing modality to gather physiologic data from the user. This data can be used alone, or in combination with other sensing modalities, to assess the perfusion status of a patient at discrete locations on their body. Doppler ultrasound can also be used to assess blood flow. If areas of abnormal perfusion are detected, the support system can automatically optimize surface interface pressure at those locations, and caregivers can be alerted. Pressure optimizing maneuvers performed by the support system can be used to promote blood flow to critical areas.

In some embodiments, tissue oxygen tension, carbon dioxide tension, pH and hydration status can be analyzed remotely using near-infrared optical spectroscopy. The skin is a relatively weak absorber of near-infrared light, so near-infrared spectroscopy can be used to analyze the epidermis and dermis. Near-infrared spectroscopy can be used to examine spatial and temporal changes in tissue hemodynamics and can provide pre-clinical detection of perfusion abnormalities. When perfusion abnormalities are detected, the support system of the present invention can automatically redistribute pressure away from areas of compromised tissue perfusion.

Hemoglobin has distinct absorption bands in the near-infrared spectrum, depending on whether the heme group is oxygenated or deoxygenated. When tissue is exposed to near-infrared light, the chromophores within the tissue (such as oxygenated and deoxygenated hemoglobin) will absorb light at distinct wavelengths. Thus, the light that is ultimately reflected off of the tissue will contain wavelengths of light that were not absorbed by the chromophores. Oxygenated hemoglobin absorbs near-infrared light strongly in the 900-950 nm range, while deoxygenated hemoglobin absorbs near-infrared light strongly in the 650-750 nm range.

Water is the major component in tissue, and it absorbs near-infrared light most strongly at wavelengths above 900 nm. The absorption characteristics of water are distinct from hemoglobin, so water can be analyzed independently of hemoglobin. Therefore, in some embodiments, near-infrared spectroscopy can provide information regarding tissue hemodynamics, in addition to information regarding tissue hydration and water content. Such a method also allows for the detection of subclinical edema or swelling.

Figure 17B:
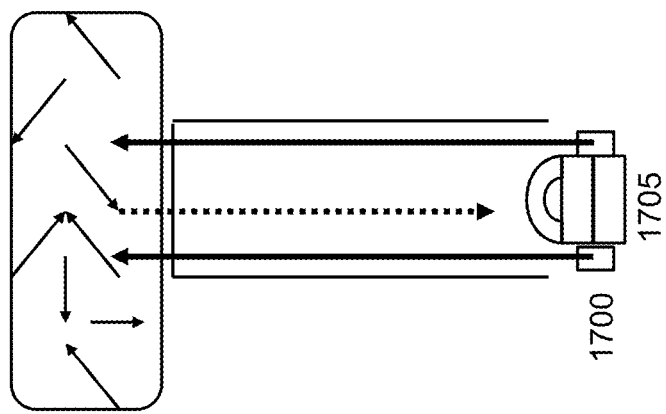
FIGS. 17A-17B illustrate an infrared sensor or other light sensor in accordance with an aspect of the invention.
Figure 17A:
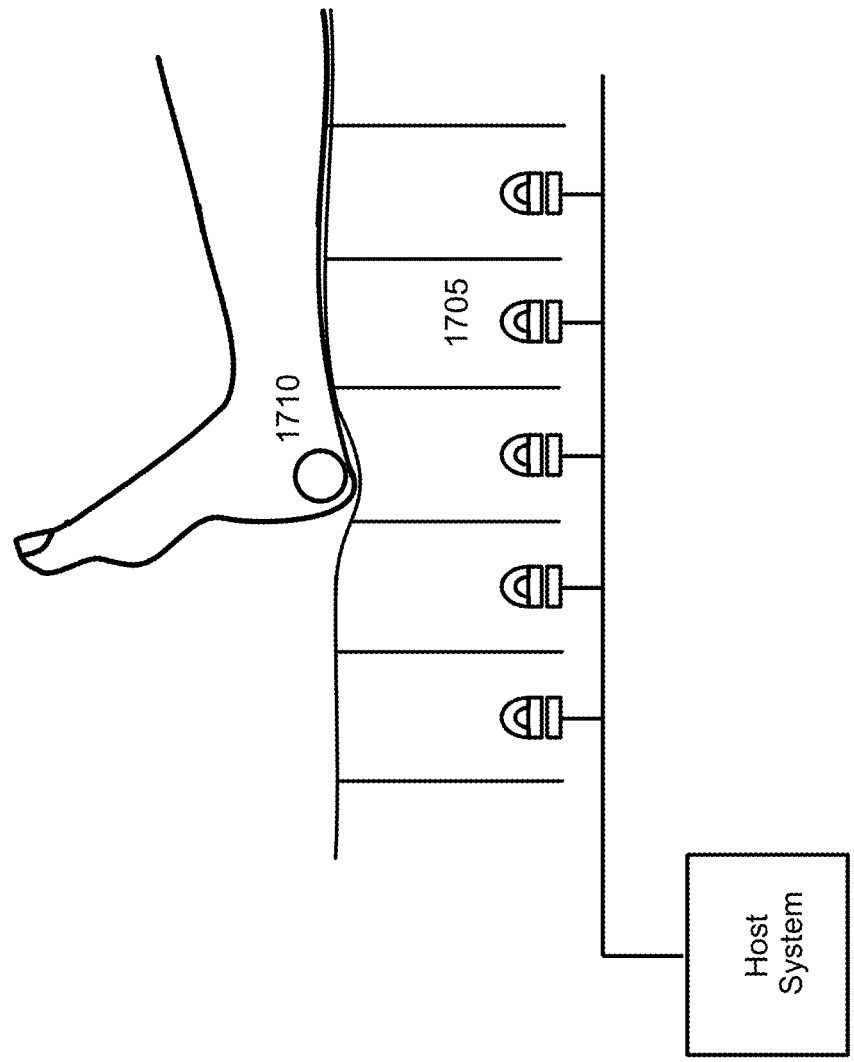

With the use of near-infrared spectroscopy, as shown in FIGS. 17A and 17B, a perfusion map of the patient can be created. One or more near-infrared light sources 1700 are used to analyze multiple physiologic processes such as TcO2, pH, and temperature. One or more infrared sensitive cameras 1705 can be used, placed sufficiently proximate to but separate from the light sources so as to receive reflected light from the patient without receiving bleed-over from the light sources. The support system then optimizes surface pressure based on the tissue perfusion map. The support system can use the data from the perfusion map to automatically optimize surface pressure distribution and alert nursing staff or caregivers of any potential abnormalities. Surface interface pressure can essentially be eliminated at areas that are identified as having compromised tissue perfusion or signs of tissue injury. In addition to helping patients with decubitus ulcers, the present invention can be useful in the treatment of patients with burns, chronic wounds, skin grafts, flaps, and other injuries.

Laser Doppler Flowmetry can also be used for measuring perfusion in cutaneous microcirculation in some embodiments. The technique works by illuminating the tissue of interest with light from a low-power laser. The beam of laser light is scattered within the tissue of interest and some of the light is scattered back to a sensor. Most of the light is scattered by static (non-moving) tissue, but a certain percentage of the light is scattered by moving red blood cells. The light scattered by moving red blood cells is distinct from the light scattered by static tissue (i.e. it has a unique oscillation frequency), so the oscillation frequency of the backscattered light correlates with the relative number and speed of moving red blood cells. Thus, this technique can be used to measure the relative amount of moving red blood cells and measure their average velocity. This technique is completely non-invasive and can be used to interrogate subcutaneous tissue to a depth of several millimeters. If areas of abnormal perfusion are detected, the support system can automatically eliminate surface interface pressure at those locations, and caregivers can be alerted. Pressure relieving maneuvers performed by the support system can be used to promote blood flow.

In some embodiments, it is desirable to combine perfusion data from multiple sensing modalities to increase the specificity of the detection system and thereby improve the ability to detect ischemia. The false positive rate can be decreased if the perfusion map is generated from the synthesis of data from multiple sources. For example, if the transcutaneous oxygen tension is determined to be low at position X, but the pH is normal, the temperature is normal, and the Laser Doppler Flow is normal at position X, then this can be considered a false positive transcutaneous oxygen tension measurement at position X and the support system will take no action. However, if multiple sensing modalities indicate that perfusion is compromised at position X, then the support system can immediately perform pressure relieving maneuvers at position X and can alert caregivers. The minimum number and/or type of sensing modalities that are required to initiate pressure-relieving maneuvers can be predefined by the user or caregivers. A weighted mean can be constructed using data from the different sensing modalities, where the weight of each sensing modality is determined by its importance, reliability, and effectiveness in detecting tissue ischemia.

In some embodiments, it is desirable to correlate perfusion data with position data to better address areas of compromised perfusion on the patient. Perfusion sensors can be used to determine if certain areas of the body are at risk of ischemic damage or are in the early/late stages of ischemic damage. The support system can be designed to dynamically modulate surface interface pressures, so as to promote adequate blood flow to target tissues. When the support system addresses areas of compromised perfusion, it is helpful to correlate the ischemic area with an actual physical location on the user. The methods by which this can be done will vary depending on whether the perfusion sensors are embedded in the support system or adhered to the patient's body.

In an embodiment, the support system can have one or more sensors across its surface. These sensors can be used to identify potentially ischemic areas. In order to determine what part of the body correlates with a potentially ischemic area, the system needs a reference frame to known parts of the body. Here, reference markers can be placed on the body in known reference locations such as the elbows, knees, ankles, wrists, spine, hip, etc. These reference markers can be sensed by the system using a number of potential modalities (e.g. capacitive, inductive, resistive, magnetic, RFID, etc). These reference markers can be used to demarcate known body landmarks. Each reference marker can also have unique sensible qualities (e.g. differing capacitance, resistance, inductiveness, etc.) such that the support system can distinguish between the different reference markers and thus identify the different body landmarks. In such a method, the system can know, for example, if it's sensing a reference marker for the elbow vs. the wrist. If the markers are not unique or differing, the support system can use the relative locations of the reference markers, in conjunction with information about the known shape of the user and possible orientations of the user's body to estimate the location and orientation of the user in relation to the support system. Alternatively, the support system can take the data from the sensors embedded within it to determine which sensors in the array are sensing the presence of the user and use that data, along with the data about the user's shape/size/possible motions, to make an estimate of the user's orientation and location in relation to the support surface. For example, a pressure map which is generated from a support surface that contains pressure sensors, can be used to estimate the user's location and orientation. The same principles described here for pressure sensors can be applied for most or all sensing modalities.

Referring next to FIG. 19, in an embodiment the user's position, location, and orientation relative to the support surface is estimated. A model of the body with range of motion and weight is created. This can be generic or it can include data specific to the user. The body model, in combination with the sensor data is used to generate the location map.

In some embodiments, sensors such as perfusion sensors are placed directly on the patient's body. These sensors can determine, for instance, if any areas on the user's body are ischemic. Perfusion sensors can employ a number of different sensing modalities (e.g. transcutaneous oxygen pressure, skin temperature, etc.). This biometric information, along with positional information obtained via known reference markers, can be relayed to the sensing system. In addition to information regarding the user's perfusion status, the reference markers placed on the user can also have unique identifiers (e.g. differing capacitance, resistance, RFID, etc). The perfusion sensors can thus be juxtaposed with known reference markers, so as to link perfusion and position data. Perfusion sensors and reference/location markers can be placed in close proximity to each other, or with a known relationship to each other, so as to create a close link between perfusion and position data. Knowledge of the specific location of each perfusion sensor in relationship to the support system can be used to generate a tissue perfusion map of the user. The sensing system can be responsible for sensing both the perfusion sensors and the location markers, thus allowing the sensors and markers to be smaller and less complex.

The transmission of sensor data from the user to the support system is important in some embodiments of the present invention. Perfusion sensors can detect a multitude of different physiologic factors that are markers of ischemia. If these sensors are located on the user, these sensors must be able to relay that information to the support system. One method of accomplishing this is to have wires linking the sensors on the user's body to the support system. The sensors can also be designed to wirelessly transmit information. Another method of accomplishing this is to have the perfusion sensors induce sensible changes in an indicator. The indicator is located on the user, and the indicator can be incorporated into the sensor itself. The changes within the indicator can then be sensed by the support system. For example, the perfusion sensors may induce a change in the capacitance or resistance of an indicator. This change in capacitance or resistance can be sensed by the system. Therefore, the system will be able to indirectly receive information relating to the perfusion status of the user.

Sensors can be placed over the entire body surface, or they can be strategically placed at areas that are at high-risk for becoming ischemic, such as the hip bones, tailbone, heels, ankles, and elbows. Strategically placing sensors only at high-risk areas may reduce the time required to prepare a user for perfusion sensing. Sensors can also be strategically placed at locations with a known physical relationship to a high-risk area, but not directly on the high-risk area. Using fewer sensors may also reduce the total sensor bandwidth, while not greatly reducing efficacy.

To aid in the placement of the sensors, an adhesive sheet with an array of embedded sensors can be placed on the user. The sheet has printed thereon clear landmarks, so as to aid in the proper placement of the sensor array. For example, in an embodiment the sheet has printed landmarks that are designed to correlate with anatomic landmarks, such as the L4 vertebral prominence, the ASIS, the trochanters, etc. These sheets can come in different sizes to accommodate different shapes and sizes of users. These sheets can also be designed to stretch to accommodate different sizes and shapes of users. These sheets can also be translucent, transparent, breathable, reusable, and/or removable after sensors are properly placed, leaving the sensors in place. This method of using a "sheet" of sensors can greatly increase the speed, ease, and reliability with which the sensors are placed. Sheets can be made with the features described above to conform to any body part and can also be designed to accommodate a wide range of potential sensor arrays. The sensors can also be embedded in form-fitting socks, undergarments, gloves, patches, and sleeves.

Figure 18:
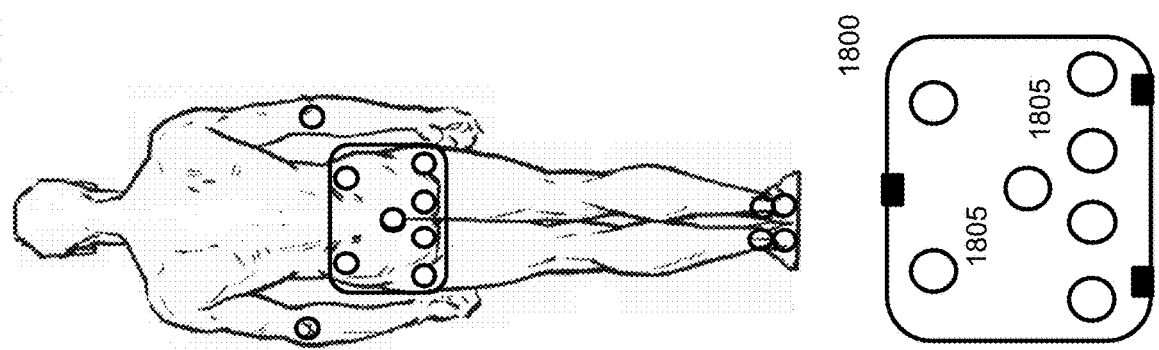
FIG. 18 illustrates the location of certain areas that are at increased risk of developing pressure ulcers and the placement of a sheet with markers and indicators for physical landmarks.

In FIG. 18, a sheet 1800 with sensors 1805 having anatomical landmarks is shown. Such a method allows for the quick and easy placement of sensors at the hip and tail bones. It should be noted that the sensors used in the present invention can be found in many locations and orientations. Possible sensor locations include, but are not limited to, embedded in the support surface, embedded in a sheet that overlays the support surface, or positioned beneath or around the support surface.

In many embodiments of the invention, it is desirable to optimize pressure at areas corresponding to body surface markers. The present invention utilizes a novel method for eliminating interface pressure at areas corresponding to wound dressings or other body surface markers. One method of accomplishing this is to embed wound dressings or body surface markers with a material that can be sensed by the system. The sensing system can then track the location of all wound dressings and body surface markers, and optimize surface pressure accordingly. Thus, interface pressure can be reduced or eliminated beneath wounds and other high-risk areas. There are many ways to make sensible wound dressings and body surface markers, a few of which are described herein.

Figure 20:
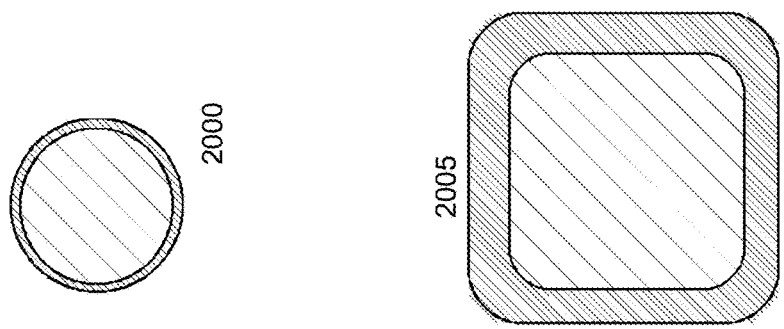
FIG. 20 illustrates markers that can take the form of adhesive patches, top, or that are built into bandages, bottom.

In an aspect of the invention, wound dressings capable of being sensed by a remote host through either a wired or wireless connection are used. Such sensible wound dressings can also comprise body surface markers 2000 and 2005, such as depicted in FIG. 20. These wound dressings and surface markers can be composed of an adhesive material, such that they can be applied to a patient's skin. The sensing system can then automatically identify the presence of a wound dressing or surface marker, and then perform pressure optimizing maneuvers at those specific locations. As the patient moves in relation to the support system, the sensing system can continually track any wound dressings or surface markers that are in proximity to the surface of the sensing system.

In some embodiments of the invention, it is desirable to incorporate surface markers into clothing worn by the patient. The surface markers used in the present invention can be incorporated into form-fitting clothing, such as socks, undergarments, gloves, patches, bracelets, or sleeves.

Figure 21:
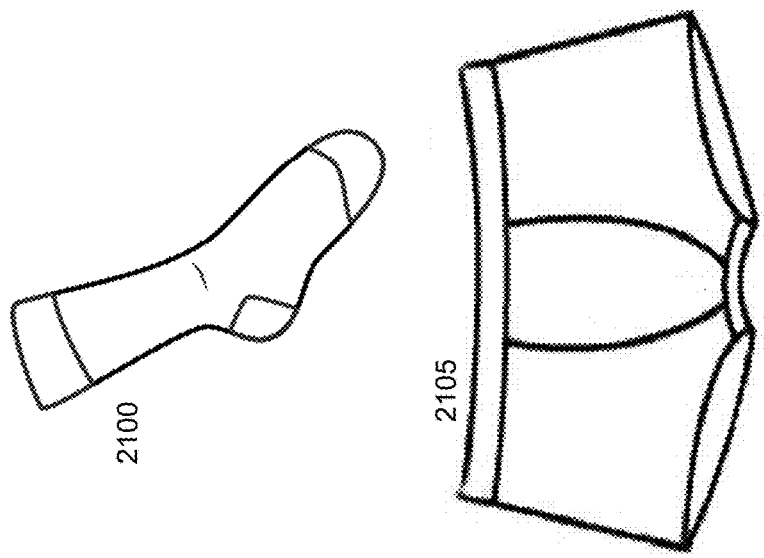
FIG. 21 illustrates articles of clothing onto which markers can be attached or into which markers can be imbedded.

In FIG. 21 a sock 2100 is shown which has been embedded with one or more sensible materials. The sensible materials can be embedded at specific locations of the sock, such as the heel, lateral malleolus and/or medial malleolus. The user can wear the sock, and when the sock is placed in proximity to the surface of the sensing system, pressure optimizing maneuvers can be performed at that specific location. As the patient moves in relation to the support system, the sensing system can continually track any socks that are in proximity to the surface of the support system. Note: socks or sleeves can be made to conform to any body surface, such as the arm or leg. Also, specialized sleeves can be designed to fit over specific "at risk" areas, such as a tissue graft or flap.

Also in FIG. 21, an undergarment 2105 is shown which has been embedded with one or more sensible materials. The sensible materials can be embedded at specific locations, such as the hips, and sacrum. The user can wear the undergarment, and when the undergarment it is placed in proximity to the top surface of the support system, pressure optimizing maneuvers can be performed at that specific location. As the patient moves in relation to the support system, the sensing system can continually track the undergarment, as long as it remains in proximity to the surface of the support system. The undergarment should remain in a fixed position relative to the patient, such that any movement of the undergarment directly reflects movement of the patient.

Figure 22:
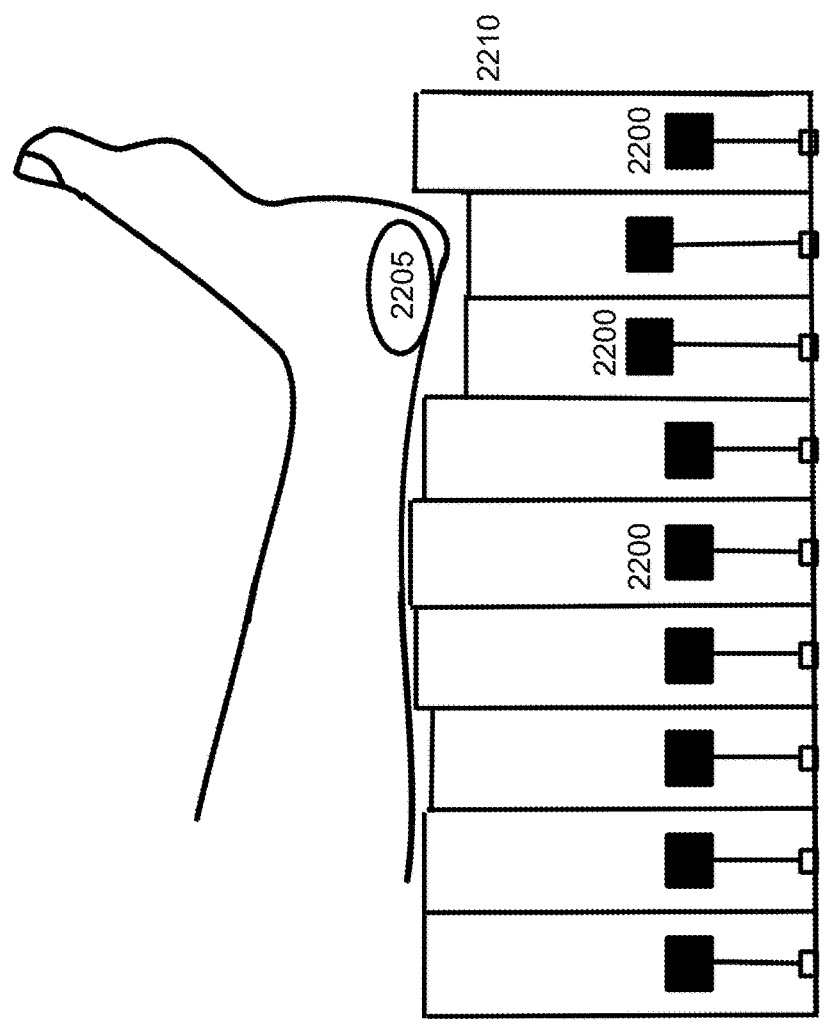
FIG. 22 illustrates the operation of a magnetic sensor, sensing and causing a reaction to a marker.

In an aspect of the invention, magnets 2200 can be implemented to create sensible body surface markers, as shown in FIG. 22. One method of creating sensible wound dressings and body surface markers 2205 is to embed these items with a flexible, soft, and magnetically receptive material. The magnetically receptive wound dressing then interacts with small magnets, or electromagnets, that are contained within each of the support surface's air columns 2210. When the magnetically receptive wound dressing is put in proximity to the support surface, the magnets contained within the support surface are attracted towards the wound dressing. Each air column comprises a force sensor that can measure the magnitude of the magnetic attraction. The support surface then responds by decreasing the air pressure in those air columns that register a high force. As the registered force increases, the air pressure within the corresponding columns decreases by a proportional amount. Thus, interface pressure is relieved or eliminated under areas that have magnetically receptive dressings. In another embodiment, the support surface contains an array of magnetic sensors positioned at some distance beneath the top layer of the support surface. This magnetic sensor array can be used to determine the coordinates of magnetic body surface markers placed within proximity to the sensor array. The location data can be communicated with the support surface, which then optimizes surface pressure or delivers targeted therapy based on this information.

FIG. 22 depicts a method for eliminating surface pressure beneath wounds using such magnets. A dressing that contains a magnetically receptive material is used to cover any wound or tissue. The sensing system contains small magnets that are attracted to this magnetically receptive wound dressing when the two are placed in proximity. The resulting magnetic force will be sensed by the system, and air pressure within the corresponding air columns will be decreased.

Another method that utilizes magnets is to have magnetic sensors embedded in the support surface. The surface markers can be made of a magnetic material which can be easily recognized by one or more magnetic sensors embedded in the sensing system. Magnetic sensors are relatively cheap, highly sensitive, and allow for non-contact sensing. Non-contact sensing is advantageous because the user will not have to "feel" the sensors, which could be uncomfortable. A specific area of a subject's body can be demarcated using a wound dressing, body surface marker, or even clothing (i.e. sock, underwear, glove, etc.) that has been embedded with a magnetic material. Or, a specific area of a subject's body can be marked out using a magnetic ink pen. The sensing system can then detect the magnetic field strength and/or magnetic field direction created by the magnetic materials to: 1) detect the physical presence of our test subject, 2) locate specific areas on our test subject's body, 3) detect any movement of our test subject relative to the support system, 4) optimize interface pressure beneath the magnetic surface marker. The magnetic sensors can be used to measure the magnetic field strength and/or the magnetic field direction produced from any magnetic surface markers placed in proximity to the support system. There may be some advantages to measuring magnetic field direction versus magnetic field strength, which include: insensitivity to the temperature coefficient of the magnet, less sensitivity to shock and vibration, ability to withstand large variations in the distance between the sensor and the magnet, and the ability to detect angular or linear movement of magnetic objects.

The sensing system of the present invention can also utilize a fabric that can conduct electricity. Body surface markers can then be placed on the patient, such that when they come into contact with the sensing system there is a measurable change in resistance. Using this method, the sensing system can track body surface markers on the patient and regulate surface pressure accordingly.

Similarly, conductive thread can be interspersed with normal fabric to add conductivity to a fabric or material. This can allow normal fabric, paper, or plastic materials to become conductive (or have lower resistance) while maintaining, for the most part, their other properties.

To prevent undesirable interference with other treatment or patient management regimens, fuses that limit the amount of current that can pass through the conductors in the sensing device can be placed in the sensor sheet. They can be placed, for example in series with conductors in contact with the bed or patient. If for instance, defibrillators are to be used on the patient, the fuses can be used to reduce the flow of current along the conductors.

These fuses can be separate from the conductors, but can also take the form of segments of the conductors. In either implementation, only a predetermined maximum current is permitted to flow through them before they break the circuit. In at least some embodiments, high value resistors can be used to limit current to levels which present no danger to either the patient or other equipment in the vicinity.

An alarm function can be incorporated into the sensing system. If the sensing system determines that a particular region of the body (as defined by body surface markers) has been experiencing sub-optimal perfusion for an extended period of time, then caregivers can be alerted via an audible or visual alarm. The alarm can be transmitted wirelessly to a nursing station.

The sensing system of the present invention can utilize one, some or all of the sensors described in this document to identify areas of compromised tissue perfusion. The support system can then optimize surface pressure in order to restore blood flow to under-perfused areas.

Any of the above concepts, sensors, and devices can be applied for use on a chair, wheel chair, operating table, or any other support surface.

In an embodiment, pressure sensors are embedded into the surface of the operating room table. The pressure sensors are used to generate a pressure map of the operative patient. If any area registers a high pressure for an extended amount of time, an alarm will sound. Then, the patient the patient's position can be adjusted so that the pressure is relieved.

A system can be designed where a sheet of pressure sensors is securely placed over the surface of the operating table prior to the operation. Alternatively, a sheet composed of a pressure sensitive fabric can also be used. The sheet may be disposable.

When the sensing system detects areas of compromised tissue perfusion or tissue injury, interface pressure can be eliminated at those specific locations. Stated differently, pressure at specific locations on the patient's body can be offloaded in some embodiments of the present invention. The support system can be designed to relieve pressure around specific locations in a gradual fashion. Such gradual pressure offloading prevents sudden and dramatic changes in interface pressure. Dramatic pressure changes can lead to, amongst other things, poor circulation or a feeling of "dropping out" of the support system. The magnitude of the pressure gradient can be adjusted and the minimum interface pressure can be set. The rate of pressure offloading can also be adjusted. The rate of pressure offloading per unit distance from a given location can be defined by the user or caregivers. The rate of pressure offloading over time can be defined by the user or caregivers. These adjustments can be made to maximize comfort or to optimize the depressurization at and around target areas.

Figure 23:
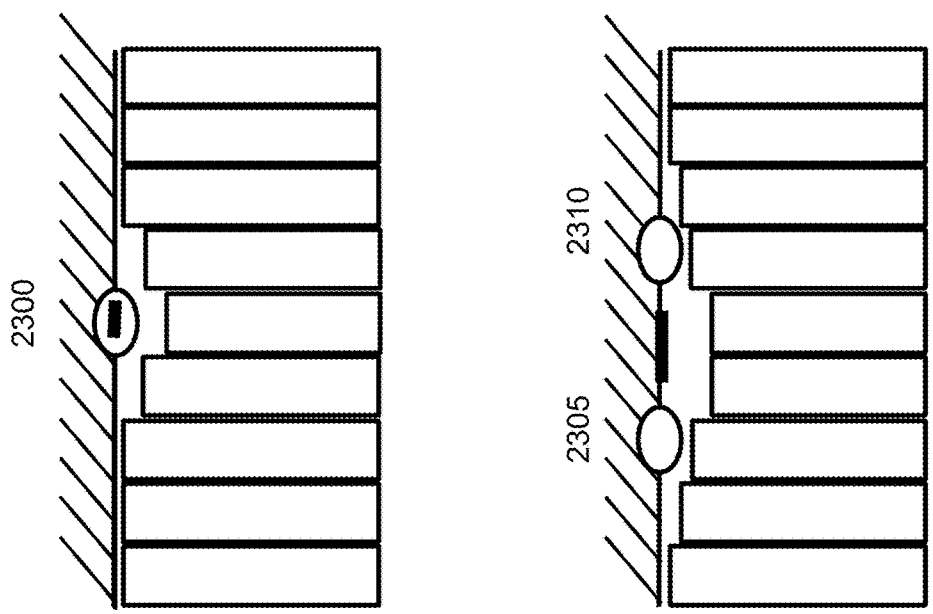
FIG. 23 illustrates the operation of a support reacting to one or more markers, top and bottom respectively.

In FIG. 23, certain areas requiring pressure relief are marked (indicated by the ovals). In the case of a single marker 2300, interface pressure is gradually reduced and the pressure is lowest directly beneath the marker. When multiple markers 2305-2310 surround an area that requires pressure relief, the pressure is gradually decreased and the pressure is lowest within the region cordoned off by the markers at a computed optimal location.

The support system can be designed in some embodiments such that it allows for sequential increases or decreases in interface pressure at specific locations. Such sequential pressurization and depressurization can be used to promote blood flow to selected tissues. In one implementation of this method, a support surface that contains a plurality of air columns is embedded with an array of sensors, such that the perfusion status of the user can be determined at discrete locations. The individual air columns can regulate their air pressure in order to optimize blood flow to target tissues. The dynamic air pressure changes can be designed to follow certain patterns that are known to facilitate blood flow, such as having pulses or waves of pressure move radially towards or away from target tissues. Other modes of pressure change are also possible.

In FIG. 24, different patterns of pressure change are shown. The dotted lines show local maxima of pressure that shift as indicated by the thick arrows. Shown here are expanding rings of pressure 2400, rotating radial lines of pressure 2405, and lines of pressure moving in one direction 2410. Also shown is the pressure at high risk areas being lowered or eliminated using any given pattern of pressure change.

In addition to varying the maximum pressure of an alternating pressure support system, other features can be modulated. These include, for any location along the support system, the minimum pressure, the frequency of pressure changes (including a frequency of 0 Hz, i.e. no pressure change), the duration of high pressure (or duty cycle), the amplitude change, the maximum and minimum amplitude, and the rate at which pressure changes occur. Location sensing of body surface markers can allow for these variations in pressure optimization to be targeted to specific areas on the body. One example of this is for the head to be demarcated, such that surface pressure at this location remains relatively or absolutely constant, so as to allow for a stable head support.

In some embodiments, the support surfaces and devices described in this document can employ learning algorithms that determine which pressure optimization techniques work best for each individual patient. The algorithms can take into account perfusion data from sensors that is acquired before, during, and after different pressure optimization maneuvers are performed. The effectiveness of the different pressure optimization maneuvers is recorded and assessed to determine which maneuvers, or of combination of maneuvers work best for an individual patient. Though this can be effective for any user, those users who spend more time on the support surface will benefit most from having a pressure optimization protocol that is more robust and customized based on their specific physiologic parameters. Though perfusion is one measure that can be optimized by the learning algorithm, other measures can also be optimized using the learning algorithm.

Certain locations on the body are especially susceptible to developing ulcers, such as the hip bones, tailbone, heels, ankles, and elbows. Areas at high-risk for developing ulcers can be demarcated using body surface markers that are applied using an adhesive sheet, as shown in FIG. 18. The lower image shows a more detailed view of the adhesive sheet that is used to apply multiple body surface markers both quickly and also in the correct orientation with respect to the patient and each other.

In these locations, the pressure is often concentrated over bony prominences. The use of cushioning and supportive materials at these sites can distributes pressure over a larger area, thus relieving pressure over bony prominences. The use of such devices can help prevent ulceration and aid in the healing of wounds and ulcers.

One common problem with such devices is that pressure is relieved at high-risk locations while by transferring pressure to other sites, thereby increasing the risk of ulceration at these other sites. Two improvements are described herein: 1) utilizing a gradient of depressurization and 2) having the support cushion perform dynamic pressure optimization maneuvers.

A currently available cushion and supportive device that fits on the heel is often used to help relieve pressure on the heel. Whereas the pressure can be easily distributed in the case of a heel or elbow (given their low mass), the improvements mentioned above can allow cushions and supportive materials to be used at heavily loaded areas, such as the hip and tailbone.

FIG. 27 shows the pressure adjustments in one embodiment for a support surface 2700. The pressure is reduced at the high-risk area 2705, and there is no dramatic pressure differential between the edges of adjacent columns 2710 of the cushion. The resulting pressure drop is gradual. This method of gradual pressure redistribution can be used to optimize perfusion at high-risk areas while also improving patient comfort.

The pressure gradient can be adjusted and customized for each specific user, body part, or wound site. Discrete areas of individually controlled pressure exist in the cushion. The pressure at discrete areas within the cushion can be independently regulated by adding/subtracting a substance from these areas. This substance can be a soft solid material such as foam; a fluid such as water; or a gas such as air.

In addition to a pressure gradient, the cushion/support device can also create shifting/or dynamically changing pressures. In one instance, this can be accomplished by having the pressure within the individual chambers of the cushion controlled by a pump or other air pressurization device. The pressures can then be automatically adjusted and modulated over time. The pressure changes can follow selected patterns to facilitate blood flow, such as having pulses of pressure that move radially away or towards the side of risk or damage. Similarly, the pulses or waves of pressure can fan out from the area of risk and/or move around it. Other modes of pressure change are also possible.

In FIG. 25, different patterns of pressure change in a cushion are shown. The dotted lines show local maxima of pressure that shift as indicated by the thick arrows. Here shown are expanding rings of pressure 2500 and rotating radial lines of pressure 2505. Also shown is the pressure at the areas of risk being lowered or eliminated with any given pattern of pressure change.

These same techniques can be applied to the heel and elbow and other areas of the body as well.

The support cushion described above can be designed to accommodate any or all of the sensing mechanisms described in this document. By incorporating perfusion sensors into the support cushion, the hemodynamics of the target tissue can be monitored and pressure can be optimized to facilitate blood flow. Any of the concepts, sensors, and devices mentioned in this document can be used in conjunction with the support cushion.

Using the concepts and sensors described in this document, sleeves, patches, or dressings can be designed that monitor the perfusion status of a user at any location on their body (not just tissue that is in contact with the support system). If abnormal perfusion is detected, an alarm can be used to alert caregivers. Such Such devices can be particularly useful in monitoring the perfusion of a tissue graft or flap.

An arrangement of air columns in different orientations is one variation of a support surface that allows for fine two-dimensional control of surface pressure with fewer air columns required.

Shown in FIG. 26 is a support surface with two layers of horizontal air columns 2600-2605 that are arranged perpendicular to each other.

If only a column on the top layer deflates, the rows in the bottom layer will expand as their pressure is higher than the top layer such that the area covered by the deflated top layer column is supported by the bottom layer rows. The top layer columns and bottom layer rows are arranged perpendicular to each other. If only a bottom layer row is deflated, the top layer column expands such that the area covered by the bottom layer row is supported by the top layer column. If a top layer column and a bottom layer row are both deflated, then the only area not fully supported by both top and bottom layers corresponds to the area where the deflated column and row intersect. Thus, modulating the pressure in both rows and columns allows surface pressure to be controlled at specific locations.

The devices and methods of the present inventions have a variety of other applications. For example, the support system can be designed to minimize shear forces or regulate temperature or adjust humidity. There are also applications outside of the treatment of wounds. For example, the sensing system can be utilized by patients with diseases such as Cystic Fibrosis, where they require localized chest percussion therapy (CPT) at regular intervals. More specifically, embodiments of the present invention for creating variable pressure patterns can be used to create an automated percussion protocol that optimizes the expulsion of mucus in patients with Cystic Fibrosis. The same principle can be used in other applications where percussion therapy can be of benefit. Other potential applications of the present invention are described briefly herein.

The ability to detect shear forces directly and to eliminate them improves the treatment and prevention of wounds and pressure ulcers. One method to detect shear forces is to place shear sensors, such as strain gauges or piezoresistive sensors, at the interface of the skin and the support surface. In one implementation, the shear sensors can be imbedded at or just beneath the surface of the support surface. The shear sensors can also be placed in a sheet that is placed on top of the support surface. The shear sensors can also be attached directly to the skin. These shear sensors can be used to sense a force that causes a stretch or compression in directions that are tangential to the surface of the skin.

Another approach is to use conductive fabric or threads that change resistance based on their stretch. Measuring changes in resistance can be used to quantify stretch in the surface which can be correlated to shear forces. Shear forces can be estimated by knowing the orientation of the patient and/or the position of the support surface on which the patient is lying or sitting.

Once a shear force is detected, a number of actions can be taken, depending upon the embodiment. One or more shear sensors can form a map of the shear forces at different locations along the support surface or on the skin of the user. The areas experiencing highest shear forces can be highlighted to alert the user or caregiver to reposition the user to reduce shear forces. A map of shear forces along the support surface or on the skin of the user can be generated to monitor shear forces.

In addition to detecting shear forces, embodiments of the support surface can be used to automatically eliminate excess shear forces. Once a shear force above a certain threshold is detected, the support surface determines the location where the force is generated. A method similar to that discussed above for correlating perfusion sensor data with patient position can be used for sensor data localization, where shear sensors are used instead of perfusion sensors. The support surface can then adjust the interface pressure at and around the location of the shear force, so as to relieve the shear force.

One method of automatically eliminating shear forces involves increasing pressure at areas surrounding the area of increased shear force, and then reducing the pressure at the area of increased shear force, until sufficient pressure is relieved such that the skin/tissue and support surface may move/slide relative to each other.

In order to prevent excessive frictional forces, the reduction in pressure can be fast and allow for complete elimination of pressure. Such a method allows for relative motion of the skin and support surface without contact. The pressure changes that aim to reduce shear forces can be temporary, so as to allow the support system to quickly reacquire the optimal resting pressure conditions.

The pressure changes created by an embodiment of the invention that aim to reduce shear forces can employ moving pressure waves, rings of pressure reduction, or alternating areas of increased/decreased pressure. The optimal method of shear force reduction can depend on the size, shape, and fragility of each specific skin area.

The support system can incorporate a feature in which a sufficiently high shear force must be present for a certain amount of time before any action is taken. Such a method can help eliminate actions triggered by transient and self-limited increases in shear forces.

The user, perhaps due to sensory deficits, may not be able to feel shear forces and therefore may not be able to adjust their position accordingly. In the present invention, shear forces can be monitored and automatically eliminated. The user and/or caregiver can be alerted if shear forces cannot be automatically eliminated by the support surface.

When the shear force sensors are not placed directly on the skin, but are instead placed, for instance, in the support surface, some of the shear forces detected may not be transferred to the skin. Instead these detected shear forces may be due to pressure and the natural stretch of the material in which the sensor is imbedded. Since the shear force experienced by the skin is the measurement of interest, it is useful to determine which forces measured are most likely transferred to the skin. One method to do this is to correlate a shear force sensing map with a pressure sensing map. Where the pressure is sufficient and likely to be responsible for a given sensed shear force, this shear force reading can be ignored or subtracted. The remaining shear forces can be assumed to be more likely to be transferred to the skin. This method can be customized to varying degrees by allowing adjustable levels of ignoring, subtracting, or weighting of data from shear forces sensors.

Moisture and temperature regulation can also be important in the prevention and treatment of wounds. For moisture it is important to keep areas of uninjured skin dry in order to avoid maceration. For wounds, it may be important to keep these areas moist and to not let them dry out. The humidity of the air surrounding the skin and the presence of fluids can be detected by the sensing system. Humidity sensors and fluid sensors can be placed on the skin or in the support surface. Wound areas can be demarcated, and areas that have suboptimal moisture levels, whether too wet or too dry, can be detected. For areas with excess moisture, the support surface can act to reduce moisture. For instance, the permeability of the support surface can be changed. The support surface can have water channels that open and allow for fluid to drain, be wicked away, or be suctioned out. The support surface can also allow for gas to be blown in and exit, so as to allow for moisture to evaporate. The support surface can reduce the pressure at a certain area to allow for gas to flow between the skin and the support surface. In areas with insufficient moisture, the moisture reduction methods can be stopped or moist gas can be delivered to the area of reduced moisture.

Temperature regulation is important for wound prevention and treatment. Temperature regulation is a problem particularly for users with impaired body temperature regulation. Individuals with a spinal cord injury (SCI) may have difficulty maintaining a constant body temperature, with loss of reflex sweating or regulation of blood flow. For temperature sensing, several methods exist, including thermisters, radiant heat detection, and IR sensors. Once an area of suboptimal temperature is detected, the support surface can act to correct the temperature. Several methods can be used for temperature control including, but not limited to: pumping heated or cooled liquids or gas near the surface of the support surface; pumping gas between the skin and support surface to encourage heat loss by evaporation; using thermoelectric heating and cooling elements; using electric heating elements; and alerting the user or caregivers of the suboptimal temperature, so that action can promptly be taken.

The support surface can optimize the surface temperature at discrete locations on the user's body. It is known that heat delivered to specific regions of the body, such as the back, can have a relaxing and therapeutic effect. Since the sensing system of the present invention can identify specific locations on a user's body, heat can be delivered to a user at specific locations. Similarly, cooling can be delivered to any part of the body. The sensing system can determine the location of these specific body locations, either by generating a physical location map of the user or by employing markers on the user's body. If body surface markers are used, multiple unique body surface markers can be applied to specific areas of the body, such that the temperature at each body surface marker can be different. Heating and cooling cycles and protocols can also be employed.

In some embodiments, knowing the position of the user and being able to change, sufficiently, the pressure across the support system at specific locations allows for automatic rolling of users. For example, if users are lying on their back, pressure can be increased on one side of their body while pressure is simultaneously being decreased on the other side, effectively causing or encouraging a roll. This can be extremely beneficial for patients who are prone to developing pressure ulcers, and should be rolled frequently. This can also be useful, for instance, for users with sleep apnea or snoring problems who may experience fewer sleep disturbances while sleeping on their side. In such a situation, the support surface can detect when a user is in an unfavorable position and can roll them accordingly. The system can detect when a sufficient roll has been achieved, at which point the surface pressure may revert back to its normal state.

For patients with CHF, the support system can adjust to tilt the patient (head up and feet down) to decrease strain on the heart. This can be used in conjunction with a pulse oximeter, or other sensors, to detect small changes in blood oxygenation.

With the use of body surface makers, the system can identify body surface regions corresponding to the lung fields and deliver percussion or vibration therapy directly to those locations. Percussion and vibration therapy can also be delivered in a specific pattern with respect to the lung fields in order to maximize expectoration of respiratory mucus and debris. Pulmonary therapy delivered in this manner may aid in keeping the lungs clear.

The inventions and devices described in this document can also be designed for use by the general consumer population. One implementation for the general consumer is a device that generates a physical location map of a user's body and then optimizes surface pressure for the purposes of enhancing ergonomics. This allows the support system to automatically and dynamically customize ergonomics for each specific user and in response to the user's current position and specific problem. Such technology benefits those who have back problems who require, for instance, specific lumber support. The sensing system is able to identify the lumbar region of the user, and optimize surface pressure to support the lumbar region. Furthermore, the support system in such an embodiment is able to adjust pressure across its surface to allow the user to rest in a neutral, ergonomic, and healthy position.

In another aspect of the invention, an embodiment of the sensor 300 configured to detects sleep cycles can be used with the system of FIG. 1 to enable the sensing system to be able to function as an alarm clock. It is beneficial to be awoken at a specific stage in the sleep cycle (i.e. immediately after REM sleep). The sensing system can determine what stage of the sleep cycle a user is in by either directly measuring the EEG or by indirectly monitoring other biometric data (such as movement, because people are paralyzed during REM) in the manner taught hereinabove. The user is then awakened at the optimal time via any sensory stimuli (visual, auditory, olfactory, touch) appropriate to that patient. The support system can also regulate surface pressure to encourage the patient to exit the support system at the desired time. The patient can designate a time range in which they would like to be awoken. The system can then identify the best time within this range to wake the patient.

In another aspect of the invention, the operating table can have a pressure sensing mat across its surface. The mat can be embedded into the operating table, or can be securely wrapped across the surface of the support system (like a bed sheet). A pressure map of the patient can then be generated. If areas of high pressure are noted for greater than one hour, or other predefined amount of time, then the caregiver is alerted. Since patients are typically paralyzed when on the operating table, they should not be moving, and there is no need to correlate position and pressure maps. An LCD display associated with the pressure sensors can be used to indicate where the area of high pressure is located in relation to the operating table.

Pressure sensing pads can be used to monitor pressure between body parts or between body parts and other objects. For example, between the knees, between elbows/wrists and the side of the body. When the patient is lying on the side or when the arms are bound close these areas can experience high pressures as well. The pressure mats can be shaped and formed to help stay in place and also help to pad these areas. Caregivers can be alerted if sustained periods high pressure are measured.

Because the sensing system can determine the exact position of the patient relative to the support system, the support system can be used to aid in rapid airway management by automatically positioning the patient in an orientation that facilitates intubation. For example, the neck can be forced to protrude, so as to increase glottic exposure. The head of the bed can be elevated, so as to decrease the work of breathing (obese patients can sometimes have difficulty breathing while lying flat). Elevating the head of the bed can also be useful for patients with sleep apnea or congestive heart failure, where a vital signs monitor can be used to determine the appropriate incline level (as the respiratory rate increases or oxygen saturation decreases, the level of incline increases).

In another aspect of the invention, the maximum size of an acceptable "indentation" in the support surface can be predefined, so as to prevent the user from falling into a hole created in the support system. Having a maximum limit can be important when treating patients with large wounds. Smaller areas of reduced pressure can migrate under the wound area, so as to minimize pressure over a large space for periods of time.

It will also be appreciated that, while the foregoing primarily discusses support surfaces for hospitals and nursing homes, the technology of the present invention has broader potential applications. For example, the technology can be utilized in the home or car. For example, a wallet in the back pocket can be a nuisance when driving. A wallet can be embedded with or contain a sensible material. Then, whenever the user's wallet is placed in proximity to the seat of the car or wheelchair or other support surface, a small indentation is automatically created at the location corresponding to the wallet. This allows the patient to sit comfortably in the seat of their car, without having to remove their wallet from their back pocket. This method need not be confined to wallets, and instead is appropriate for any objects close to the body that create discomfort or increase the risk of pressure ulcer formation.

This document focuses on the use of "air columns" as the basis of the support system. It should be noted that air columns are not required in all embodiments. Any support system that can regulate its surface pressure at discrete locations can be used. Other methods include, but are not limited to: hydraulic systems, columns of bubbling sand and mechanical pistons.

Having fully described a preferred embodiment of the invention, and numerous aspects thereof, as well as various alternatives, those skilled in the art will recognize, given the teachings herein, that numerous alternatives and equivalents exist which do not depart from the invention. It is therefore intended that the invention not be limited by the foregoing description, but only by the appended claims.

We claim:

1. A method for automatically adjusting a turn protocol for a person, the method comprising:
providing the turn protocol for the person supported at least temporarily by a support surface, wherein the turn protocol defines a pressurization measure representing a pressurization of a particular body region,
receiving, at a processor, sensor signals from one or more sensors,
identifying, by the processor, based on the received sensor signals, when the person is in a pressurization position corresponding with the particular body region,
monitoring, by the processor, the pressurization measure over time based on the identifying step, including (a) increasing the pressurization measure for a first pressurization period spent on the support surface and in the pressurization position and (b) decreasing the pressurization measure at a first depressurization rate for a first depressurization period spent on the support surface but out of the pressurization position,
detecting, based on the received sensor signals, one or more body movements selected from the group of body movements consisting of a bed exit event, a standing event, and an ambulation event, and
in response to the detection of the one or more body movements:
selecting a constant predetermined depressurization rate higher than the first depressurization rate, and
decreasing the pressurization measure at the constant predetermined depressurization rate during a duration of a second depressurization period spent out of the pressurization position.

2. The method of claim 1 comprising selecting the constant predetermined depressurization rate based on person-specific data.

3. The method of claim 2, wherein the step of selecting the constant predetermined depressurization rate based on the person-specific data comprises selecting the constant predetermined depressurization rate based on a determined frequency or duration of the one or more body movements.

4. The method of claim 1 wherein selecting the constant predetermined depressurization rate is based on predetermined parameters for care.

5. The method of claim 1, wherein the step of receiving the sensor signals from the one or more sensors comprises receiving the sensor signals from the one or more sensors provided in a sensor device affixed to the person or carried by an article worn by the person.

6. The method of claim 1, wherein the step of receiving the sensor signals from the one or more sensors comprises receiving acceleration data from one or more accelerometers.

7. The method of claim 1, wherein:
detecting the one or more body movements comprises detecting the bed exit event, and
the second depressurization period spent out of the pressurization position comprises a period related to the bed exit event during which the person is out of bed.

8. The method of claim 1, wherein:
detecting the one or more body movements comprises detecting the standing event, and
the second depressurization period spent out of the pressurization position comprises a period during which the person is standing.

9. The method of claim 1, wherein:
detecting the one or more body movements comprises detecting the ambulation event, and
the second depressurization period spent out of the pressurization position comprises a period during which the person is ambulating.

10. A method for automatically adjusting a turn protocol for a person, the method comprising:
providing the turn protocol for the person supported at least temporarily by a support surface, wherein the turn protocol defines (a) a pressurization measure representing a pressurization of a particular body region, and (b) a depressurization rate for decreasing the pressurization measure,
receiving, at a processor, sensor signals from one or more sensors,
identifying, by the processor, based on the received sensor signals, when the person is in a pressurization position corresponding with the particular body region,
monitoring, by the processor, the pressurization measure over time based on the identifying step, including (a) increasing the pressurization measure for periods spent in the pressurization position and (b) decreasing the pressurization measure, based on the depressurization rate defined by the turn protocol, for periods spent out of the pressurization position,
determining person-specific historical body movement information, including at least one of:
determining a historical bed exit frequency for the person based on a series of bed exit events detected based on the received sensor signals,
determining a historical standing duration for the person based on a series of standing events detected based on the received sensor signals, or
determining a historical ambulation distance or speed for the person based on a series of ambulation events detected based on the received sensor signals, and
adjusting the depressurization rate based on the person-specific historical body movement information, and
decreasing the pressurization measure using the adjusted depressurization rate.

11. The method of claim 10, wherein the step of receiving the sensor signals from the one or more sensors comprises receiving the sensor signals from the one or more sensors provided in a sensor device affixed to the person or carried by an article worn by the person.

12. The method of claim 10, wherein the step of receiving the sensor signals from the one or more sensors comprises receiving acceleration data from one or more accelerometers.

13. The method of claim 10, wherein:
determining the person-specific historical body movement information includes determining the historical bed exit frequency for the person based on the series of detected bed exit events, and
adjusting the depressurization rate based on the person-specific historical body movement information comprises adjusting the depressurization rate as a function of the determined historical bed exit frequency.

14. The method of claim 10, wherein:
determining the person-specific historical body movement information includes determining the historical standing duration for the person based on the series of detected standing events, and
adjusting the depressurization rate based on the person-specific historical body movement information comprises adjusting the depressurization rate as a function of the determined historical standing duration for the person.

15. The method of claim 10, wherein:
determining the person-specific historical body movement information includes determining the historical ambulation distance or speed for the person based on the series of detected ambulation events, and
adjusting the depressurization rate based on the person-specific historical body movement information comprises adjusting the depressurization rate as a function of the historical ambulation distance or speed for the person.

16. A system for automated monitoring of a person, comprising:
a wearable sensor device body configured to be secured to the person or to an article worn by the person;
at least one sensor provided in the wearable sensor device body and configured to generate sensor signals regarding an orientation of the person; and
a processor configured to:
receive sensor signals from the at least one sensor,
identify based on the received sensor signals, when the person is in a pressurization position corresponding with a particular body region,
manage a pressurization timer for the pressurization position, including (a) increasing the pressurization timer for a first pressurization period spent on the support surface and in the pressurization position and (b) gradually decreasing the pressurization timer at a first depressurization rate for a first depressurization period spent on the support surface but out of the pressurization position,
detect, based on the received sensor signals, a bed exit event, a standing event, or an ambulation event, and
in response to detecting the bed exit event, the standing event, or the ambulation event:
select a second depressurization rate higher than the first depressurization rate, and
gradually decrease the pressurization timer at the second depressurization rate during a duration of a second depressurization period spent out of the pressurization position, such that the pressurization timer is gradually decreased over time by an amount defined by the duration of the second depressurization period.

17. The system of claim 16, wherein the processor is provided in the wearable sensor device body.

18. The system of claim 16, wherein the processor is remote from the wearable sensor device body and configured to receive the sensor signals from the at least one sensor via wireless communications.

19. The system of claim 16, wherein the second depressurization period comprises a period during which the person is out of bed.

20. The system of claim 16, wherein the second depressurization period comprises a period during which the person is standing.

21. The system of claim 16, wherein the second depressurization period comprises a period during which the person is ambulating.

* * * * *